US010048269B2

(12) United States Patent
Stern et al.

(10) Patent No.: US 10,048,269 B2
(45) Date of Patent: Aug. 14, 2018

(54) ASSAY METHODS INVOLVING DISSOCIABLE NANOPARTICLES

(71) Applicant: SeLux Diagnostics, Inc., Cambridge, MA (US)

(72) Inventors: Eric Stern, Jamaica Plain, MA (US); Aleksandar Vacic, Cambridge, MA (US); Alec Nathanson Flyer, Boston, MA (US)

(73) Assignee: SELUX DIAGNOSTICS, INC., Charlestown, MA (US)

( * ) Notice: Subject to any disclaimer, the term of this patent is extended or adjusted under 35 U.S.C. 154(b) by 114 days.

(21) Appl. No.: 14/809,116

(22) Filed: Jul. 24, 2015

(65) Prior Publication Data

US 2016/0047816 A1    Feb. 18, 2016

Related U.S. Application Data

(60) Provisional application No. 62/194,062, filed on Jul. 17, 2015, provisional application No. 62/142,721, filed on Apr. 3, 2015, provisional application No. 62/053,250, filed on Sep. 22, 2014, provisional application No. 62/029,270, filed on Jul. 25, 2014.

(51) Int. Cl.
*G01N 33/58* (2006.01)
*B82Y 15/00* (2011.01)

(52) U.S. Cl.
CPC ............ *G01N 33/587* (2013.01); *B82Y 15/00* (2013.01)

(58) Field of Classification Search
CPC .............................. B82Y 15/00; G01N 33/587
See application file for complete search history.

(56) References Cited

U.S. PATENT DOCUMENTS

| 5,173,406 | A | 12/1992 | Hosoda et al. |
|---|---|---|---|
| 6,100,394 | A | 8/2000 | Collins et al. |
| 7,309,723 | B2 | 12/2007 | Porter et al. |
| 7,820,394 | B2 | 10/2010 | Lelental et al. |
| 8,722,881 | B2 | 5/2014 | Ghosh et al. |
| 8,754,206 | B2 | 6/2014 | Sengupta et al. |
| 2004/0014073 | A1* | 1/2004 | Trau ..................... G01N 33/587 435/6.16 |
| 2004/0175768 | A1 | 9/2004 | Kushon et al. |
| 2005/0282237 | A1 | 12/2005 | Ishimori |
| 2010/0171043 | A1 | 7/2010 | Burke et al. |
| 2012/0329680 | A1 | 12/2012 | Sengupta et al. |
| 2015/0050672 | A1 | 2/2015 | Lelental et al. |

FOREIGN PATENT DOCUMENTS

| CA | 2 504 559 | A1 | 10/2006 |
|---|---|---|---|
| EP | 2 653 867 | A1 | 10/2013 |
| WO | WO 2002/12888 | A2 | 2/2002 |
| WO | WO 2009/018348 | A1 | 2/2009 |
| WO | WO 2010/142960 | A1 | 12/2010 |
| WO | WO 2013/095137 | | 5/2013 |
| WO | WO 2016/015027 | A1 | 1/2016 |
| WO | WO 2017/015145 | A2 | 1/2017 |

OTHER PUBLICATIONS

Van Lente, "Exocrine Disorders," in Clinical Pathology of Pancreatic Disorders, edited by John A. Lott, Humama Press, 1997, pp. 43-44.*
Bokare, et al., "Review of Iron-Free Fenton-Like Systems for Activating $H_2O_2$ in Advanced Oxidation Processes", Journal of Hazardous Materials, (Jun. 30, 2014), vol. 275, 121-135.
Bruemmel, et al., "On the Influence of Different Surfaces in Nano- and Submicrometer Particle Based Fluorescence Immunoassays", Langmuir, (Jan. 10, 2014), vol. 20, No. 21, 9371-9379.
Bunyakul, et al., "Cholera Toxin Subunit B Detection in Microfluidic Devices", Analytical and Bioanalytical Chemistry, (Jun. 9, 2008), vol. 393, No. 1, 177-186.
Chan, et al., "Reaction-Based Small-Molecule Fluorescent Probes for Chemoseletive Bioimaging", Nature Chemistry, (Nov. 23, 2012), vol. 4, 973-984.
De La Rica, et al., "Plasmonic Elisa for the Ultrasensitive Detection of Disease Biomarkers with the Naked Eye", Nature Nanotechnology, (Oct. 28, 2012), vol. 7, No. 12, 821-824.
De La Rica, et al., "Supplementary Information: Plasmonic ELISA for the Ultrasensitive Detection of Disease Biomarkers with the Naked Eye", Nature Nanotechnology, (Oct. 28, 2012), vol. 7, No. 12, S1-S12.
Gomes, et al., "Fluorescence Probes Used for Detection of Reactive Oxygen Species", Journal of Biochemical and Biophysical Methods, (2005), 65, 45-80.
Mouffouk, et al., "Polymeric Micelle-Based Bioassay with Femtomolar Sensitivity", Analytical Biochemistry, (Oct. 22, 2007), vol. 372, No. 2, 140-147.
Parnell, et al., "Electrochemical Sensing of Hydrogen Peroxide Using a Colbalt (III) Complex Supported on Carbonaceous Nanomaterials", Journal of Electroanalytical Chemistry, (Jan. 5, 2015), vol. 740, No. 5, 37-44.
Prusty, et al., "A Fluorogenic Reaction Based on Heavy-Atom Removal for Ultrasensitive DNA Detection", Journal of American Chemical Society, (Aug. 16, 2010), 132, 12197-12199.
Prusty, et al., "A Fluorogenic Reaction Based on Heavy-Atom Removal for Ultrasensitive DNA Detection", Journal of American Chemical Society, Supporting Information, (Aug. 16, 2010), 132, S1-S14.
Prusty, et al., "Modular Assembly of a Pd Catalyst within a DNA Scaffold for the Amplified Colorimetric and Fluorimetric Detection of Nucleic Acids", Angewandte Chemie, (2012), 124, 12064-12068.

(Continued)

*Primary Examiner* — Galina Yakovleva

(57) ABSTRACT

Among other things, the present invention provides assay methods for detecting or quantifying one or more analytes in a sample, which involve the use of dissociable nanoparticles that comprise one or more signaling agents (e.g., the nanoparticles conceal or partially conceal the signaling agents).

6 Claims, 21 Drawing Sheets

(56) References Cited

OTHER PUBLICATIONS

Prusty, et al., "Modular Assembly of a Pd Catalyst within a DNA Scaffold for the Amplified Colorimetric and Fluorimetric Detection of Nucleic Acids", Angewandte Chemie, Supporting Information, (2012), 124, S1-S16.
Qu, et al., "Copper-Mediated Amplification Allows Readout of Immunoassays by the Naked Eye", Angewandte Chemie International Editions, (Mar. 8, 2011), vol. 50, No. 15, 3442-3445.
Shu, et al., "DNA Detection Based on Fluorogenic Nanospheres", Angewandte Chemie, (Oct. 29, 2012), vol. 51, No. 44, 11006-11009.
The Molecular Probes® Handbook: A Guide to Fluorescent Probes and Labeling Technologies, 11th Ed., (2010), Chapter 18, 802-828.
Wang, et al., ""Electroactive Beads" for Ultrasensitive DNA Detection", (Feb. 1, 2003), vol. 19, No. 4, Langmuir, 989-991.

\* cited by examiner

ASSAY METHODS INVOLVING DISSOCIABLE NANOPARTICLES

BACKGROUND OF THE INVENTION

Many biochemical assays require labels for detection in order to convert a specific binding event into a measurable signal. Such labels may provide signals that are measurable optically, electrically, acoustically, magnetically, etc. Thus, while the binding of two molecules may be optically undetectable, if one molecule is "labeled" with an optically active species, the molecular binding event may now be detected optically.

In order to enhance the detection sensitivity of in vitro diagnostic assays, an amplification event is often performed. Labels may perform this amplification. For example, catalytic amplification may be performed by enzymes, such as horseradish peroxidase, alkaline phosphatase, etc, that are directly or indirectly bound to biological recognition molecules. Each enzyme catalyst can then produce multiple detectable molecules, resulting in an amplification of each individual biochemical recognition event.

Such enzyme labels are often utilized for signal production and amplification in enzyme immunoassays (EIAs), such as enzyme-linked immunosorbent assays (ELISAs) and enzyme-linked immunospot assays (ELISPOTs), and immunoblot assays (Western blots). Enzymes offer a limited amplification capability, may have high nonspecific binding, and can produce only a single signal, limiting their utility in multiplexed assay formats. Enzyme performance may vary significantly from batch-to-batch, over time, and with non-optimal storage conditions. Furthermore, enzyme conjugates, specifically enzyme-antibody conjugates, are difficult to manufacture, adding the requirement of at least one additional detection step in some assay formats. Existing non-enzymatic amplification strategies suffer from low amplification levels, high non-specific and off-target binding, and/or the use of non-standard equipment, limiting their performance and utility.

SUMMARY OF THE INVENTION

The present invention provides a novel approach that offers significant advances over enzyme and existing non-enzyme labels based detection methods. The invention is based, at least in part, on the design of labels in dissociable nanoparticle form that conceal their payloads until the onset of a specific trigger. The trigger releases the payloads, which result in a detectable signal that can be measured with standard hardware. Nanoparticle labels may be designed to associate with various detection agents, such as antibodies, for specific binding to analytes of interest. This design enables the recognition binding events to be isolated from the production of the measurable signal, which provides unprecedented capacity for improving signal amplification, detection specificity, assay sensitivity and multiplexity. For example, nanoparticle labels may be designed to increase the amplification, which allows much greater detection sensitivities. Nanoparticle labels also offer improved stability, decreased non-specific binding, and may also be designed to release signals that may be detected differently, improving the ease of multiplexing and increasing dynamic range. Thus, the present invention represents a significant breakthrough in the field of biochemical assays.

Thus, in one aspect, the present invention provides a method of detecting an analyte, comprising (i) incubating a sample suspected of having an analyte of interest with a binding agent specific to the analyte under conditions that permit binding between the analyte and the binding agent; wherein the binding agent is associated with a nanoparticle comprising a signaling agent; (ii) dissociating the nanoparticle bound to the analyte, if any, to release the signaling agent such that it results in a signal change; and (iii) determining presence or quantity of the analyte in the sample based on the signal change. In some embodiments, the signaling agent is not an enzyme. In some embodiments, if the signaling agent is a pre-chemiluminophore, the nanoparticle is not crystalline. In some embodiments, the binding agent is associated with the nanoparticle via an interaction other than an electrostatic interaction.

In some embodiments, the signal change is an optical signal change. In certain embodiments, the optical signal change is a change in absorbance, fluorescence, and/or luminescence.

In some embodiments, the nanoparticle comprises a liquid phase. In some embodiments, the nanoparticle is a liposome. In some embodiments, the nanoparticle is liquid free.

In some embodiments, the nanoparticle further comprises one or more matrix-forming agents providing a matrix. In some embodiments, the signaling agent is embedded in the matrix. In some embodiments, the nanoparticle comprises a core formed by the signaling agent encapsulated by the matrix. In some embodiments, the one or more matrix-forming agents comprise one or more polymers, waxes, fats, oils, surfactants, lipid esters or amides, or a combination thereof.

In some embodiments, the signaling agent is a catalyst, a chemiluminophore, an absorber, and/or a precursor thereof. In particular embodiments, the signaling agent is a catalyst or a precursor thereof. In certain embodiments, the catalyst or the precursor thereof comprises a metal. In some embodiments, the metal is an alkali metal, an alkaline earth metal, a lanthanide, an actinide, or a transition metal. In some embodiments, the metal is a transition metal.

In some embodiments, the catalyst or the precursor thereof is selected from a metal, a metal ion, a metal oxide, or a metalorganic species. In some embodiments, the catalyst or the precursor thereof is a metalorganic species. In some embodiments, the metalorganic species comprises a metal-tetraamidomacrocyclic ligand complex.

In some embodiments, the catalyst or the precursor thereof comprises a metal or metal ion selected from: Fe(II), Fe(III), Cu(I), Cu(II), Pd(0), Pd(II), or a combination thereof.

In some embodiments, the catalyst or the precursor is selected from the group consisting of iron oxide, cerium oxide, titanium dioxide, palladium on carbon, or a combination thereof.

In some embodiments, the signaling agent is a chemiluminophore or a precursor thereof. In some embodiments, the chemiluminophore or the precursor thereof comprises fluorescein dilaurate, rhodamine octadecyl ester, or rhodamine hexyl ester.

In some embodiments, the signaling agent is an absorber or a precursor thereof. In some embodiments, the absorber or the precursor thereof is selected from the group consisting of 3,3',5,5'-tetramethylbenzidine and/or 2,2'-azino-bis(3-ethylbenzothiazoline-6-sulphonic acid).

In some embodiments, the nanoparticle comprises at least two different signaling agents. In some embodiments, the at least two different signaling agents comprise a catalyst and a chemiluminophore, or precursors thereof. In some embodiments, the at least two different signaling agents comprise a catalyst and an absorber, or precursors thereof.

In some embodiments, the binding agent is selected from antibody, antigen, enzyme, fibronectin, oligonucleotide, oligopeptide, oligosaccharide, nucleic acid, nucleotide, nucleoside, metabolite, lipid, fatty acid, glycolipid, sterol, glycerolipid, vitamin, hormone, neurotransmitter, DNA, RNA, including mRNA, rRNA, microRNA, small interfering RNA (siRNA), long noncoding RNA (lnc RNA), small nuclear RNA (snRNA), double stranded RNA (ds RNA) peptide nucleic acid (PNA), polymer nucleic acid, locked nucleic acid (LNA), cDNA, amino acid, protein, peptide, polypeptide, receptor, ligand, small molecule, aptamers, polysaccharides, plastibodies, other member of receptor-ligand pair, affibody, plastibody, camelid, or a combination thereof.

In some embodiments, the binding agent is an antibody or antigen-binding fragment thereof. In certain embodiments, the antibody or antigen-binding fragment thereof is a primary antibody. In certain embodiments, the antibody or antigen-binding fragment thereof is a secondary antibody.

In some embodiments, the binding agent is a small molecule.

In some embodiments, the binding agent is associated with the nanoparticle via covalent conjugation, non-covalent interaction, and/or adsorption. In certain embodiments, the binding agent is associated with the nanoparticle via covalent conjugation.

In some embodiments, the nanoparticle comprises one or more functional groups for conjugating the nanoparticle to the binding agent. In some embodiments, the one or more functional groups are selected from an amino group, an azido group, a thiol group, an alkenyl group, an alkynyl group, a carboxylic acid group, a carboxylic ester group, an N-hydroxysuccinimidyl ester group, an isothiocyanate group, an isocyanide group, a maleimide group, an aldehyde group, a norbornyl group, a cyclooctenyl group, and/or a tetrazine group. In certain embodiments, the one or more functional groups are linked to an outer surface. In certain embodiments, the functional group is linked to the outer surface via polyethylene glycol (PEG).

In some embodiments, the nanoparticle further comprises an impermeable layer underneath the outer surface. In some embodiments, the impermeable layer blocks diffusion of the signaling agent from the nanoparticle prior to dissociation.

In some embodiments, the dissociating step comprises treating the nanoparticle with a physical trigger, a chemical trigger, or a combination thereof. In certain embodiments, the physical trigger is selected from the group consisting of thermal energy, electromagnetic energy, and/or sound energy. In certain embodiments, the chemical trigger is an enzyme, a catalyst, a solvent, or an acid or base or other chemical agent, or a combination thereof.

In some embodiments, the signaling agent is a catalyst and wherein step (ii) is performed by contacting the catalyst with a substrate under conditions that permit the conversion of the substrate to a product in the presence of the catalyst, thereby resulting in the signal change. In certain embodiments, the product gives rise to a detectable signal. In certain embodiments, the substrate gives rise to a detectable signal and conversion of the substrate to the product leads to attenuation of the signal.

In some embodiments, the catalyst is a reactive oxygen species generator and the substrate is a redox-reactive chemiluminophore or a redox-reactive absorber.

In some embodiments, the substrate is selected from the group consisting of: dihydrorhodamine 123, 10-acetyl-3,7-dihydroxyphenoxazine, 3,3',5,5'-tetramethylbenzidine, 2,2'-azino-bis(3-ethylbenzothiazoline-6-sulphonic acid), resazurin, coumarin-3-carboxylic acid, fluorescein, methyl orange, terepthalic acid, sodium terepthalate, 2-[6-(4'-hydroxy)phenoxy-3H-xanthen-3-on-9-yl]benzoic acid, 2-[6-(4'-amino)phenoxy-3H-xanthen-3-on-9-yl]benzoic acid, fluorescein, 2',7'-dichlorofluorescein, 2,7-dichlorodihydrofluorescein, hydroethidine, 1,3-diphenylisobenzofuran, 2-(2-pyridil)-benzothiazoline, 4-(9-anthroyloxy)-2,2,6,6-tetramethylpiperidine-1-oxyl, 1,3-cyclohexanedione, coumarin-3-carboxylic acid NHS ester, cis-parinaric acid, 4,4-difluoro-5-(4-phenyl-1,3-butadienyl)-4-bora-3a,4a-diaza-s-indacene-3-undecanoic acid), dipyridamole, diphenyl-1-pyrenylphosphine, 2,7-dichlorodihydrofluorescein diacetate, TEMPO, 9-anthraldehyde, and nitrophenol.

In some embodiments, the catalyst is a singlet oxygen generator and wherein the substrate is a singlet oxygen-reactive chemiluminophore or absorber.

In some embodiments, the substrate is 9,10-dimethylanthracene, 1,3-diphenylisobenzofuran, 9-[2-(3-carboxy-9,10-dimethyl)anthryl]-6-hydroxy-3H-xanthen-3-one, or 9-[2-(3-carboxy-9,10-diphenyl)anthryl]-6-hydroxy-3H-xanthen-3-one.

In some embodiments, the catalyst is an ion of Cu and the substrate is a substrate of a Huisgen cycloaddition reaction.

In some embodiments, the substrate is a 3-azido coumarin derivative, 4-azido or 4-alkynyl-1,8-napthalimide.

In some embodiments, the catalyst is Pd or an ion of Pd or Pt or a metalorganic complex comprising Pd or Pt and the substrate is a substrate of a pi-allyl or dehalogenation reaction.

In some embodiments, the substrate is an allylated or propargylated fluorescein derivative or a halogenated boron-dipyrromethene derivative.

In some embodiments, the signaling agent is a chemiluminophore or an absorber, and wherein step (ii) is performed by electromagnetic excitation. In certain embodiments, the chemiluminophore or the absorber is selected from the group of consisting of fluorescein, rhodamine, resorufin, AlexaFluor, BODIPY, Cy, Dansyl, SYTO, chloro-9,10-diphenylanthracene, chloro-9,10-bis(phenylethynyl)anthracene, dichloro-9,10-bis(phenylethynyl)anthracene, rubrene, 5,12-bis(phenylethynyl)naphthacene, or a derivative thereof. In certain embodiments, the signaling agent is a precursor of a chemiluminophore or absorber and further wherein step (ii) is performed by converting the precursor of chemiluminophore or absorber to the chemiluminophore or absorber that gives rise to a detectable signal. In certain embodiments, step (ii) is performed in a solution comprising an oxidizing and/or reducing agent.

In some embodiments, the oxidizing and/or reducing agent is selected from the group consisting of hydrogen peroxide, hypochlorous acid, sodium hypochlorite, sodium borohydride, hydrogen sulfide, dithianes, thiols, glutathione, acetylcysteine, sodium percarbonate, calcium percarbonate, citric acid, 3,3',3''-phosphanetriyltripropanoic acid, ozone, Hg(II), Cu(II), Cu(I), and Co(II).

In some embodiments, the signaling agent is a pre-chemiluminophore that is an ion or organic molecule and step (ii) is performed in the presence of an ionic or organic pre-chemiluminophore, wherein the ion and the organic precursor form a complex, which gives rise to a detectable signal. In certain embodiments, the organic precursor is 8-hydroxyquinoline, 8-hydroxyquinoline-5-sulfonic acid, 2-(((pyridin-2-ylmethyl)imino)methyl)phenol, 9-acridone-4-carboxylic acid, or L-lysine. In certain embodiments, step (ii) and step (iii) are performed simultaneously in a solution. In certain embodiments, the solution further comprises a chemical trigger for dissociating the nanoparticle. In certain embodiments, the solution further comprises a pH modulator, a solvent, a catalyst, a co-catalyst, or a combination thereof.

In some embodiments, the signaling agent is a molecular intercalator, which increases fluorescence upon intercalation with a binding partner thereof. In some embodiments, the molecular intercalator is selected from the group consisting of Ethidium bromide, POPO-3 iodide, SYBR Gold, SYBR Green I, SYBR Green II, TO-PRO-1 iodide, TO-PRO-3 iodide, TOTO-1 iodide, TOTO-3 iodide, YO-PRO-1 iodide, YOYO-1 iodide, Quant-iT PicoGreen, Quant-iT OliGreen, Quant-iT RiboGreen, SYTOX Blue, SYTOX Green, SYTOX Orange, SYTOX Red, POPO-1, BOBO-1, YOYO-1, TOTO-1, JOJO-1, POPO-3, LOLO-1, BOBO-3, YOYO-3, TOTO-3, PO-PRO-1, YO-PRO-1, JO-PRO-1, PO-PRO-1, YO-PRO-3, TO-PRO-3, and TO-PRO-S. In some embodiments, the binding partner of the molecular intercalator is a nucleic acid. In some embodiments, step (ii) is performed in a solution to allow the molecular intercalator to interact with the binding partner.

In some embodiments, the sample is a biological sample. In certain embodiments, the biological sample is selected from cells, cell lysate, FFPE (FASP Protein Digestion) digests, tissues including tissue biopsies or autopsysamples, whole blood, plasma, serum, urine, stool, saliva, cerebrospinal fluid, cord blood, chorionic villus samples amniotic fluid, and transcervical lavage fluid.

In another aspect, the present invention provides a kit comprises reagents to perform various described herein. In some embodiments, a kit for detecting an analyte comprises (i) a binding agent specific to the analyte, wherein the binding agent is associated with a nanoparticle comprising a signaling agent; and (ii) a solution comprising reagents for performing a reaction that results in a signal change, once the signaling agent is released from the nanoparticle. In some embodiments, the signaling agent is not an enzyme. In some embodiments, if the signaling agent is a pre-chemiluminophore, the nanoparticle is not crystalline. In some embodiments, the binding agent is associated with the nanoparticle via an interaction other than an electrostatic interaction.

In some embodiments, the signaling agent is a catalyst, a chemiluminophore, an absorber, and/or a precursor thereof. In some embodiments the signaling agent is a catalyst or a precursor thereof. In some embodiments, the catalyst or the precursor thereof comprises a metal. In some embodiments, the metal is an alkali metal, an alkaline earth metal, a lanthanide, an actinide, or a transition metal. In some embodiments, the metal is a transition metal.

In some embodiments, the catalyst or the precursor thereof is selected from a metal, a metal ion, a metal oxide, or a metalorganic species. In some embodiments, the catalyst or the precursor thereof is a metalorganic species. In some embodiments, the metalorganic species comprises a metal-tetraamidomacrocyclic ligand complex.

In some embodiments, the catalyst or the precursor thereof comprises a metal or metal ion selected from: Fe(II), Fe(III), Cu(I), Cu(II), Pd(0), Pd(II), or a combination thereof.

In some embodiments, the catalyst or the precursor is selected from the group consisting of iron oxide, cerium oxide, titanium dioxide, palladium on carbon, or a combination thereof.

In some embodiments, the signaling agent is a chemiluminophore or a precursor thereof. In some embodiments, the chemiluminophore or the precursor thereof comprises fluorescein dilaurate, rhodamine octadecyl ester, or rhodamine hexyl ester. In some embodiments, the signaling agent is an absorber or a precursor thereof. In some embodiments, the absorber or the precursor thereof selected from the group consisting of 3,3',5,5'-tetramethylbenzidine and/or 2,2'-azino-bis(3-ethylbenzothiazoline-6-sulphonic acid).

In some embodiments, the nanoparticle comprises at least two different signaling agents. In some embodiments, the at least two different signaling agents comprise a catalyst and a chemiluminophore, or precursors thereof. In some embodiments, the at least two different signaling agents comprise a catalyst and an absorber, or precursors thereof.

In some embodiments, the binding agent is selected from antibody, antigen, enzyme, fibronectin, oligonucleotide, oligopeptide, oligosaccharide, nucleic acid, nucleotide, nucleoside, metabolite, lipid, fatty acid, glycolipid, sterol, glycerolipid, vitamin, hormone, neurotransmitter, DNA, RNA, including mRNA, rRNA, microRNA, small interfering RNA (siRNA), long noncoding RNA (lnc RNA), small nuclear RNA (snRNA), double stranded RNA (ds RNA) peptide nucleic acid (PNA), polymer nucleic acid, locked nucleic acid (LNA), cDNA, amino acid, protein, peptide, polypeptide, receptor, ligand, small molecule, aptamers, polysaccharides, plastibodies, other member of receptor-ligand pair, affibody, plastibody, camelid, or a combination thereof.

In some embodiments, the binding agent is an antibody or antigen-binding fragment thereof. In certain embodiments, the antibody or antigen-binding fragment thereof is a primary antibody. In certain embodiments, the antibody or antigen-binding fragment thereof is a secondary antibody.

In some embodiments, the binding agent is a small molecule.

In some embodiments, the kit comprises a physical trigger, a chemical trigger, or a combination thereof, for dissociating the nanaoparticle. In certain embodiments, the physical trigger is selected from the group consisting of thermal energy, electromagnetic energy, and/or sound energy. In certain embodiments, the chemical trigger is an enzyme, a catalyst, a solvent, an acid or base or other chemical agent, or a combination thereof.

In some embodiments, the solution comprises the chemical trigger.

In some embodiments, the signaling agent is a catalyst and wherein the solution comprises a substrate of the catalyst.

In some embodiments, the catalyst is a reactive oxygen species generator and wherein the substrate is a redox-reactive chemiluminophore or a redox-reactive absorber. In certain embodiments, the substrate is selected from the group consisting of: dihydrorhodamine 123, 10-acetyl-3,7-dihydroxyphenoxazine, 3,3',5,5'-tetramethylbenzidine, 2,2'-azino-bis(3-ethylbenzothiazoline-6-sulphonic acid), resazurin, coumarin-3-carboxylic acid, fluorescein, methyl orange, terepthalic acid, sodium terepthalate, 2-[6-(4'-hydroxy)phenoxy-3H-xanthen-3-on-9-yl]benzoic acid, 2-[6-(4'-amino)phenoxy-3H-xanthen-3-on-9-yl]benzoic acid, fluorescein, 2',7'-dichlorofluorescein, 2,7-dichlorodihydrofluorescein, hydroethidine, 1,3-diphenylisobenzofuran, 2-(2-pyridil)-benzothiazoline, 4-(9-anthroyloxy)-2,2,6,6-tetramethylpiperidine-1-oxyl, 1,3-cyclohexanedione, coumarin-3-carboxylic acid NHS ester, cis-parinaric acid, 4,4-difluoro-5-(4-phenyl-1,3-butadienyl)-4-bora-3a,4a-diaza-s-indacene-3-undecanoic acid), dipyridamole, diphenyl-1-pyrenylphosphine, 2,7-dichlorodihydrofluorescein diacetate, TEMPO, 9-anthraldehyde, and nitrophenol.

In some embodiments, the catalyst is a singlet oxygen generator and wherein the substrate is a singlet oxygen-reactive chemiluminophore or absorber. In certain embodiments, the substrate is 9,10-dimethylanthracene, 1,3-diphenylisobenzofuran, 9-[2-(3-carboxy-9,10-dimethyl)anthryl]-6-hydroxy-3H-xanthen-3-one, or 9-[2-(3-carboxy-9,10-diphenyl)anthryl]-6-hydroxy-3H-xanthen-3-one.

In some embodiments, the catalyst is an ion of Cu and the substrate is a substrate of a Huisgen cycloaddition reaction.

In some embodiments, the substrate is a 3-azido coumarin derivative, 4-azido or 4-alkynyl-1,8-napthalimide.

In some embodiments, the catalyst is Pd or an ion or metalorganic complex of Pd or Pt and the substrate is a substrate of a pi-allyl or dehalogenation reaction.

In some embodiments, the substrate is an allylated or propargylated fluorescein derivative or a halogenated borondipyrromethene derivative.

In some embodiments, the kit further comprises a reagent for stopping the reaction.

In some embodiments, the signaling agent is a chemiluminophore or an absorber. In certain embodiments, the chemiluminophore or the absorber is selected from the group of consisting of fluorescein, rhodamine, rhodamine octadecyl ester, resorufin, AlexaFluor, BODIPY, Cy, Dansyl, SYTO, chloro-9,10-diphenylanthracene, chloro-9,10-bis(phenylethynyl)anthracene, dichloro-9,10-bis(phenylethynyl)anthracene, rubrene, 5,12-bis(phenylethynyl)naphthacene, or a derivative thereof.

In some embodiments, the signaling agent is a precursor of a chemiluminophore or absorber.

In some embodiments, the solution comprising an oxidizing and/or reducing agent. In certain embodiments, the oxidizing and/or reducing agent is selected from the group consisting of hydrogen peroxide, hypochlorous acid, sodium hypochlorite, sodium borohydride, hydrogen sulfide, dithianes, thiols, glutathione, acetylcysteine, sodium percarbonate, calcium percarbonate, citric acid, 3,3',3"-phosphanetriyltripropanoic acid, ozone, Hg(II), Cu(II), Cu(I), and Co(II).

In some embodiments, the signaling agent is a pre-chemiluminophore that is an ion or organic molecule.

In some embodiments, the organic precursor is 8-hydroxyquinoline, 8-hydroxyquinoline-5-sulfonic acid, 2-(((pyridin-2-ylmethyl)imino)methyl)phenol, 9-acridone-4-carboxylic acid, or L-lysine.

In some embodiments, the solution further comprises a pH modulator, a solvent, a catalyst, a co-catalyst, or a combination thereof.

In some embodiments, the signaling agent is a molecular intercalator. In certain embodiments, the molecular intercalator is selected from the group consisting of Ethidium bromide, POPO-3 iodide, SYBR Gold, SYBR Green I, SYBR Green II, TO-PRO-1 iodide, TO-PRO-3 iodide, TOTO-1 iodide, TOTO-3 iodide, YO-PRO-1 iodide, YOYO-1 iodide, Quant-iT PicoGreen, Quant-iT OliGreen, Quant-iT RiboGreen, SYTOX Blue, SYTOX Green, SYTOX Orange, SYTOX Red, POPO-1, BOBO-1, YOYO-1, TOTO-1, JOJO-1, POPO-3, LOLO-1, BOBO-3, YOYO-3, TOTO-3, PO-PRO-1, YO-PRO-1, JO-PRO-1, PO-PRO-1, YO-PRO-3, TO-PRO-3, and TO-PRO-S. In certain embodiments, the solution comprises a binding partner of the molecular intercalator.

In some embodiments, the binding partner is a nucleic acid.

In some embodiments, the kit further comprises one or more controls for determining the signal change and/or the presence or quantity of the analyte in the sample.

In some embodiments, the kit further comprises an instruction for performing the reaction.

Another aspect of the present disclosure features a method for detecting an analyte, the method comprising: (i) incubating a sample suspected of having a first analyte with a first binding agent specific to the first analyte to form a first mixture, wherein the first binding agent is conjugated to a nanoparticle comprising a first signaling agent, wherein the first signaling agent is not an enzyme if the nanoparticle contains a liquid phase; and wherein optionally the nanoparticle is free of a liquid phase; (ii) removing from the first mixture the first binding agent that is not bound to the first analyte to form a second mixture; (iii) dissociating the nanoparticle in the second mixture, if any, to release the first signaling agent into a solution, wherein the first signaling agent is soluble in the solution; (iv) subjecting the first signaling agent to a reaction, which results in a signal change; and (v) determining presence or quantity of the first analyte in the sample based on the signal change. In some embodiments, the method further comprises, prior to step (i), incubating the sample with a second binding agent specific to the first analyte, wherein the second binding agent is immobilized on a solid support.

In another aspect, the present disclosure provides a method for detecting an analyte, comprising: (i) incubating a solid support on which a first analyte is immobilized with a first conjugate to form a first mixture, the solid support optionally including a macroscale surface, a micro-, submicro-, or nanoparticle or a porous membrane, wherein the first conjugate comprises a first binding agent specific to the first analyte and a first nanoparticle that comprises a first signaling agent, wherein the first signaling agent is not an enzyme if the first nanoparticle contains a liquid phase, and optionally wherein the first nanoparticle is free of a liquid phase; (ii) removing from the first mixture unbound first conjugate to form a second mixture; (iii) dissociating the first nanoparticle in the first conjugate to release the first signaling agent into a solution, wherein the first signaling agent is soluble in the solution; (iv) subjecting the first signaling agent to a reaction, which results in a signal change; and (v) determining presence or quantity of the first analyte in the sample based on the signal change.

In some embodiments, the method may further comprise, prior to step (i), incubating the solid support with a sample suspected of containing the first analyte to allow for immobilization of the first analyte onto the solid support. In some examples, step (i) is performed in the presence of the first binding agent in free form. Alternatively, the method may further comprise, prior to step (i), incubating a sample suspected of having the first analyte with the first conjugate.

In any of the methods described herein, the first binding agent and/or the second binding agent can be an antibody, antigen, enzyme, fibronectin, oligonucleotide, oligopeptide, oligosaccharide, nucleic acid, nucleotide, nucleoside, metabolite, lipid, fatty acid, glycolipid, sterol, glycerolipid, vitamin, hormone, neurotransmitter, DNA, RNA, including mRNA, rRNA, microRNA, small interfering RNA (siRNA), long noncoding RNA (lnc RNA), small nuclear RNA (snRNA), double stranded RNA (ds RNA) peptide nucleic acid (PNA), polymer nucleic acid, locked nucleic acid (LNA), cDNA, amino acid, protein, peptide, polypeptide, receptor, ligand, small molecule, aptamers, polysaccharides, plastibodies, other member of receptor-ligand pair, affibody, plastibody, camelid, or any selective detection materials disclosed herein. In some examples, the first binding agent and the second binding agent are antibodies binding to the analyte, and wherein the first and second binding agents bind to different epitopes of the analyte. In some embodiments the first binding agent is an antibody and the second binding agent is a small molecule; in some embodiments the first binding agent is a small molecule and the second binding agent is an antibody.

In some embodiments, the nanoparticle used in any of the methods described herein may comprise one or more polymers, waxes, fats, oils, surfactants, inorganic materials, lipid esters or amides, or a combination thereof, which form a matrix, and wherein the first signaling agent is embedded in the matrix. In yet other embodiments, the nanoparticle may comprise a core formed by the first signaling agent, which can be a metal, a metal ion, a metal oxide, an organometallic species, a chemiluminophore, a dye, or a precursor thereof.

Any of the nanoparticles described herein may comprise an outer surface that comprises one or more functional groups for conjugating the nanoparticle to the first binding agent. Optionally, it may further comprise an impermeable layer underneath the outer surface, wherein the impermeable layer blocks diffusion of the first signaling agent from the nanoparticle prior to step (iii).

In some embodiments, the releasing step (iii) comprises treating the nanoparticle with a physical trigger, a chemical trigger, or a combination thereof to dissociate the nanoparticle, thereby releasing the first signaling agent into the solution. The physical trigger may be thermal energy (e.g., heat), electromagnetic energy (e.g., UV, visible, IR, microwave), and/or sound energy (e.g., ultrasonic, megasonic). The chemical trigger may be an enzyme, a catalyst, an acid, a base, a solvent, or other chemical compound.

In some embodiments, the nanoparticle is treated with ultrasound and the nanoparticle comprises a core that comprises air or liquid. In other embodiments, the nanoparticle is treated with a physical trigger, which can be heat, light, or a combination thereof, and the nanoparticle further comprises a dopant, which enhances disassociation of the nanoparticle to release the first signaling agent under the physical trigger. Examples of dopant include light-sensitive molecules (e.g., diazoquinones) and thermally-absorbing species (e.g., metallic nanoparticles).

The first signaling agent used in any of the methods described herein can be a catalyst or precursor thereof and step (iv) can be performed by contacting the catalyst or precursor with a substrate, which converts to a product in the presence of the catalyst, wherein the conversion from the substrate to the product results in the signal change. In some examples, the product converted from the substrate releases a detectable signal. In other examples, the substrate releases a detectable signal and conversion of the substrate to the product leads to signal attenuation.

In some embodiments, the catalyst is a reactive oxygen species generator or precursor thereof and step (iv) of the method described herein may be performed in a solution comprising a substrate of the catalyst, which is a redox-reactive fluorophore or a redox-reactive absorber. When applicable, step (iii) and step (iv) can be performed simultaneously in the solution, which may further comprise a chemical trigger for dissociating the nanoparticle to release the catalyst. In some examples, the solution may further comprise an organic solvent; a co-initiator, such as an oxidizing or reducing agent (e.g., hydrogen peroxide, potassium monoperoxysulfate, bis(2,4,5-trichloro-6-carbopentoxyphenyl) oxalate, bis(2,4,6-trichlorophenyl) oxalate, bis (2,4-dinitrophenyl) oxalate); an electron donor and/or acceptor (e.g., glycerol, adenosine triphosphate); an enhancer (e.g., imidazole, pyridine, sodium salicylate, sodium acetate); and/or a combination thereof. Suitable substrates are well known to those skilled in the art and are described in *The Molecular Probes® Handbook: A Guide to Fluorescent Probes and Labeling Technologies*, 11$^{th}$ Ed. (2010) and Gomes, Fernandes, and Lima *J. Biochem. Biophys. Methods* 65 (2005) pp 45-80, which are herein incorporated by reference in their entirety. Examples of suitable substrates include, but are not limited to, dihydrorhodamine 123, 10-acetyl-3,7-dihydroxyphenoxazine, 3,3',5,5'-tetramethylbenzidine, 2,2'-azino-bis(3-ethylbenzothiazoline-6-sulphonic acid), resazurin, coumarin-3-carboxylic acid, fluorescein, methyl orange, terepthalic acid, sodium terepthalate, 2-[6-(4'-hydroxy)phenoxy-3H-xanthen-3-on-9-yl]benzoic acid, 2-[6-(4'-amino)phenoxy-3H-xanthen-3-on-9-yl]benzoic acid, fluorescein, 2',7'-dichlorofluorescein, 2,7-dichlorodihydrofluorescein, hydroethidine, 1,3-diphenylisobenzofuran, 2-(2-pyridil)-benzothiazoline, 4-(9-anthroyloxy)-2,2,6,6-tetramethylpiperidine-1-oxyl, 1,3-cyclohexanedione, coumarin-3-carboxylic acid NHS ester, cis-parinaric acid, 4,4-difluoro-5-(4-phenyl-1,3-butadienyl)-4-bora-3a,4a-diaza-s-indacene-3-undecanoic acid), dipyridamole, diphenyl-1-pyrenylphosphine, 2,7-dichlorodihydrofluorescein diacetate, TEMPO, 9-anthraldehyde, and nitrophenol.

In some embodiments, the catalyst is a singlet oxygen generator and step (iv) of the method described herein may be performed in a solution comprising a substrate of the catalyst, which can be a singlet oxygen-reactive chemiluminophore or absorber, or a photosensitizer. When applicable, step (iii) and step (iv) may be performed simultaneously in the solution, which may further comprise a chemical trigger for dissociating the nanoparticle to release the catalyst. In some examples, the solution may further comprise dissolved oxygen, an organic solvent (e.g., DMSO), or a combination thereof. Exemplary substrates include, but are not limited to, 9,10-dimethylanthracene, 1,3-diphenylisobenzofuran, 9-[2-(3-carboxy-9,10-dimethyl) anthryl]-6-hydroxy-3H-xanthen-3-one, or 9-[2-(3-carboxy-9,10-diphenyl)anthryl]-6-hydroxy-3H-xanthen-3-one.

In yet other embodiments, the catalyst is a metal or metal ion of Fe, Cu, Pd, or Hg, which catalyzes a reaction to convert a substrate to a detectable product and step (iv) of the method described herein may be performed in the solution comprising the substrate. When applicable, step (iii) and step (iv) can be performed simultaneously in the solution. In some examples, the solution may further comprise a chemical trigger for releasing the catalyst from the nanoparticle.

In still other embodiments, the catalyst is an ion of Cu and the substrate is a substrate of a Huisgen cycloaddition reaction. Examples of such substrates include a 3-azido coumarin derivative, 4-azido, or 4-alkynyl-1,8-napthalimide. The solution may further comprise one or more solvents, azide, alkyne, a Cu-reducer, a dye precursor, a reducing agent, or a nucleophile. In other embodiments, the catalyst is an ion of Pt, Pd, or Hg and the substrate of the Tsuji-Trost or Claisen "pi-allyl" reaction is an allylated or propargylated fluorescein derivative.

In other embodiments, the catalyst can be a metalorganic complex (which is a metallic species bound or coordinated to an organic ligand). Examples include iron porphyrins, ruthenium diimines, and iridium-coumarin complexes.

Further, the first signaling agent used in any of the methods described herein can be a precursor of a chemiluminophore and/or absorber. In some examples, step (iv) may be performed by contacting the precursor of the chemiluminophore and/or absorber with a solution having a suitable pH value, such that the precursor of the chemiluminophore and/or absorber converts to the dye that releases a detectable signal. In other examples, step (iv) can be performed by contacting the precursor of a chemiluminophore and/or absorber with an aqueous solution having an oxidizing agent or a reducing agent, which converts the precursor of the chemiluminophore and/or absorber to the chemiluminophore and/or absorber that releases a detectable signal. The oxidizing agent or reducing agent can be hydrogen peroxide, hypochlorous acid, sodium hypochlorite, hydrogen sulfide, dithianes, thiols, glutathione, acetylcysteine, ozone, Hg(II), Cu(II), Cu(I), and Co(II). When applicable, step (iii) and step (iv) can be performed simultaneously in the solution, which may further comprise a chemical trigger for releasing the precursor of a chemiluminophore and/or absorber. Alternatively or in addition, the solution may comprise a pH modulator, a solvent, or a combination thereof.

Alternatively, the first signaling agent of any of the assay methods described herein can be a compound that forms a complex with a binding partner, wherein the complex releases a detectable signal. In some embodiments, the first signaling agent is an ion and step (iv) may be performed in the solution comprising a chemiluminescent or absorbent precursor, wherein the ion and the chemiluminescent or absorbent precursor form a complex that is detectable. In other embodiments, the first signaling agent is a chemiluminescent or absorbent precursor and step (iv) may be performed in the solution comprising a metal ion, wherein the ion and the chemiluminescent or absorbent precursor form a complex that is detectable. The solution may be aqueous or may be a solvent in which the chemiluminescent or absorbent precursor is soluble. Examples of the chemiluminescent or absorbent precursor include 8-hydroxyquinoline, 8-hydroxyquinoline-5-sulfonic acid, 2-(((pyridin-2-ylmethyl)imino)methyl)phenol, 9-acridone-4-carboxylic acid, or L-lysine. When applicable, step (iii) and step (iv) may be performed simultaneously in the solution, which may further comprise a chemical trigger for releasing the precursor of a chemiluminophore and/or absorber, and optionally, an organic co-solvent, a pH modulator, or a combination thereof.

In any of the methods described herein, the first signaling agent may be a molecular intercalator, which produces a detectable signal upon intercalation with a binding partner thereof. Examples of the molecular intercalator include, but are not limited to, ethidium bromide, POPO-3 iodide, SYBR Gold, SYBR Green I, SYBR Green II, TO-PRO-1 iodide, TO-PRO-3 iodide, TOTO-1 iodide, TOTO-3 iodide, YO-PRO-1 iodide, YOYO-1 iodide, Quant-iT PicoGreen, Quant-iT OliGreen, Quant-iT RiboGreen, SYTOX Blue, SYTOX Green, SYTOX Orange, SYTOX Red, POPO-1, BOBO-1, YOYO-1, TOTO-1, JOJO-1, POPO-3, LOLO-1, BOBO-3, YOYO-3, TOTO-3, PO-PRO-1, YO-PRO-1, JO-PRO-1, PO-PRO-1, YO-PRO-3, TO-PRO-3, and TO-PRO-S. In some examples, the binding partner of the molecular intercalator can be a nucleic acid. Step (iv) of the method described herein can be performed in the solution to allow the molecular intercalator to interact with the binding partner, wherein the solution can be aqueous or a solvent in which the molecular intercalator is soluble. When applicable, step (iii) and step (iv) can be performed simultaneously in the solution, which may further comprise a chemical trigger for releasing the intercalator. Alternatively or in addition, the solution may further comprise a pH modulator, an organic solvent, or a combination thereof.

In any of the methods described herein, the first signaling agent may be a dye or chemiluminophore, and step (iv) may be performed by electromagnetic excitation (e.g., light, or radiative or non-radiative intersystem energy transfer, such as Förster resonance energy transfer, or thermal excitation) such that the dye or fluorophore releases a detectable signal. Here it may be the case that no chemical reaction is performed. Examples of the dye or fluorophore include, but are not limited to, fluorescein, rhodamine, resorufin, AlexaFluor, BODIPY, Cy, Dansyl, SYTO, chloro-9,10-diphenylanthracene, chloro-9,10-bis(phenylethynyl)anthracene, dichloro-9,10-bis(phenylethynyl)anthracene, rubrene, and 5,12-bis(phenylethynyl)naphthacene. The solution may further comprise enhancers (e.g. sodium hydroxide, hydrochloric acid, surfactants) and/or energy-generating species (e.g. bis-(3,4,6-trichloro-6-(pentyloxycarbonyl)phenyl)oxalate, bis(2,4,6-trichlorophenyl) oxalate, bis(2,4-dinitrophenyl) oxalate, divanillyl oxalate) and/or oxidizing and/or reducing agents (e.g. hydrogen peroxide, potassium monoperoxysulfate, sodium borohydride, etc.)

In any of the methods described herein, step (iv) is performed within a microparticle or by reagents contained within a microparticle.

In some embodiments, the method described herein may further comprises a second signaling agent, which is different from the first signaling agent. In some examples, the first signaling agent is a catalyst or precursor thereof and the second signaling agent is a chemiluminophore, an absorber, or a precursor thereof. In other examples, the first and second signaling agents are catalysts or precursors thereof or chemiluminophores or absorbers, or precursors thereof.

In any of the methods described herein, the sample is suspected of comprising at least a second analyte and is incubated with both (a) the first nanoparticle to which the first binding agent specific to the first analyte is attached and (b) a second nanoparticle to which a first binding agent specific to the second analyte is attached, the nanoparticle comprising a second signaling agent. Step (iii) of such a method may be performed to dissociate both the first nanoparticle and the second nanoparticle to release both the first signaling agent and the second signaling agent into the solution. Upon a reaction, the first signaling agent and the second signaling agent releases different detectable signals allowing for detection of both the first analyte and the second analyte in the sample. In an alternative embodiment the triggering methods are different for the different nanoparticles.

In yet another aspect, the present disclosure provides a kit for performing any of the methods described herein. The kit may comprise a first conjugate comprising (a) a first binding agent specific to a first analyte, and (b) a first nanoparticle, which comprises a first signaling agent, wherein the first signaling agent is not an enzyme if the first nanoparticle contains a liquid phase; and wherein optionally the nanoparticle is free of a liquid phase; and (ii) a solution comprising components for performing a reaction in the presence of the first signaling agent to produce a product, which results in a signal change. The kit may further comprise a second conjugate comprising (a) a second binding agent specific to a second analyte, and (b) a second nanoparticle, which comprises a second signaling agent, which is different from the first signaling agent, wherein upon reaction, the first signaling agent and the second signaling agent release different detectable signals. The nanoparticle, signaling agent, and binding agent contained in the kit can be any nanoparticle, signaling agent, or binding agent as described herein.

In some embodiments, the kit may further comprise a chemical trigger as described herein for dissociate the nanoparticle(s) to release the signaling agent(s). Such a chemical trigger can be contained in the solution. In some examples, the solution is encapsulated by a microparticle.

In some embodiments, the kit may further comprise a solid support. In some examples, a second binding agent specific to the first analyte is immobilized, and optionally, a second binding agent specific to the second analyte is also immobilized on the solid support. Alternatively, the analyte(s) is immobilized on the solid support.

In some embodiments, the kit may further comprise one or more of an enhancer and/or an energy generator and/or an electron donor and/or acceptor in a homogeneous or heterogeneous phase.

As used in this application, the terms "about" and "approximately" are used as equivalents. Any numerals used in this application with or without about/approximately are meant to cover any normal fluctuations appreciated by one of ordinary skill in the relevant art.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are for illustration purposes only, not for limitation.

FIG. 12A: payloads embedded in polymer matrixes. FIG. 12B: nanoparticles in core-shell format comprising heterogeneous distributed payloads. FIG. 12C: nanoparticles in core-shell format comprising homogeneously distributed payloads. FIG. 12D: nanoparticles comprising antibodies on the surface as binding agents and having payloads entrapped.

FIG. 13A: one tier amplification, such as that embodied by signaling agents comprising chemiluminophores and absorbers and precursors thereof. Note a stoichiometric reaction, binding event, intercalation event, or similar event may be required to produce the measurable signal. FIG. 13B: two-tier amplification, such as that embodied by signaling agents comprising catalysts and precursors thereof.

DETAILED DESCRIPTION OF THE INVENTION

Figure 1:
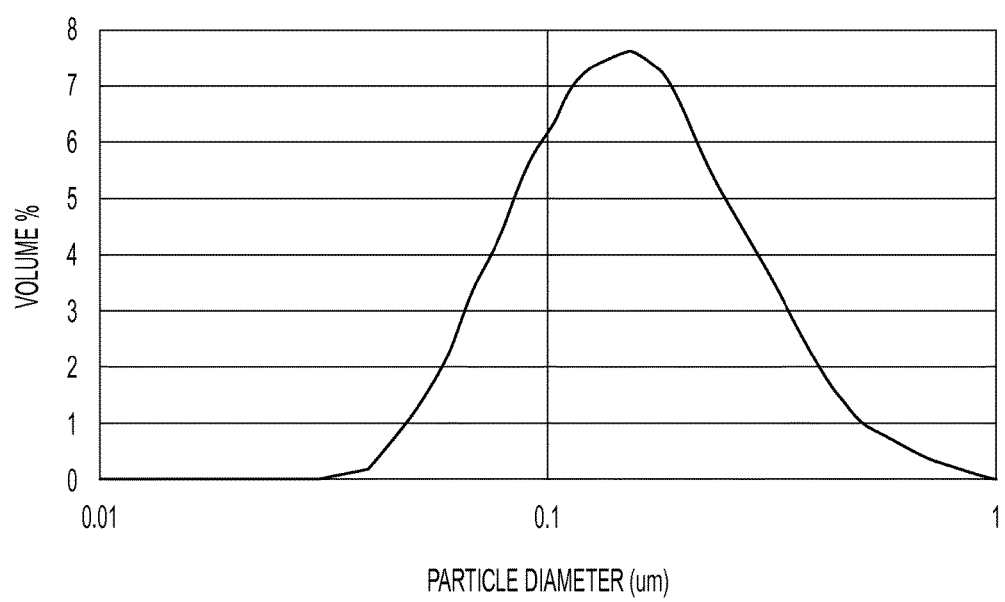
FIG. 1 shows nanoparticles characterized by dynamic light scattering (DLS) as measured with a Malvern Zeta-Sizer. The light scattering shows a mean particle size of 153 nm with a polydispersity index (PDI) of 0.18.

Among other things, the present invention provides assay methods for detecting or quantifying one or more analytes in a sample, which involve the use of nanoparticles that comprise one or more signaling agents (e.g., the nanoparticles conceal or partially conceal the signaling agents). In some embodiments, each nanoparticle is associated with a binding agent specific to an analyte of interest. Subsequent to binding to the analyte, the nanoparticle can be dissociated by a physical or chemical trigger to release the signaling agent into, for example, a suitable solution for a reaction leading to a signal change (e.g., increase a signal or reduce a signal). The solution can be a pure solvent, or a mixture of one or more solvents and one or more additional chemical species. The presence or quantity of the analyte of interest can be determined based on the signal change.

Various aspects of the invention are described in further detail in the following subsections. The use of subsections is not meant to limit the invention. Each subsection may apply to any aspect of the invention. In this application, the use of "or" means "and/or" unless stated otherwise.

Nanoparticles

Various nanoparticles may be used to practice the present invention. In particular, nanoparticles for use in any of the assay methods described herein can be made of a suitable material such that the nanoparticles can be dissociated under a physical or chemical trigger. In some embodiments, a suitable nanoparticle is not crystalline. A nanoparticle as used herein can be a particle of any shape and size. In some embodiments, a nanoparticle suitable for the present invention has a longest-axis feature size that is a maximum of 5 microns (e.g., less than 4 microns, 3 microns, 2 microns, 1 microns, 800 nm, 500 nm, 200 nm, 100 nm, or 50 nm).

In some embodiments, the nanoparticle described herein is in a single phase format which comprises a matrix and a functional surface. The matrix can be made of any suitable material(s) as known in the art or disclosed herein. In some embodiments, the matrix is complexed with a signaling agent. For example, the matrix is used to embed, load, entrap or encapsulate a signaling agent as described herein. In yet other embodiments, the matrix may be made of a material that can also serve as a signaling agent as described herein. Examples of signaling agent include a metal, metal ion, a metal oxide, a metalorganic agent, a chemiluminophore, an absorber, and/or a precursor thereof. Signaling agents are described in detail below.

The functional surface is typically for associating with a binding agent specific to an analyte of interest. The suitable trigger for dissociating a particular nanoparticle would depend on the materials used for making the nanoparticle, which is within the knowledge of a person skilled in the art. Suitable trigger includes, but is not limited to, physical trigger, a chemical trigger, or a combination thereof.

A. Matrix

The term "matrix" refers to a core structure formed from one or more matrix-forming agents. In particular, the signaling agent can be embedded or entrapped in the matrix of the nanoparticle. Alternatively, the nanoparticle may be in a core-shell format, in which the signaling agent is encapsulated. Matrix-forming agents include polymers, waxes, surfactants, and/or lipids.

In some embodiments, the matrix can comprise natural and/or synthetic waxes, e.g., carnauba, beeswax, paraffin, microcrystalline, candle, siliconyl, Kester wax, candelilla, jojoba wax, or rice bran wax.

Alternatively or in addition, the matrix may comprise fatty alcohols and/or fatty acids: cetyl alcohol, palmitoyl alcohol, stearyl alcohol, nonadecyl alcohol, heptadecyl alcohol, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, linolenic acid, stearidonic acid, linoleic acid, palmitoleic acid, oleic acid, lipid ester or amide, or a combination thereof.

In other embodiments, the matrix may comprise polymers such as nondegradable polymers (e.g., polystyrene, novolac, poly vinyl acetate, poly methyl methacrylate, poly vinyl pyrrole, poly vinyl acetate, polyisoprene, polybutadiene) and/or degradable polymers. In some embodiments, the degradable polymer is poly(lactide), poly(glycolide), poly-ε-caprolactone, poly(orthoesters), poly(caprolactones), polylysine, poly(ethylene imine), poly(acrylic acid), poly (urethanes), poly(anhydrides), poly(esters), poly(trimethylene carbonate), poly(ethyleneimine), poly(acrylic acid), poly(urethane), poly(beta amino esters), or is a copolymer thereof (e.g., poly(lactide-co-glycolide) (PLGA)).

In some embodiments, the matrix may comprise one or more inorganic compounds, which can also act as signaling agents. Example inorganic compounds for use in the present disclosure as matrix-forming agents and/or catalysts include, but are not limited to metals (e.g., Al, Pd) and metal oxides (e.g., iron oxide, cerium oxide, titanium dioxide). In other embodiments, a signaling agent or a further signaling agent can be embedded in the matrix formed by the inorganic compounds.

In some embodiments, the matrix may further comprise a dopant. A dopant is a trace element inserted into a substance in order to alter the chemical, thermal, optical, magnetic, and/or electrical properties of the substance. In the presence disclosure, a dopant is used to enhance the disassociation of the nanoparticles to release the signaling agent contained therein under a trigger, such as a physical trigger. The dopant may be a light-sensitive molecule, which is known in the art. Examples include diazonaphthoquinone (DNQ) and its derivatives, for example, esters of DNQ (as known in the area of photoresists). The dopant may also be a thermally-absorbing species, such as metallic nanoparticles, e.g., gold, silver, aluminum, nickel.

Any of the matrices described herein may also comprise one or more surfactants, including, but not limited to, Brijs, Spans, Tweens, Tritons, Igepals, Pluoronics, Poloxamers, lecithin, glyceryl monostearate, glyceryl monooleate, glyceryl monothioglycolate, glyceryl monocaprylate, glyceryl monolaurate, or a combination thereof.

In other embodiments, the core structure is formed from a signaling agent (e.g., a chemiluminophore or an absorber, or a precursor thereof; see, e.g., the chemiluminophores and absorbers, and precursors thereof, described herein).

B. Capping Layer

For example, any of the matrices described herein containing one or more signaling agents may be coated with a layer (a capping layer), which can be made of the same polymer material(s) as the matrix. In other embodiments, the capping layer is not a polyelectrolyte. In further embodiments, the capping layer comprises polyethylene glycol. In further embodiments, the capping layer comprises dextran. The outer functional surface as described herein is added on top of the capping layer. Such a nanoparticle may further comprise one or more stabilizing layer as described herein between the capping layer and the outer surface. In certain embodiments, the stabilizing layer is not a polyelectrolyte.

C. Liposomes

In some embodiments, the nanoparticle may be in a liposome format, which comprises an outside lipid membrane encapsulating a signaling agent (e.g., a non-enzyme or non-protein molecule). In some examples, the nanoparticle is free of any liquid phase (e.g., solid nanoparticles). In other examples, the nanoparticle may comprise a hollow core that contains air or liquid. Such a nanoparticle may be dissociated by ultrasound.

D. Signaling Agents

As used herein, the terms "signaling agent", "signal inducing agent", "signal generating agent", and grammatical equivalents, can be used interchangeably and each refers to a compound that induces, generates, or gives rise to a signal when subjected to a physical or chemical reaction, including events that involve binding or solvation. A signaling agent can be a catalyst, which catalyzes a chemical reaction to convert a substrate to a product that releases a detectable signal or to convert a substrate that releases a detectable signal to a product so as to diminish the detectable signal, or a precursor thereof. A signaling agent can also be a precursor of an absorber or chemiluminophore, which converts to the absorber or chemiluminophore when subjected to a suitable reaction (e.g., oxidation, reduction, hydrolysis reactions). Further, a signaling agent can be a molecule or compound (e.g., a metal ion or organic compound) that forms a complex with a binding partner, wherein the complex releases a detectable signal. Such a molecule can be a molecular intercalator. Alternatively, the signaling agent can be an absorber or a chemiluminophore, such as a fluorophore, which produces a detectable signal upon light excitation. The chemiluminophore may also produce a detectable signal upon non-radiative energy transfer. In another example, the signaling agent can be a nucleic acid, such as a single-stranded or double-stranded DNA molecule, an RNA molecule, or a PNA molecule.

The signaling agent may either directly or indirectly produce a measurable signal. Examples of the signaling agent that produce direct signals are optically active molecules, including absorbers, chemiluminophores, photosensitizers, polymers, and other species that may alter optical absorbance; electrically active molecules (e.g., ions, charged or uncharged species, metallic species, and other species that may alter an electrical field, resistance, dielectric constant), magnetically active molecules and/or compounds (e.g., those that can alter magnetic susceptibility and/or possess a magnetic dipole moment that can be detected with a Hall sensor), and/or acoustically active molecules (e.g., those that can alter surface acoustic wave propagation). Additional examples are provided below.

Catalyst

A catalyst for use in the present disclosure is a substance that increases the rate of a chemical reaction without itself undergoing any permanent chemical change, so as to convert a suitable substrate to a product, wherein the conversion results in a signal change. In some instances, the conversion leads to presence of increase of a detectable signal, e.g., the product releases a signal while the substrate does not. In other cases, the conversion leads to the decrease or reduction of a signal, e.g., the substrate releases a signal while the product does not.

In some embodiments, the catalyst comprises a metal (e.g., the catalyst is a metal, a metal oxide, an organometallic complex). For example, the catalyst can be iron oxide, cerium oxide, titanium dioxide, platinum). In other examples, the catalyst may be a metalorganix complex, which is a metallic species bound or coordinated to an organic ligand. Examples include iron porphyins, ruthenium diimines, iridium-coumarin complexes, iridium-coumarin complexes, bis(1,2-ethanediamine)copper, nickel porphyrin, and/or calcium ethylenediamine tetraacetate.

In some embodiments, the matrix sequesters the catalyst until said matrix is dissociated (e.g., the matrix is dissociated to release the catalyst into solution). In further embodiments, the transition-metal catalyst is embedded in the matrix without being primarily governed by electrostatic interactions (e.g., the catalyst is embedded in the matrix via van der Waals interactions or other non-covalent interactions as described herein, or by stabilization by one or more surfactants during formation of the matrix). Exemplary catalysts and catalyzed reactions are described herein.

Catalysts for Oxidation and Reduction

In some embodiments, the catalyst mediates oxidation or reduction of a substrate. For example, in some embodiments, the catalyst is a reactive oxygen species (ROS) generator, which catalyzes a chemical reaction to produce reactive oxygen species, i.e., chemically active molecules containing oxygen.

Exemplary catalysts for the oxidation or reduction of substrates can be ions or molecules, including, but not limited to, Fe(II), Fe(III), Ce(III), Ce(IV), Cu(I), Cu(II), Cr(III), Cr(VI), Co(II), Co(III), Ru(II), Ru(III), Ru(IV), Al(0), Al(III). These are well known to those skilled in the art and are described in Bokare and Choi, *J. Hazard. Mater.* 275 (2014) pp 121-135, which is fully incorporated by reference herein. The reaction mixture containing this type of catalyst may contain a suitable substrate, which can be converted to a product by the catalyst, leading to a signal change, e.g., fluorescence increase or decrease or absorbance increase or decrease. Additional components may be included in the reaction mixture to enhance the signal change, including, for example, redox-active fluorophore, redox-active absorber, or $H_2O_2$. The chemical reaction catalyzed by the catalyst can take place in a solution, which may be aqueous and may additionally contain organic solvents. The pH of the solution may be tuned for optimal detection. The reaction may use heat to increase the reaction rate (e.g., to a point that does not degrade $H_2O_2$) or light to increase the reaction rate.

Exemplary catalysts may also be a metal or metal oxide, which may be in nanoparticle form. In some embodiments, the catalyst can be iron oxide, cerium oxide, titanium dioxide, Pt, Pd, Al. Suitable substrates for this type of catalyst may include dihydrorhodamine 123, 10-acetyl-3,7-dihydroxyphenoxazine, 3,3',5,5'-tetramethylbenzidine, 2,2'-azino-bis(3-ethylbenzothiazoline-6-sulphonic acid), resazurin, coumarin-3-carboxylic acid, fluorescein and its lipophilic derivatives, methyl orange, terepthalic acid, 9-anthraldehyde, or nitrophenol. The chemical reaction catalyzed by the catalyst may take place in an aqueous solution containing possible organic cosolvents and the pH may be tuned for optimal detection. The reaction mixture may further comprise components such as redox-active fluorophore, redox-active absorber, and/or co-initiators (e.g., an energy-generating species, such as bis(2,4,5-trichloro-6-carbopentoxyphenyl) oxalate and bis(2,4,6-trichlorophenyl) oxlate; or an electron donor acceptor, such as glycerol and adenosine triphosphate; or a combination thereof). Co-initiators to be used in the present disclosure may include, but are not limited to, benzophenone, dissolved oxygen, or sodium borohydride. The reaction may use an energy source such as light or heat; for example, heat may be used to increase the reaction rate and light may be used for co-initiators. Alternatively or in addition, the reaction mixture may comprise an enhancer, which improves performance, e.g., signal development, detection, and/or longevity. Examples of suitable enhancers include, but are not limited to, imidazole, pyridine, sodium salicylate, sodium acetate, or a combination thereof. The chemical reaction would lead to a signal change, e.g., fluorescence increase or decrease or absorbance increase or decrease.

Still other exemplary ROS generators are nanoparticles, such as titanium dioxide, iron oxide, cerium oxide, indium oxide, indium tin oxide etc; nanoparticles may or may not contain dopants, such as W, In, Ag, Au, and Pt. Suitable substrates for such catalysts can be resazurin, coumarin-3-carboxylic acid, florescein, methyl orange, or terepthalic acid. The reaction may take place in an aqueous solution containing an organic solvent such as EtOH, IPA, DMF, and/or DMSO. Optionally, the reaction mixture may contain redox-active fluorophore, redox-active absorber; and/or electron acceptor to enhance signal detection. The reaction may take place under an energy source such as light or heat; for example, light may be used to enhance radical generation and/or heat may be used to increase the reaction rate.

Further, a catalyst may be a metalorganic complex, which is a complex comprising a metal (e.g., Fe, Mg, Cu, Mn, Pd, Pt, Ag, Ru, or Ce) and one or more organic ligands, e.g., porphyrin, substituted porphyrins, bipyridyls, bis-diimines, polydentates, ethanediamines, ethylenediamines, pentaaminecarbonates, tetraaminecarbonates, coumarins. Specific examples include, but are not limited to, iron porphyrins, hemin, ruthenium diimines, ruthenium bipyridyls, iridium-coumarin complexes, bis(1,2-ethanediamine)copper, nickel porphyrin, calcium ethylenediamine tetraacetate, and/or iron-tetraamidomacrocyclic ligand complexes. In some embodiments, the iron-tetraamidomacrocyclic ligand complexes is selected from those described in U.S. Pat. No. 6,100,394 (Fe-TAML complexes) and U.S. Pat. No. 8,754,206 (Fe-TAML-biuret complexes). For example, iron tetraamidomacrocyclic complexes include Fe(III)-TAML or derivatives thereof:

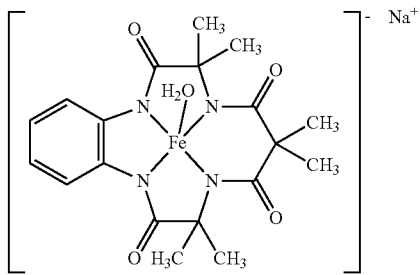

Exemplary substrates include those provided in Gomes et al., *J. Biochem. Biophys. Methods* 65, 45-80, 2005 (see, e.g., Table 1 on pages 48-49), or derivatives thereof. For example, in some embodiments, the substrate is selected from: hydroethidine (HE); 1,3-diphenylisobenzofuran (DPBF), 2-(2-pyridil)-benzothioazoline; 2,7-dichlorodihydrofluorescein (DCFH); 7-hydroxy-6-methoxy coumarin (scopoletin); 10-acetyl-3,7-dihydroxyphenoxazine (Amplex Red); 4-hydroxy-3-methoxy-phenylacetic acid (HVA or homovanillic acid); dihydrorhodamine 123 (DHR); 4-(9-anthroyloxy)-2,2,6,6,–tetramethylpiperidine-1-oxyl; 1,3-cyclohexanedione (CHD); sodium terephthalate; coumarin-3-carboxylic acid (3-CCA); N-succinimidyl ester of coumarin-3-carboxylic acid (SECCA); 2-[6-(4'-hydroxy)phenoxy-3H-xanthen-3-on-9-yl]benzoic acid (HPF); 2-[6-(4'-amino) phenoxy-3H-xanthen-3-on-9-yl]benzoic acid (APF); cis-parinaric acid (cis-PnA, (18:14):9,11,13,15-cis-trans-trans-cis-octadecaenoic acid); 4,4-difluoro-5-(4-phenyl-1,3-butadienyl)-4-bora-3a,4a-diaza-s-indacene-3-undecanoic acid ($C_{11}$-BODIPY); lipophilic fluorescein derivatives; dipyridamole; diphenyl-1-pyrenylphosphine (DPPP); 2,7-dichlorodihydrofluorescein acetate (DCFH-DA); beta-phycoerythrin; fluorescein; and 6-carboxyfluorescein, or a derivative thereof.

Still other exemplary substrates include, but are not limited to resazurin, coumarin-3-carboxylic acid, fluorescein, methyl orange, terepthalic acid, sodium terepthalate, 2-[6-(4'-hydroxy)phenoxy-3H-xanthen-3-on-9-yl]benzoic acid, 2-[6-(4'-amino)phenoxy-3H-xanthen-3-on-9-yl]benzoic acid, fluorescein, 2',7'-dichlorofluorescein, 2,7-dichlorodihydrofluorescein, hydroethidine, 1,3-diphenylisobenzofuran, 2-(2-pyridil)-benzothiazoline, 4-(9-anthroyloxy)-2,2,6,6-tetramethylpiperidine-1-oxyl, 1,3-cyclohexanedione, coumarin-3-carboxylic acid NHS ester, cis-parinaric acid, 4,4-difluoro-5-(4-phenyl-1,3-butadienyl)-4-bora-3a,4a-diaza-s-indacene-3-undecanoic acid), dipyridamole, diphenyl-1-pyrenylphosphine, 2,7-dichlorodihydrofluorescein diacetate, or TEMPO.

Singlet Oxygen Generators

In other examples, the catalyst is a singlet oxygen generator, which is a substance that produces singlet oxygen (dioxidene and dioxygen), an inorganic chemical in an excited state, via a chemical reaction. Examples include, but are not limited to, photosensitizers (see found at world wide web_3. nd.edu/~ndrlrcdc/Compilations/QY/QY1.HTM), phthalocyanines (metal-free or with any metal core), porphryins (metal-free or with any metal core), methylene blue, or rose Bengal.

Substrates for this type of catalysts include singlet oxygen-reactive fluorophores, absorbers, chemiluminophores, or photosensitizers. Examples are 9,10-dimethylanthracene, 1,3-diphenylisobenzofuran, 9-[2-(3-carboxy-9,10-dimethyl)anthryl]-6-hydroxy-3H-xanthen-3-one, or 9-[2-(3-carboxy-9,10-diphenyl)anthryl]-6-hydroxy-3H-xanthen-3-one. The reaction catalyzed by the catalyst may take place in a solution (e.g., an aqueous solution) which may contain an organic solvent such as EtOH, IPA, DMF, DMSO, or a combination thereof. In some instances, an organic solvent such as DMSO may be required. To enhance signal detection, the reaction mixture may further comprise dissolved oxygen (or an oxygen source), singlet oxygen-reactive fluorescent or absorbent species, and/or an organic solvent such as DMSO. An energy source such as light or heat may be used for the reaction, for example, light-induced singlet oxygen generation.

Cycloaddition Reactions and Pi-Allyl Reactions

In yet other examples, the catalyst is or is an ion of, e.g., Cu, Pd, or Pt, which may release precursors that yields a fluorescent molecule by catalytic Tsuji-Trost or Claisen "pi-allyl" reaction. These are well-known to those skilled in the art and are described in Chan, Dodani, and Chang, *Nature Chem.* 4 (2012) pp 973-984, which are incorporated by reference herein. The reaction may take place in an aqueous solution, which may further comprise substances such as dye precursor and/or reducing agent or nucleophile to enhance signal detection. Suitable substrates for this type of catalysts may be allylated or propargylated fluorescein derivatives.

Cu(I) or Cu(II) ions can be used to catalyze a Huisgen cycloaddition "click" reaction, which is well known in the art. See, e.g., Kolb et al., (2003). "The growing impact of click chemistry on drug discovery" 8 (24). pp. 1128-1137. Suitable substrates for a click reaction include, but are not limited to, 3-azido coumarin derivatives, 4-azido or 4-alkynyl-1,8-napthalimide, corresponding azide or alkyne partner, and all other compounds disclosed in "Fluorogenic click reaction" by Wang et al. The reaction may take place in a solution (solvent or a mixture of solvent and solute(s)), which may be aqueous-based. The solution may contain an organic solvent, such as DMF and/or DMSO. It may also include substances such as azide, alkyne, and/or Cu reducer to enhance reaction or signal detection. Heat or electromagnetic energy may be used as an energy source for the reaction.

Fluorescence-Modulating Reactions

In some embodiments, the transition-metal catalyst (e.g., a transition-metal catalyst that comprises Pd(II) or Pd(0) or ligands such as monodentate phosphine ligands, bidentate phosphine ligands, monodentate Schiff base ligands, bidentate Schiff base ligands, tridentate Schiff base ligands, macrocyclic ligands, pentamethylcyclopentadiene, monodentate arsine, or N-heterocyclic carbene ligands) induces fluorescence by mediating a bond cleavage reaction of the fluorescence quenching functional group in the substrate compound.

Exemplary substrates are described in Chan, Dodani, and Chang, *Nature Chem.* 4 (2012) pp 973-984; Prusty and Herrmann, *J. Am. Chem. Soc.* 132 (2010) pp 12197-12199; and Prusty et al, *Angew. Chem. Int. Ed.* 124 (2012) pp 12064-12068, which are incorporated by reference herein. These include halogenated chemiluminophore precursors (e.g., a halogenated boron dipyrromethane (BODIPY) compound, where cleavage of the halogen group enhances fluorescence).

Molecular Intercalator

In some embodiments, the signaling agent described herein may be a compound, which can form a complex with a binding partner, wherein the complex is capable of releasing a detectable signal.

For example, such a compound can be a molecular intercalator, which refers to a compound that can insert between the planar bases of a nucleic acid or similar layered structure. Examples include, but are not limited to, Ethidium bromide, POPO-3 iodide, SYBR Gold, SYBR Green I, SYBR Green II, TO-PRO-1 iodide, TO-PRO-3 iodide, TOTO-1 iodide, TOTO-3 iodide, YO-PRO-1 iodide, YOYO-1 iodide, Quant-iT PicoGreen, Quant-iT OliGreen, Quant-iT RiboGreen, SYTOX Blue, SYTOX Green, SYTOX Orange, SYTOX Red, POPO-1, BOBO-1, YOYO-1, TOTO-1, JOJO-1, POPO-3, LOLO-1, BOBO-3, YOYO-3, TOTO-3, PO-PRO-1, YO-PRO-1, JO-PRO-1, PO-PRO-1, YO-PRO-3, TO-PRO-3, TO-PRO-S. The binding partner can be a nucleic acid, such as a single-chain DNA or RNA. The binding reaction can occur in a solution (e.g., an aqueous solution) which may comprise suitable organic solvent and/or a pH tuned for optimal detection. Energy sources such as heat, electromagnetic radiation, and/or mechanical vibration (e.g. sound) may be used to enhance complex formation.

Alternatively, the compound may be an ion for chelation with fluorescent or absorbent precursors. Such ions include, but are not limited to, H, Li, Na, K, F, Rb, Cs, Cu, Ag, Au, Be, Mg, Ca, Sr, BA, Zn, Cd, Hg, Al, P, Ga In, Tl, Sc, Y, La, Ce, Pr, Nd, Sm, Eu, Gd, Tb, Dy, Ho, Er, Tm, Yb, Lu, Th, U, Sn, Pb, Ti, Zr, Hf, As, Sb, Bi, V, Nb, Ta, Cr, Mo, W, Mn, Re, Fe, Co, Ni, Ru, Rh, Pd, Os, Ir, or Pt. When in contact with a chemiluminescent precursor or absorbent precursor, the ion may form a complex with the precursor and the complex may release a fluorescent, absorbent, or chemiluminescent signal. Exemplary fluorescent precursors and absorbent precursors include, but are not limited to, 8-hydroxyquinoline, 8-hydroxyquinoline-5-sulfonic acid, 2-(((pyridin-2-ylmethyl)imino)methyl)phenol, 9-Acridone-4-carboxylic acid, or L-lysine. Formation of the complex may take place in a solution such as an aqueous solution, which may comprise organic solvents (e.g., DMSO or DMF) and a pH tuned for optimal detection. Energy sources such as heat, electromagnetic radiation, and/or mechanical vibrations, may be used to increase the rate of mixing.

Chemiluminophores, Absorbers, and Precursors Thereof

Another example of the signaling agent described herein can be a chemiluminophore or an absorber, or a precursor thereof. Exemplary chemiluminophores, absorbers, or precursors thereof include: Oregon green, eosin, Texas red, BODIPY, AlexaFluor, Atto, cyanine, indocarbocyanine, oxacarbocyanine, thiacarbocyanine, merocyanine, dansyl, prodan, coumarin, pyridyloxazole, nitrobenzoxadiazole, benzoxadiazole, anthraquinone, cascade blue, Nile red, Nile blue, cresyl violet, proflavin, acridine orange, acridine yellow, auramine, crystal violet, malachite green, porphin, phthalocyanine, bilirubin, 9,10-diphenylanthracene, 1-chloro-9,10-diphenylanthracene, 9,10-bis(phenylethynyl)anthracene, 1-chloro-9,10-bis(phenylethynyl)anthracene, 2-chloro-9,10-bis(phenylethynyl)anthracene, 1,8-dichloro-9,10-bis(phenylethynyl)anthracene, rubrene, 2,4-di-tert-butylphenyl-1,4,5,8-tetracarboxynaphthalene diamie, 5,12-bis(phenylethynyl)naphthacene, violanthrone, 16,16-(1,2-ethylenedioxy)violanthrone, 16,17-dihexyloxyviolanthrone, 16,17-butyloxyviolanthrone, N,N'-bis(2,5-di-tert-butylphenyl)-3,4,9,10-perylenedicarboximide, 1-N,N'-dibutylaminoanthracene, 6-methylacridinium iodide, and luminol, or a derivative thereof (e.g., an acylated, alkylated, alkoxylated, and/or halogenated derivative of the compounds described herein).

A chemiluminophore is an atom, a molecule, a compound, or functional group in a chemical compound that is responsible for its luminescent properties upon electromagnetic excitation (e.g., light, radiative, or non-radiative intersystem energy transfer such as Forster resonance energy transfer, or thermal excitation), the luminophore (e.g., a dye or a fluorophore) releases a detectable signal.

An exemplary chemiluminophore is a fluorophore, which is a fluorescent chemical compound that can emit light upon excitation. Excitation may be optical or chemical in nature. Examples of the chemiluminophores include fluorescein, rhodamine, resorufin, AlexaFluor, BODIPY, Cy, Dansyl, SYTO, chloro-9,10-diphenylanthracene, chloro-9,10-bis(phenylethynyl)anthracene, dichloro-9,10-bis(phenylethynyl)anthracene, rubrene, 5,12-bis(phenylethynyl)naphthacene. Additional examples are provided in Tables 1A and 1B and those disclosed in US20100171043, which is incorporated by reference herein.

TABLE 1A

| Fluorophore | Absorption | Emission | Other info |
| --- | --- | --- | --- |
| 1,5 IAEDANS | 336 | 490 | r |
| 1,8-ANS | 372 | 480 | r |
| 4-Methylumbelliferone | 385 | 502 | r |
| 5-carboxy-2,7-dichlorofluorescein | 504 | 529 | r |
| 5-Carboxyfluorescein (5-FAM) | 492 | 518 | r |

TABLE 1A-continued

| Fluorophore | Absorption | Emission | Other info |
|---|---|---|---|
| 5-Carboxynapthofluorescein (pH 10) | 512/598 | 563/668 | Ratio Dye, pH |
| 5-Carboxytetramethylrhodamine (5-TAMRA) | 542 | 568 | r |
| 5-FAM (5-Carboxyfluorescein) | 492 | 518 | r |
| 5-HAT (Hydroxy Tryptamine) | 370-415 | 520-540 | r |
| 5-Hydroxy Tryptamine (HAT) | 370-415 | 520-540 | r |
| 5-ROX (carboxy-X-rhodamine) | 578 | 604 | r |
| | 567 | 591 | |
| 5-TAMRA (5-Carboxytetramethylrhodamine) | 548 | 552 | r |
| | 542 | 568 | |
| 6-Carboxyrhodamine 6G | 518 | 543 | r |
| 6-CR 6G | 518 | 543 | r |
| 6-JOE | 520 | 548 | r |
| 7-Amino-4-methylcoumarin | 351 | 430 | r |
| 7-Aminoactinomycin D (7-AAD) | 546 | 647 | r |
| 7-Hydroxy-4-methylcoumarin | 360 | 449, 455 | r |
| 9-Amino-6-chloro-2-methoxyacridine | 412, 430 | 471, 474 | r |
| ABQ | 344 | 445 | r |
| Acid Fuchsin | 540 | 630 | r |
| ACMA (9-Amino-6-chloro-2-methoxyacridine) | 412, 430 | 471, 474 | r |
| Acridine Orange + DNA | 502 | 526 | r |
| Acridine Orange + RNA | 460 | 650 | r |
| Acridine Orange, both DNA & RNA | 440-480 | 520-650 | r |
| Acridine Red | 455-600 | 560-680 | r |
| Acridine Yellow | 470 | 550 | r |
| Acriflavin | 436 | 520 | r |
| Acriflavin Feulgen SITSA | 355-425 | 460 | r |
| Aequorin (Photoprotein) | r | 466 | Photoprotein |
| AFPs - AutoFluorescent Protein - (Quantum Biotechnologies) see sgGFP, sgBFP | r | | |
| Alexa Fluor 350 ™ | 346 | 442 | r |
| | 342 | 441 | |
| Alexa Fluor 430 ™ | 431 | 540 | r |
| Alexa Fluor 488 ™ | 495, 492 | 519, 520 | r |
| Alexa Fluor 532 ™ | 531, 532 | 553, 554 | r |
| Alexa Fluor 546 ™ | 556, 557 | 572, 573 | r |
| Alexa Fluor 568 ™ | 577, 578 | 603 | r |
| Alexa Fluor 594 ™ | 590, 594 | 617, 618 | r |
| Alexa Fluor 633 ™ | 632 | 650 | r |
| Alexa Fluor 647 ™ | 647 | 666 | r |
| Alexa Fluor 660 ™ | 668 | 698 | r |
| Alexa Fluor 680 ™ | 679 | 702 | r |
| Alizarin Complexon | 530-560, 580 | 580, 624-645 | r |
| Alizarin Red | 530-560 | 580 | r |
| Allophycocyanin (APC) | 630, 645 | 655, 660 | r |
| AMC, AMCA-S | 345 | 445 | r |
| AMCA (Aminomethylcoumarin) | 345 | 425 | r |
| | 347 | 444 | |
| AMCA-X | 353 | 442 | r |
| Aminoactinomycin D | 555 | 655 | r |
| Aminocoumarin | 346 | 442 | r |
| | 350 | 445 | |
| Aminomethylcoumarin (AMCA) | 345 | 425 | r |
| | 347 | 444 | |
| Anilin Blue | | 600 | r |
| Anthrocyl stearate | 360-381 | 446 | r |
| APC (Allophycocyanin) | 630, 645 | 655, 660 | r |
| APC-Cy7 | 625-650 | 755 | r |
| APTRA-BTC = Ratio Dye, Zn2+ | 466/380 | 520/530 | Ratio Dye, Zn2+ |
| APTS | 424 | 505 | r |
| Astrazon Brilliant Red 4G | 500 | 585 | r |
| Astrazon Orange R | 470 | 540 | r |
| Astrazon Red 6B | 520 | 595 | r |
| Astrazon Yellow 7 GLL | 450 | 480 | r |
| Atabrine | 436 | 490 | r |
| ATTO-TAGT ™ CBQCA | 465 | 560 | r |
| ATTO-TAG ™ FQ | 486 | 591 | r |
| Auramine | 460 | 550 | r |
| Aurophosphine G | 450 | 580 | r |
| Aurophosphine | 450-490 | 515 | r |
| BAO 9 (Bisaminophenyloxadiazole) | 365 | 395 | r |
| BCECF (high pH) | 492, 503 | 520, 528 | r |
| BCECF (low pH) | 482 | 520 | r |
| Berberine Sulphate | 430 | 550 | r |
| Beta Lactamase | 409 | 447, 520 | r |

TABLE 1A-continued

| Fluorophore | Absorption | Emission | Other info |
|---|---|---|---|
| BFP blue shifted GFP (Y66H) Blue Fluorescent Protein | 381, 382, 383 | 445, 447, 448 | blue shifted GFP (Y66H) Blue Fluorescent Protein |
| BFP/GFP FRET | r | r | r |
| Bimane | 398 | 490 | r |
| Bisbenzamide | 360 | 461 | r |
| Bisbenzimide (Hoechst) | 360 | 461 | r |
| bis-BTC = Ratio Dye, Zn2+ | 455/405 | 529/505 | Ratio Dye, Zn2+ |
| Blancophor FFG | 390 | 470 | r |
| Blancophor SV | 370 | 435 | r |
| BOBO ™-1 | 462 | 481 | r |
| BOBO ™-3 | 570 | 602 | r |
| Bodipy 492/515 | 490 | 515 | r |
| Bodipy 493/503 | 533 | 549 | r |
| Bodipy 500/510 | 509 | 515 | r |
| Bodipy 505/515 | 502 | 510 | r |
| Bodipy 530/550 | 528 | 547 | r |
| Bodipy 542/563 | 543 | 563 | r |
| Bodipy 558/568 | 558 | 569 | r |
| Bodipy 564/570 | 564 | 570 | r |
| Bodipy 576/589 | 579 | 590 | r |
| Bodipy 581/591 | 584 | 592 | r |
| Bodipy 630/650-X | 625 | 642 | r |
| Bodipy 650/665-X | 647 | 665 | r |
| Bodipy 665/676 | 605 | 676 | r |
| Bodipy Fl | 504, 505 | 511, 513 | r |
| Bodipy FL ATP | 505 | 514 | r |
| Bodipy Fl-Ceramide | 505 | 511 | r |
| Bodipy R6G SE | 528 | 547 | r |
| Bodipy TMR | 542 | 574 | r |
| Bodipy TMR-X conjugate | 544 | 573 | r |
| Bodipy TMR-X, SE | 544 | 570 | r |
| Bodipy TR | 589 | 617 | r |
| Bodipy TR ATP | 591 | 620 | r |
| Bodipy TR-X SE | 588 | 616 | r |
| BO-PRO ™-1 | 462 | 481 | r |
| BO-PRO ™-3 | 544 | 570 | r |
| Brilliant Sulphoflavin FF | 430 | 520 | r |
| BTC - Ratio Dye Ca2+ | 464/401 | 533/529 | Ratio Dye Ca2+ |
| BTC-5N - atio Dye, Zn2+ | 459/417 | 517/532 | Ratio Dye, Zn2+ |
| Calcein | 494 | 517 | r |
| Calcein Blue | 373 | 440 | r |
| Calcium Crimson ™ | 588, 589 | 611, 615 | r |
| Calcium Green | 501, 506 | 531 | r |
| Calcium Green-1 Ca2+ Dye | 506 | 531 | Ca2+ Dye |
| Calcium Green-2 Ca2+ | 506/503 | 536 | Ca2+ |
| Calcium Green-5N Ca2+ | 506 | 532 | Ca2+ |
| Calcium Green-C18 Ca2+ | 509 | 530 | Ca2+ |
| Calcium Orange | 549 | 575, 576 | r |
| Calcofluor White | 385, 395, 405 | 437, 440, 445 | r |
| Carboxy-X-rhodamine (5-ROX) | 576 | 601 | r |
| Cascade Blue ™ | 377, 398, 399 | 420, 423 | r |
| Cascade Yellow | 399, 400 | 550, 552 | r |
| Catecholamine | 410 | 470 | r |
| CCF2 (GeneBlazer) | r | r | r |
| CFDA | 494 | 520 | r |
| CFP - Cyan Fluorescent Protein | 430, 433, 436, (453) | 474, 475, 476, (501) | Cyan Fluorescent Protein |
| CFP/YFP FRET | r | r | r |
| Chlorophyll | 480 | 650 | r |
| Chromomycin A | 436-460 | 470 | r |
| Chromomycin A | 445 | 575 | r |
| CL-NERF (Ratio Dye, pH) | 504/514 | 540 | Ratio Dye, pH |
| CMFDA | 494 | 520 | r |
| Coelenterazine Ca2+ Dye, bioluminescence | (429) | 465 | Ca2+ Dye, bioluminescence, native molecule |
| Coelenterazine cp (Ca2+ Dye,) | (430) | 442 | Ca2+ Dye, bioluminescence |
| Coelenterazine f | (437) | 473 | Ca2+ Dye, bioluminescence |

TABLE 1A-continued

| Fluorophore | Absorption | Emission | Other info |
|---|---|---|---|
| Coelenterazine fcp | r | 452 | Ca2+ Dye, bioluminescence |
| Coelenterazine h | (437) | 464 | Ca2+ Dye, bioluminescence |
| Coelenterazine hcp | (433) | 444 | Ca2+ Dye, bioluminescence |
| Coelenterazine ip | r | 441 | Ca2+ Dye, bioluminescence |
| Coelenterazine n | (431) | 467 | Ca2+ Dye, bioluminescence |
| Coelenterazine O | 460 | 575 | r |
| Coumarin Phalloidin | 387 | 470 | r |
| C-phycocyanine | r | r | r |
| CPM Methylcoumarin | 384 | 469 | Methylcoumarin |
| CTC | 400-450 | 602 | |
| CTC Formazan | r | r | r |
| Cy2 ™ | 489 | 506 | r |
| Cy3.18 | 554 | 568 | r |
| Cy3.5 ™ | 581 | 598 | r |
| Cy3 ™ | 514 | 566 | r |
| | 552 | 570 | |
| | 554 | | |
| Cy5.18 | 649 | 666 | r |
| Cy5.5 ™ | 675 | 695 | r |
| Cy5 ™ | 649 | 666 | r |
| | r | 670 | |
| Cy7 ™ | 710, 743 | 767, 805 | r |
| Cyan GFP | 433 (453) | 475 (501) | r |
| cyclic AMP Fluorosensor (FiCRhR) | 500 | 517 | r |
| CyQuant Cell Proliferation Assay | 480 | 520 | Cell Proliferation Assay |
| Dabcyl | 453 | r | r |
| Dansyl | 340 | 578 | r |
| Dansyl Amine | 337 | 517 | r |
| Dansyl Cadaverine | 335 | 518 | r |
| Dansyl Chloride | 372 | 518 | r |
| Dansyl DHPE | 336 | 517 | r |
| Dansyl fluoride | 356 | none | r |
| DAPI | 359 | 461 | r |
| Dapoxyl | 403 | 580 | r |
| Dapoxyl 2 | 374 | 574 | r |
| Dapoxyl 3 | 373 | 574 | r |
| DCFDA | 504 | 529 | r |
| DCFH (Dichlorodihydrofluorescein Diacetate) | 505 | 535 | r |
| DDAO | 463 | 607 | r |
| DHR (Dihydorhodamine 123) | 505 | 534 | r |
| Di-4-ANEPPS | 496 | 705 | r |
| Di-8-ANEPPS (non-ratio) | 488 | 605 | r |
| | 498 | 713 | r |
| DiA (4-Di-16-ASP) | 456 | 591 | r |
| Dichlorodihydrofluorescein Diacetate (DCFH) | 505 | 535 | r |
| DiD - Lipophilic Tracer | 644 | 665 | Lipophilic Tracer |
| DiD (DiIC18(5)) | 644 | 665 | r |
| DIDS | 341 | 415 | r |
| Dihydorhodamine 123 (DHR) | 505 | 535 | r |
| DiI (DiIC18(3)) | 549, 551 | 565 | r |
| Dinitrophenol | 349 | | r |
| DiO (DiOC18(3)) | 484, 487 | 501, 502 | r |
| DiR | 748 | 780 | Lipophilic Tracer |
| DiR (DiIC18(7)) | 750 | 779 | r |
| DM-NERF (high pH) | 497/510 | 540 | Ratio Dye, pH |
| DNP | 349 | r | r |
| Dopamine | 340 | 490-520 | r |
| DsRed | 558 | 583 | Red fluorescent protein |
| DTAF | 494 | 520 | r |
| DY-630-NHS | 621 | 660 | Hemicyane label for proteins and DNA |
| DY-635-NHS | 634 | 664 | Hemicyane label for proteins and DNA |

TABLE 1A-continued

| Fluorophore | Absorption | Emission | Other info |
|---|---|---|---|
| EBFP | 383 | 447 | Enhanced Blue Fluorescent Protein |
| ECFP | 436 | 474 | Enhanced Cyan Fluorescent Protein |
| EGFP | 488, 498 | 507, 516 | Enhanced Green Fluorescent Protein |
| ELF 97 | 345 | 530 | ″ |
| Eosin | 524 | 545 | ″ |
| Erythrosin | 529, 532 | 554, 555 | ″ |
| Erythrosin ITC | 529 | 555 | ″ |
| Ethidium Bromide | 510, 523 | 595, 605 | ″ |
| Ethidium homodimer-1 (EthD-1) | 528 | 617 | ″ |
| Euchrysin | 430 | 540 | ″ |
| EukoLight | ″ | ″ | ″ |
| Europium (III) chloride | ″ | ″ | ″ |
| EYFP | 513, 520 | 527, 532 | Enhanced Yellow Fluorescent Protein |
| Fast Blue | 360 | 440 | ″ |
| FDA | 494 | 520 | ″ |
| Feulgen (Pararosaniline) | 570 | 625 | ″ |
| FIF (Formaldehyd Induced Fluorescence) | 405 | 433 | ″ |
| FITC | 490, 494 | 520, 525 | ″ |
| FITC Antibody | 493 | 517 | ″ |
| Flazo Orange | 375-530 | 612 | ″ |
| Fluo-3 | 480-506, 506 | 520, 527 | ″ |
| Fluo-4 | 494 | 516 | ″ |
| Fluorescein (FITC) | 490, 494 | 520, 525 | ″ |
| Fluorescein Diacetate | 494 | 520 | ″ |
| Fluoro-Emerald | 495 | 524 | ″ |
| Fluoro-Gold (Hydroxystilbamidine) | 361 | 536 | ″ |
| Fluor-Ruby | 555 | 582 | ″ |
| FluorX | 494 | 520 | ″ |
| FM 1-43 ™ | 479 | 598 | ″ |
| FM 4-46 | 515 | 640 | ″ |
| Fura Red ™ (high pH) | 572 | 657 | ″ |
| Fura Red ™/Fluo-3 | ″ | ″ | ″ |
| Fura-2, high calcium | 335 | 505 | Excitation ratio dye |
| Fura-2, low calcium | 363 | 512 | Excitation ratio dye |
| Fura-2/BCECF | ″ | ″ | ″ |
| Genacryl Brilliant Red B | 520 | 590 | ″ |
| Genacryl Brilliant Yellow 10GF | 430 | 485 | ″ |
| Genacryl Pink 3G | 470 | 583 | ″ |
| Genacryl Yellow 5GF | 430 | 475 | ″ |
| GeneBlazer (CCF2) | ″ | ″ | ″ |
| GFP (S65T) | 498 | 516 | ″ |
| GFP red shifted (rsGFP) | 498 | 516 | ″ |
| GFP wild type, non-UV excitation (wtGFP) | 475 | 509 | ″ |
| GFP wild type, UV excitation (wtGFP) | 395 | 509 | ″ |
| GFPuv | 385 | 508 | ″ |
| Gloxalic Acid | 405 | 460 | ″ |
| Granular Blue | 355 | 425 | ″ |
| Haematoporphyrin | 530-560 | 580 | ″ |
| Hoechst 33258 | 345 | 487 | ″ |
| Hoechst 33342 | 347 | 483 | ″ |
| Hoechst 34580 | 392 | 440 | ″ |
| HPTS | 355 | 465 | ″ |
| Hydroxycoumarin | 325-360 | 386-455 | ″ |
| Hydroxystilbamidine (FluoroGold) | 361 | 536 | ″ |
| Hydroxytryptamine | 400 | 530 | ″ |
| Indo-1, high calcium | 330 | 401 | Emission ratio dye |
| Indo-1, low calcium | 346 | 475 | Emission ratio dye |
| Indodicarbocyanine (DiD) | 644 | 665 | ″ |
| Indotricarbocyanine (DiR) | 748 | 780 | ″ |
| Intrawhite Cf | 360 | 430 | ″ |
| JC-1 | 514 | 529 | ″ |
| JO-JO-1 | 530 | 545 | ″ |
| JO-PRO-1 | 532 | 544 | ″ |
| LaserPro | 795 | 812 | ″ |
| Laurodan | 355 | 460 | ″ |
| LDS 751 (DNA) | 543 | 712 | ″ |
| LDS 751 (RNA) | 590 | 607 | ″ |

TABLE 1A-continued

| Fluorophore | Absorption | Emission | Other info |
|---|---|---|---|
| Leucophor PAF | 370 | 430 | " |
| Leucophor SF | 380 | 465 | " |
| Leucophor WS | 395 | 465 | " |
| Lissamine Rhodamine | 572, 577 | 591, 592 | " |
| Lissamine Rhodamine B | 577 | 592 | " |
| LIVE/DEAD Kit Animal Cells | 494 | 517 | for more details refer to the world wide web at probes.com |
| Calcein/Ethidium homodimer | 528 | 617 | " |
| LOLO-1 | 566 | 580 | " |
| LO-PRO-1 | 568 | 581 | " |
| Lucifer Yellow | 425, 428 | 528, 536, 540 | " |
| Lyso Tracker Blue | 373 | 422 | " |
| Lyso Tracker Blue-White | 466 | 536 | " |
| Lyso Tracker Green | 504, 534 | 511, 551 | " |
| Lyso Tracker Red | 490 | 516 | " |
| Lyso Tracker Yellow | 551 | 576 | " |
| LysoSensor Blue | 374 | 424 | " |
| LysoSensor Green | 442 | 505 | " |
| LysoSensor Yellow/Blue | 384 | 540 | " |
| Mag Green | 507 | 531 | " |
| Magdala Red (Phloxin B) | 524 | 600 | " |
| Mag-Fura Red | 483/427 | 659/631 | Ratio Dye, Mg2+ |
| Mag-Fura-2 | 369/329 | 508 | Ratio Dye Ca2+ |
|  | 369/330 | 511/491 | Ratio Dye Mg2+ |
| Mag-Fura-5 | 369/330 | 505/500 | Ratio Dye, Ca2+ |
|  | 369/332 | 505/482 | Ratio Dye, Mg2+ |
| Mag-Indo-1 | 349/328 | 480/390 | Ratio Dye, Ca2+ |
|  | 349/330 | 480/417 | Ratio Dye, Mg2+ |
| Magnesium Green | 506, 507 | 531 | " |
| Magnesium Orange | 550 | 575 | " |
| Malachite Green | 628 |  | " |
| Marina Blue | 362 | 459 | " |
| Maxilon Brilliant Flavin 10 GFF | 450 | 495 | " |
| Maxilon Brilliant Flavin 8 GFF | 460 | 495 | " |
| Merocyanin | 555 | 578 | " |
| Methoxycoumarin | 360 | 410 | " |
| Mitotracker Green FM | 490 | 516 | " |
| Mitotracker Orange | 551 | 576 | " |
| Mitotracker Red | 578 | 599 | " |
| Mitramycin | 450 | 470 | " |
| Monobromobimane | 398 | 490 | " |
| Monobromobimane (mBBr-GSH) | 398 | 500 | " |
| Monochlorobimane | 380 | 461 | " |
| MPS (Methyl Green Pyronine Stilbene) | 364 | 395 | " |
| NBD | 466 | 539 | " |
| NBD Amine | 450 | 530 | " |
| Nile Red | 515-555, 559 | 590, 640 | " |
| Nitrobenzoxadidole | 465 | 510-650 | " |
| Noradrenaline | 340 | 490-520 | " |
| Nuclear Fast Red | 289-530 | 580 | " |
| Nuclear Yellow | 365 | 495 | " |
| Nylosan Brilliant lavin E8G | 460 | 510 | " |
| Oregon Green | 503 | 522 | " |
| Oregon Green 488-X | 494 | 517 | " |
| Oregon Green ™ | 503 | 522 | " |
| Oregon Green ™ 488 | 490, 493 | 514, 520 | " |
| Oregon Green ™ 500 | 497 | 517 | " |
| Oregon Green ™ 514 | 506 | 526 | " |
| Pacific Blue | 405 | 455 | " |
| Pararosaniline (Feulgen) | 570 | 625 | " |
| PBFI | 340/380 | 420 | Excitation ratio dye |
| PE-Cy5 | 488 | 670 | " |
| PE-Cy7 | 488 | 755, 767 | " |
| PerCP | 488 | 675 | " |
| PerCP-Cy5.5 | 488 | 710 | " |
| PE-TexasRed [Red 613] | 488 | 613 | " |
| Phloxin B (Magdala Red) | 524 | 600 | " |
| Phorwite AR | 360 | 430 | " |
| Phorwite BKL | 370 | 430 | " |
| Phorwite Rev | 380 | 430 | " |
| Phorwite RPA | 375 | 430 | " |
| Phosphine 3R | 465 | 565 | " |
| PhotoResist | 365 | 610 | " |

TABLE 1A-continued

| Fluorophore | Absorption | Emission | Other info |
|---|---|---|---|
| Phycoerythrin B [PE] | 546-565 | 575 | r |
| Phycoerythrin R [PE] | 565 | 578 | r |
| PKH26 (Sigma) | 551 | 567 | r |
| PKH67 | 496 | 520 | Chroma |
| PMIA | 341 | 376 | r |
| Pontochrome Blue Black | 535-553 | 605 | r |
| POPO-1 | 433 | 457 | r |
| POPO-3 | 533 | 574 | r |
| PO-PRO-1 | 435 | 455 | r |
| PO-PRO-3 | 539 | 567 | r |
| Primuline | 410 | 550 | r |
| Procion Yellow | 470 | 600 | r |
| Propidium Iodid (PI) | (305), 536, 538 | 617 | r |
| PyMPO | 412, 415 | 561, 564, 570 | r |
| Pyrene | 360 | 387 | r |
| Pyronine | 410 | 540 | r |
| Pyronine B | 540-590 | 560-650 | r |
| Pyrozal Brilliant Flavin 7GF | 365 | 495 | r |
| QSY 7 | 560 | | r |
| Quinacrine Mustard | 440 | 510 | r |
| Red 613 [PE-TexasRed] | 488 | 613 | r |
| Resorufin | 571 | 584, 585 | r |
| RH 414 | 532 | 716 | r |
| Rhod-2 | 552 | 576 | r |
| Rhodamine | 550 | 573 | r |
| Rhodamine 110 | 496, 497 | 520 | r |
| Rhodamine 123 | 507 | 529 | r |
| Rhodamine 5 GLD | 470 | 565 | r |
| Rhodamine 6G | 525 | 555 | r |
| Rhodamine B | 540 | 625 | r |
| Rhodamine B 200 | 523-557 | 595 | r |
| Rhodamine B extra | 550 | 605 | r |
| Rhodamine BB | 540 | 580 | r |
| Rhodamine BG | 540 | 572 | r |
| Rhodamine Green | 502 | 527 | r |
| Rhodamine Phallicidine | 558, 542 | 575, 565 | r |
| Rhodamine Phalloidine | 542 | 565 | r |
| Rhodamine Red | 570 | 590 | r |
| Rhodamine WT | 530 | 555 | r |
| Rose Bengal | 525, 540 | 550-600 | r |
| R-phycocyanine | r | r | r |
| R-phycoerythrin (PE) | 565 | 578 | r |
| rsGFP | 473 | 509 | red shifted GFP (S65T) |
| S65A | 471 | 504 | r |
| S65C | 479 | 507 | r |
| S65L | 484 | 510 | r |
| S65T | 488 | 511 | r |
| Sapphire GFP | 395 | 511 | r |
| SBFI | 340/380 | 420 | Excitation ratio dye |
| Serotonin | 365 | 520-540 | r |
| Sevron Brilliant Red 2B | 520 | 595 | r |
| Sevron Brilliant Red 4G | 500 | 583 | r |
| Sevron Brilliant Red B | 530 | 590 | r |
| Sevron Orange | 440 | 530 | r |
| Sevron Yellow L | 430 | 490 | r |
| sgBFP ™ | 387 | 450 | r |
| sgBFP ™ (super glow BFP) | 387 | 450 | Quantum's SuperGlo ™GFP AFPs |
| sgGFP ™ | 474 | 488 | |
| sgGFP ™ (super glow GFP) | 474 | 509 | Quantum's SuperGlo ™GFP AFPs |
| SITS | 336 | 436 | Ion Channels |
| SITS (Primuline) | 395-425 | 450 | r |
| SITS (Stilbene Isothiosulphonic Acid) | 365 | 460 | r |
| SNAFL calcein | 506/535 | 535/620 | Ratio Dye, pH |
| SNAFL-1 | 508/540 | 543/623 | Ratio Dye, pH |
| SNAFL-2 | 514/543 | 546/630 | Ratio Dye, pH |
| SNARF calcein | 552/574 | 590/629 | Ratio Dye, pH |
| SNARF1 | 576/548 | 635/587 | Excitation and emission ratio dye |
| Sodium Green | 506, 507 | 532 | Na+, K+ |
| SpectrumAqua | 433,/53 | 480/55 | Vysis |

TABLE 1A-continued

| Fluorophore | Absorption | Emission | Other info |
|---|---|---|---|
| SpectrumGreen | 497/30, 509/31 | 538/44, 524/56 Vysis | r |
| SpectrumOrange | 559/38, 560 | 588/48 | Vysis |
| Spectrum Red | 587, 587/35 | 612, 612/51 | r |
| SPQ (6-methoxy-N-(3-sulfopropyl) quinolinium) | 344 | 443 | r |
| Stilbene | 335 | 440 | r |
| Sulphorhodamine B can C | 520 | 595 | r |
| Sulphorhodamine G Extra | 470 | 570 | r |
| SYTO 11 | 508, 510 | 527, 530 | Dye for DNA, RNA |
| SYTO 12 | 499, 500 | 522, 519 | Dye for DNA, RNA |
| SYTO 13 | 488, 491 | 509, 514 | Dye for DNA, RNA |
| SYTO 14 | 517, 521 | 549, 547 | Dye for DNA, RNA |
| SYTO 15 | 516, 518 | 546, 555 | Dye for DNA, RNA |
| SYTO 16 | 488, 494 | 518, 525 | Dye for DNA, RNA |
| SYTO 17 | 621 | 634 | Dye for DNA |
| SYTO 18 | 490, 493 | 507, 527 | Dye for DNA, RNA |
| SYTO 20 | 512 | 530 | Dye for DNA |
| SYTO 21 | 494 | 517 | Dye for DNA |
| SYTO 22 | 515 | 535 | Dye for DNA |
| SYTO 23 | 499 | 520 | Dye for DNA |
| SYTO 24 | 490 | 515 | Dye for DNA |
| SYTO 25 | 521 | 556 | Dye for DNA |
| SYTO 40 | 420 | 441 | Dye for DNA |
| SYTO 41 | 430 | 454 | Dye for DNA |
| SYTO 42 | 433 | 460 | Dye for DNA |
| SYTO 43 | 436 | 467 | Dye for DNA |
| SYTO 44 | 446 | 471 | Dye for DNA |
| SYTO 45 | 452 | 484 | Dye for DNA |
| SYTO 59 | 622 | 645 | Dye for DNA |
| SYTO 60 | 652 | 678 | Dye for DNA |
| SYTO 61 | 628 | 645 | Dye for DNA |
| SYTO 62 | 652 | 676 | Dye for DNA |
| SYTO 63 | 657 | 673 | Dye for DNA |
| SYTO 64 | 599 | 619 | Dye for DNA |
| SYTO 80 | 531 | 545 | Nucleic Acid Stain |
| SYTO 81 | 530 | 544 | Nucleic Acid Stain |
| SYTO 82 | 541 | 560 | Nucleic Acid Stain |
| SYTO 83 | 543 | 559 | Nucleic Acid Stain |
| SYTO 84 | 567 | 582 | Nucleic Acid Stain |
| SYTO 85 | 567 | 583 | Nucleic Acid Stain |
| SYTOX Blue | 445 | 470 | Nucleic Acid Stain |
| SYTOX Green | 504 | 523 | Nucleic Acid Stain |
| SYTOX Orange | 547 | 570 | Nucleic Acid Stain |
| Tetracycline | 390-425 | 525-560 | r |
| Tetramethylrhodamine (TRITC) | 555 | 576 | r |
| Texas Red™ | 595 | 620 | r |
| Texas Red-X™ conjugate | 595 | 615 | r |
| Thiadicarbocyanine (DiSC3) | 651, 653 | 674, 675 | r |
| Thiazine Red R | 596 | 615 | r |
| Thiazole Orange | 510 | 530 | r |
| Thioflavin 5 | 430 | 550 | r |
| Thioflavin S | 430 | 550 | r |
| Thioflavin TCN | 350 | 460 | r |
| Thiolyte | 370-385 | 477-488 | r |
| Thiozole Orange | 453 | 480 | r |
| Tinopol CBS (Calcofluor White) | 390 | 430 | r |
| TMR | 550 | 573 | r |
| TO-PRO-1 | 515 | 531 | r |
| TO-PRO-3 | 644 | 657 | r |
| TO-PRO-5 | 747 | 770 | r |
| TOTO-1 | 514 | 531, 533 | r |
| TOTO-3 | 642 | 660 | r |
| TriColor (PE-Cy5) | (488) 650 | 667 | r |
| TRITC TetramethylRodamineIsoThioCyanate | 550 | 573 | r |
| True Blue | 365 | 425 | r |
| TruRed | 490 | 695 | r |
| Ultralite | 656 | 678 | r |
| Uranine B | 420 | 520 | r |
| Uvitex SFC | 365 | 435 | r |
| wt GFP | 395 (475) | 508 | wild type GFP |
| WW 781 | 605 | 639 | r |
| X-Rhodamine | 580 | 605 | r |
| XRITC | 582 | 601 | r |

TABLE 1A-continued

| Fluorophore | Absorption | Emission | Other info |
|---|---|---|---|
| Xylene Orange | 546 | 580 | r |
| Y66F | 360 | 508 | r |
| Y66H | 360 | 442 | r |
| Y66W | 436 | 485 | r |
| Yellow GFP | 513 | 527 | Yellow shifted Green Fluorescent Protein |
| YFP | 513, 520 | 527, 532 | Yellow Fluorescent Protein |
| YO-PRO-1 | 491 | 506 | r |
| YO-PRO-3 | 613 | 629 | r |
| YOYO-1 | 491 | 508, 509 | r |
| YOYO-3 | 612 | 631 | r |

TABLE 1B

Exemplary Chemiluminophores and Pre-chemiluminophores 9,10-Diphenylanthracene (DPA)
1-chloro-9,10-diphenylanthracene (1-chloro(DPA))
2-chloro-9,10-diphenylanthracene (2-chloro(DPA))
9,10-Bis(phenylethynyl)anthracene (BPEA)
1-Chloro-9,10-bis(phenylethynyl)anthracene
2-Chloro-9,10-bis(phenylethynyl)anthracene
1,8-dichloro-9,10-bis(phenylethynyl)anthracene
2,4-di-tert-butylphenyl 1,4,5,8-tetracarboxynaphthalene diamide
Rhodamine B
5,12-Bis(phenylethynyl)naphthacene
Violanthrone
16,17-(1,2-ethylenedioxy)violanthrone
16,17-dihexyloxyviolanthrone
16,17-butyloxyviolanthrone
N,N'-bis(2,5,-di-tert-butylphenyl)-3,4,9,10-perylenedicarboximide
1-N,N-dibutylaminoanthracene
6-methylacridinium iodide
luminol In some examples, the chemiluminophore is a luminescent platinum group metal complex with one or more α-diimine ligands, for example, ruthenium (II) diamine complexes (e.g., ruthenium(II) tris(2,2'-bipyridyl); ruthenium(II) tris(1,10-phenanthroline), and ruthenium(II) tris(4,70diphenyl-1,10-phenantroline). Alternatively, the chemiluminophore can be a platinum (II) porphyrin, such as platinum(II) octaethylporphyrin or platinum(II) tetrakis (pentafluorophenyl)porphyrin; a palladium(II) porphyrin such as palladium(II) octaethylporphyrin; a cyclometalated iridium (III) coumarin complex, a luminescent lanthanide complex, such as europium (III) complex or terbium (III) complex, or a quantum dot.

When a chemiluminophore such as a fluorophore is used, absorptive species generated therefrom can be monitored by irradiation with light of the proper wavelength or by a radiative transfer of energy such as FRET, which would allow for a chemiluminescent species (e.g. bis-(3,4,6-trichloro-6-(pentyloxycarbonyl)phenyl)oxalate, bis(2,4,6-trichlorophenyl) oxalate, bis(2,4-dinitrophenyl) oxalate, divanillyl oxalate) to excite a fluorophore such that no input light would be needed. Additionally oxygen donors or acceptors (e.g. hydrogen peroxide, potassium monoperoxysulfate, sodium borohydride) may be present. In some embodiments, the chemiluminophore used in the assay methods described herein is a precursor of an absorber and/or chemiluminophore, which is a molecule that converts to a compound which releases a detectable signal via a physical or chemical reaction. An absorber and/or chemiluminophore precursor may be a precursor species that reacts to yield fluorescent or absorbent species upon release (e.g., at suitable pH value). Examples include, but are not limited to, acylated fluorescein derivatives, acylated SNARF derivatives, acylated BCECF derivatives, or acylated rhodamine derivatives. For example, the precursor can be fluorescein dilaurate, fluorescein diacetate, mono-iodinated BODIPY.

When placed in a solution having a suitable pH value (containing a suitable acidic or basic pH modulator), the precursor may convert to a chemiluminescent, fluorescent or absorbent species, which is capable of releasing a detectable signal. An energy source such as heat may be used to increase the rate of the conversion, which leads to a signal change (fluorescence increase or decrease or absorbance increase or decrease). In other examples, the chemiluminescent or absorbent precursor can be a precursor that yields a fluorescent or absorbent molecule by stoichiometric reaction with an oxidizing agent, reducing agent, and/or a metal. Conversion of the precursor molecule to the fluorescent or absorbent molecule can be performed in a suitable solution (e.g., aqueous based), which may comprise an oxidant, a reductant, and/or a metal. Examples include hydrogen peroxide, hypochlorous acid, sodium hypochlorite, hydrogen sulfide, dithianes, thiols, glutathione, ozone, acetylcysteine, Hg(II), Cu(II), Cu(I), or Co(II).

For exemplary absorbers and precursors thereof for use in the assay methods described herein, see Dogeigne and Lejeune, Talanta 5 (2000) p 425, the examples of chemiluminescent species disclosed therein are incorporated by reference. Examples include luminol ($C_8H_7N_3O_2$) and its derivatives, bis(2,4,5-trichlorophenyl-6-carbopentoxyphenyl)oxalate and its derivatives, acridinium and its derivatives, dioxetane and its derivatives, substituted aryl oxalates, coelenterazine and its derivatives, peroxyoxalic derivatives, and Ruthenium(II) complexes such as tris(2,2'-bipyridine).

Additionally the presence of an enhancer (e.g. sodium hydroxide, hydrochloric acid, surfactants) may improve the signal (e.g. detection or longevity).

E. Surface of Nanoparticles

In some embodiments, the nanoparticle as described herein contains at least one functional outer surface that may coat the particle core. This functional outer surface may or may not contain distinct chemical species from the core of the nanoparticle, the signaling agent and/or the matrix. It may contain chemical species for controlling nanoparticle formation, nonspecific binding, or association of the binding agent. This surface may be multiple layers and may be comprised of one or more classes of molecules:

Class 1: Surfactants. Examples of the surfactants include, but are not limited to, Brijs, Spans, Polysorbates, Tritons, Igepals, Pluoronics, Poloxamers, Tergitol, Cremophor, cylodextrins, lecithin, glyceryl monostearate, glyceryl monooleate, glyceryl monothioglycolate, glyceryl monocaprylate, glyceryl monolaurate, sodium dodecyl sulfate, sodium cholate, sodium deoxycholate, Adogen 464, lauryl dimethyl amine oxide, cetyltrimethylammonium bromide, methylbenzethonium chloride, 1,2-distearoyl-sn-glycero-3-phosphoethanolamine (DSPE) conjugates with PEG, DSPE conjugates with dextran, lipid-PEG conjugates, lipid-dextran conjugates, lipid-protein conjugates, lipid-peptide conjugates, lipid-nucleic acid conjugates, cholesterol-PEG conjugates, cholesterol-dextran conjugates, cholesterol-protein conjugates, cholesterol-peptide conjugates, cholesterol-nucleic acid conjugates, or a combination thereof. Selection of surfactant molecular weight and hydrophile-lipophile balance (HLB) value may help control nanoparticle size, shape, nonspecific binding, and/or specific association of the binding agent, as is known to those skilled in the art.

Class 2: Surfactants with chemical moieties to which covalent bonds may be formed. The "active" chemical moieties (ACMs) may include, but are not limited to, amine, carboxylic acids, thiol, azides, alkynes, Ni, histidines, Cu, lysines, maleimide, NHS-ester, biotin, avidin, tetrazene, 1,2,4-triazine, or a combination thereof. Examples of these surfactants include, but are not limited to, fatty acids (linoleic acid, palmitic acid, etc.), NHS esters of fatty acids, DSPE-PEG-ACM conjugates, DSPE-dextran-ACM conjugates, lipid-PEG-ACM conjugates, lipid-dextran-ACM conjugates, or a combination thereof. The ACMs may be used for specific interactions, including covalent bonds, with one or more binding agents.

Class 3: Core species with surfactant functionality. The chemical species that comprise the signaling agents and/or the matrices of the nanoparticles may have surfactant activity. Examples include, but are not limited to, lipid conjugates of chemiluminophores (fluorescein dilaurate, rhodamine hexadecyl ester, rhodamine oxadecyl ester, etc.), hydrophobic-hydrophilic block- or co-polymers (PLGA-polylysine, PLA-polylysine, etc.), hydrophobic polymers with hydrophilic pendant groups, etc.

Figure 12A:
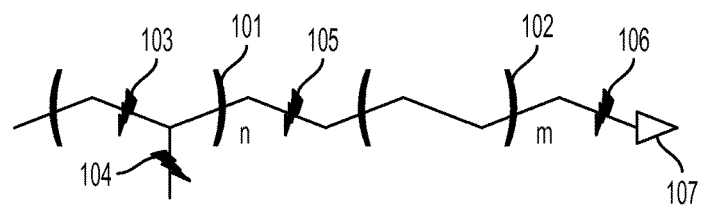
FIGS. 12A-12D include diagrams illustrating exemplary designs of nanoparticles comprising signaling agents (payloads).

FIGS. 12A-12D illustrate certain exemplary designs of the nanoparticles. In one example, the core of the nanoparticles may be polymeric or particulate in nature. Polymers consist of repeating units containing one or more signaling agents (101) and may release the signaling agents (payloads) by severing pendant (104) and/or backbone (103 and 105) groups. Multiple different signaling agents may be contained in a single polymer. Polymers may consist of co-, alt-, branched-, or similar and/or hybrid structures. Structural pieces may contain non-payload elements (102), which may be present for stability or similar functional purposes. Each polymer may be bound to one or more detection species (107). FIG. 12A.

Figure 12B:
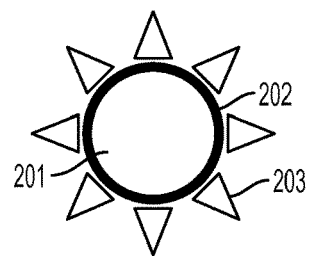
Figure 12C:
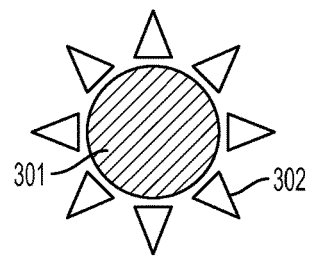
Figure 12D:
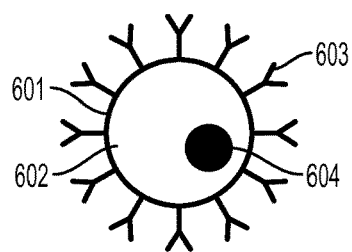

The particles may consist of homo- or heterogeneously distributed payloads. Homogeneous particles (301) may consist of distributions of payload particles in one or more of a polymer, small molecule, and/or crystalline matrix. Heterogeneously distributed payloads may consist of one or more core-shell structures with payload(s) at the core (201) surrounded by one or more of a polymer, small molecule, and/or crystalline shell (202). One or more payloads may be present per particle. Particle surfaces may present one or more detection and/or stability-enhancing species (203 and 302). FIGS. 12B and 12C.

Magnetically active particles may be bound to polymers or embedded in particles in order to magnetically address the labels.

In some embodiments, the nanoparticle described herein may contain two different signaling agents, which, upon a reaction, produce different detectable signals. In one example, the nanoparticle contains one signaling agent for signal amplification (e.g., a catalyst) and another signaling agent that directly releases a signal (e.g., a fluorophore) after being released from the nanoparticle.

Binding Agent

In some embodiments, the nanoparticle described herein is associated (e.g., conjugated) to a binding agent, i.e., a molecule that binds to an analyte of interest. Binding agents may include, but are not limited to one or more of an antibody, antigen, enzyme, fibronectin, oligonucleotide, oligopeptide, oligosaccharide, nucleic acid, nucleotide, nucleoside, metabolite, lipid, fatty acid, glycolipid, sterol, glycerolipid, vitamin, hormone, neurotransmitter, DNA, RNA, including mRNA, rRNA, microRNA, small interfering RNA (siRNA), long noncoding RNA (lnc RNA), small nuclear RNA (snRNA), double stranded RNA (ds RNA) peptide nucleic acid (PNA), polymer nucleic acid, locked nucleic acid (LNA), cDNA, amino acid, protein, peptide, polypeptide, receptor, ligand, small molecule, aptamers, polysaccharides, plastibodies, other member of receptor-ligand pair, affibody, plastibody, camelid, or any selective detection materials disclosed herein. The ratio of the binding agent present on the nanoparticle, either in the polymer or on the particle surface, to the signaling agents may be tuned to optimize detection by conventional methods.

The nanoparticle can be associated to a binding agent via covalent interactions (e.g., conjugation), via non-covalent interactions (e.g., van der Waals, hydrogen bonding, hydrophobic and/or electrostatic interactions), or adsorption. In some embodiments, the non-covalent interactions comprise van der Waals, hydrogen bonding, or hydrophobic interactions. In other embodiments, the non-covalent interactions comprise electrostatic interactions. In some embodiments, the binding agent is associated with the nanoparticle via an interaction other than an electrostatic interaction. In still other embodiments, the nanoparticle comprises a covalent bond to a binding agent. For example, the nanoparticle can comprise polyethylene glycol (PEG) or dextran groups or a surface protein, such as albumin, comprising functional groups that can form a covalent bond to a binding agent.

In some embodiments, the binding agent can be an antibody specific to the analyte, a nucleic acid, which can be a single-strand DNA or RNA, or an aptamer. Alternatively, the binding agent can be a member of a receptor/ligand pair. Selection of a suitable binding agent would depend on the nature of the analyte of interest to be detected in the assay method described herein. For example, if the analyte is a nucleic acid, a nucleic acid having a sequence complementary to the target nucleic acid may be used as the binding agent. Alternatively, if the analyte of interest is a member of a receptor/ligand pair, the other member of the same receptor ligand pair may be used as the binding agent. A receptor/ligand pair can be any two binding partners that have specific binding activity to each other, for example, biotin/streptavidin.

In some examples, the binding agent specifically binds to the analyte. A binding agent that "specifically binds" (used interchangeably herein) to a target or an epitope thereof is a term well understood in the art, and methods to determine such specific binding are also well known in the art. An agent is said to exhibit "specific binding" if it reacts or associates more frequently, more rapidly, with greater duration and/or with greater affinity with a particular target analyte than it does with alternative targets. A binding agent "specifically binds" to a target analyte if it binds with greater affinity, avidity, more readily, and/or with greater duration than it binds to other substances. It is also understood by reading this definition that, for example, an agent that specifically binds to a first target analyte may or may not specifically or preferentially bind to a second target analyte. As such, "specific binding" or "preferential binding" does not necessarily require (although it can include) exclusive binding. Generally, but not necessarily, reference to binding means preferential binding.

In some embodiments, the binding agent is an antibody that binds to the analyte of interest. An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', $F(ab')_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

In some embodiments, an antibody may be considered a primary or secondary antibody. For example, a primary antibody may bind directly to, for example, a ligand such as an antigen or other protein; a secondary antibody may bind or be conjugated to a primary antibody or other binding agent or ligand and used for purposes of signal detection and amplification. In some embodiments, a single type of secondary antibody may bind to one or more types of primary antibodies. In some embodiments, detection of a signal may be based on detection of bound secondary antibody.

In some instances, the binding agent is modified by a molecule that allows for the attachment of the binding agent onto the nanoparticle. For example, the binding agent may be conjugated to biotin. Via biotin-streptavidin interaction, the biotinylated binding agent can be attached to the nanoparticle.

Assay Methods

The nanoparticles described herein may be used with multiple chemical and/or biochemical assay formats and/or platforms including, but not limited to, well-, microwell-, microfluidic-, gel-, magnetic particle-, solid chromatographic-based assay formats, for detecting and quantifying analytes of interest in a sample. Assay types may include, but are not limited to, sandwich, hybridization, competition, binding, solid chromatographic, and other assays. Assays may additionally be single-plex or multi-plex assays. Assays suitable for the invention can be any assays that determine, detect, and/or measure absolute and/or relative signal of or from one or more signaling agents (from one or more reactions that produce one or more measurable signals). In some embodiments, assays may be high-throughput assays, multiplex assays, point of care (POC) assays, or lateral flow assays. In some embodiments assays may include simultaneous or sequential measurement and/or detection of one or more analyte.

Figure 13A:
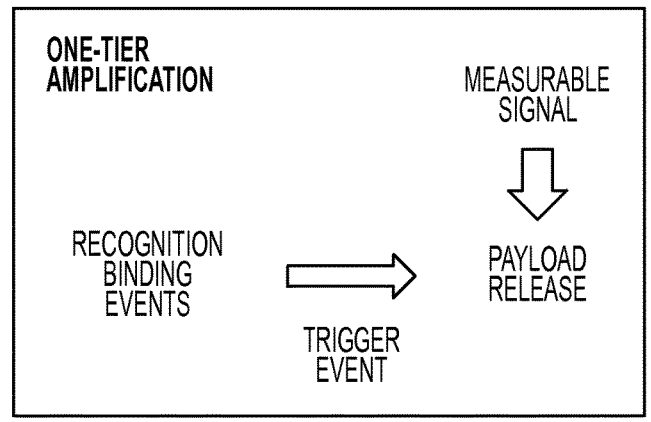
FIGS. 13A and 13B include diagrams showing two different amplification assay formats.

Depending upon the type of the signaling agent used in the nanoparticles, the nanoparticle assay may be a one-tier amplification assay or a two-tier amplification assay, as defined in FIG. 13. The ratio of the number of payload species to binding events dictates the amplification of the signal, termed a "one-tier" amplification (401). FIG. 13A. Examples include the release of specific ions that can be electrically or optically detected including, but not limited to, $F^-$, $Cu^+$, $Cu^{2+}$, $Fe^{3+}$, $Fe^{3+}$, $NO_3^-$, $SO_4^{2+}$, $NH_4^+$, $Hg^{2+}$, $Ti^{2+}$, $Ti^{4+}$, $S^-$, $Ca^{2+}$, $H^+$, $Au^{2+}$, $Ag^+$, $Pd^{2+}$, $Pt^{2+}$, etc. In order to enhance optical detection, ions may complex with species in the solution, such as the aqueous cupric ammonium ion.

Figure 13B:
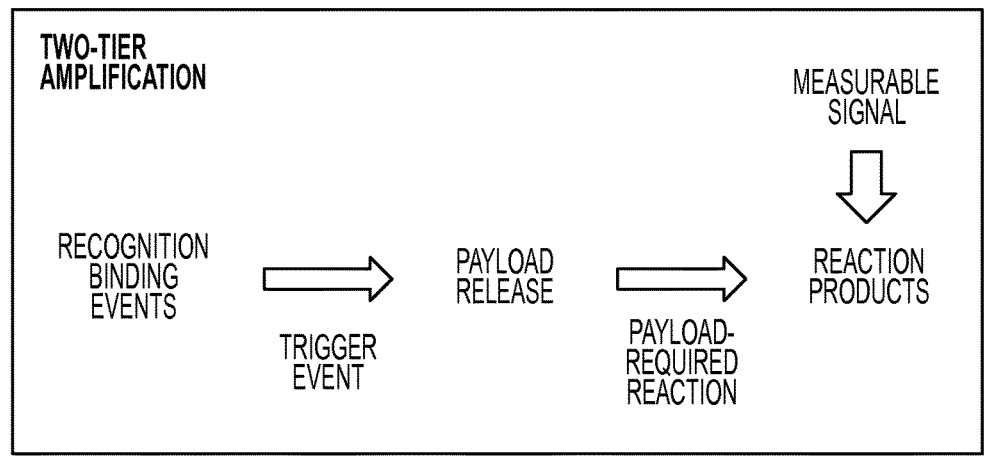

The signaling agent may also participate in one or more reactions that produce one or more measurable signals. The signals may be optical, electrical, magnetic, acoustic, or other. The payloads may be reagents or catalysts in the reaction(s) that produce the signals, with catalysis the preferred mode of operation. They may be molecular, ionic, or particulate in nature. The signaling agent may result in a reaction that either increases or decreases the measured signal. Examples of reactions include, but are not limited to, oxidation, reduction, addition, elimination, polymerization, and/or rearrangement chemistries. The signal amplification may thus be two-fold or "two-tier" (501): the first level is based on the ratio of the number of payload species to binding events and the second level is based on the reaction (s) in which the payload species participate. FIG. 13B. The addition of a "stop chemistry" may be required to terminate the reaction for optimal detection.

Nanoparticles with signaling agents that produce one- and/or two-tier amplifications may require reagents to be added to the sample undergoing testing. These reagents may be added before, during, or after the biochemical binding event(s). In order to control the timing of the onset of the reaction, one or more reagents may be contained in an inactive state, such as protected in a particle or polymer, until the onset of a defined trigger. Suitable triggers are the same as those that release signaling agents. Such "reagent vessels" may contain surface molecules that participate in the biochemical binding event(s). They may also contain magnetic particles to enable magnetically-driven assay control.

Multiple assays may be run in parallel and/or serially. Control assays may validate assay performance and/or provide and/or enhance quantification. Species other than the "detection species," termed "tracers," may be present for these controls.

Assay and/or particle design may also enable multiplexed detection to be performed. Labels may respond to similar or different triggers, may containing similar or different payloads, and/or may contain similar or different tracers. For bead-based assays, tracers may be present on beads that participate in the assays. Tracers may be used to tune the number of labels available.

Any of a variety of samples may be suitable for use with methods disclosed herein including, but not limited to biological samples and chemical or recombinant preparations.

Generally, any biological samples containing biomolecules (e.g., cells, tissue, etc.) may be used. Biological samples may be samples from any living organism, including, but not limited to animals and/or humans. Types of biological samples include, but are not limited to, cells, cell lysate, FFPE (FASP Protein Digestion) digests, tissues including tissue biopsies or autopsy material, whole blood, plasma, serum, urine, stool, saliva, cerebrospinal fluid, cord blood, chorionic villus samples amniotic fluid, and transcervical lavage fluid. Cell cultures of any of the aforementioned biological samples may also be used in accordance with inventive methods, for example, chorionic villus cultures, amniotic fluid and/or amniocyte cultures, blood cell cultures (e.g., lymphocyte cultures), etc.

In some embodiments, biological samples comprise diseased cells such cancer or tumor cells. In some embodiments, biological samples are prenatal samples. Thus, a typical biological sample suitable for the present invention contain heterogeneous biomolecules. In some embodiments, a biological sample contains a mixture of biomolecules from different cell types (e.g., normal cells and diseased cells such as tumor cells). In some embodiments, a biological sample (e.g., blood, serum or plasma) contains a mixture of maternal biomolecules and fetal biomolecules. Suitable samples may be unpurified or minimally purified biological samples or may be made of isolated biomolecules, urine, or plasma/serum.

Sandwich Assays

In some embodiments, the assay methods described herein are carried out in a sandwich format, which is suitable for detecting a relatively large analyte, which allows for binding to two binding agents, such as two antibodies that bind to different epitopes of the analyte. Performing a sandwich assay typically involves at least one binding agent (e.g., an antibody) with specificity for an analyte of interest for detection (the detection agent). The sample with an unknown amount of the analyte can be immobilized on a solid support (e.g., a polystyrene microtiter plate, a microparticle, a magnetic microparticle) either non-specifically (via adsorption to the surface) or specifically (via a capture agent that specifically binds the analyte, such as an antibody, or a covalent linkage). After the analyte is immobilized, the detection agent is added, forming a complex with the analyte. The detection agent can be covalently linked to the nanoparticle as described herein. Between each step, the solid support such as the plate is typically washed with a mild detergent solution to remove any agent such as antibodies that are non-specifically bound. After the final wash step, the nanoparticle can be dissociated as described herein to release the signaling agent, which can be subjected to a reaction resulting in a signal change. The signal change indicates the presence and/or quantity of the analyte in the sample.

To perform the sandwich assay as described herein, a sample suspected of containing an analyte of interest can be incubated with a solid support, e.g., a microwell plate, on which a capture agent (e.g., an antibody specific to the analyte) is immobilized. The solid support can then be washed to remove free analytes. The nanoparticle, which is associated with a binding agent specific to the analyte, can be incubated with the solid support under suitable conditions allowing for the binding of the binding agent to the analyte of interest captured on the solid support. In some examples, both the capture agent and the binding agent attached to the nanoparticles are antibodies which bind to different epitopes of the analyte. After removal of any free nanoparticles from the mixture, the nanoparticles captured on the solid support (via binding to any analyte of interest captured on the solid support) are dissociated by a suitable trigger (e.g., a chemical trigger, a physical trigger, or a combination thereof) to release the signaling agent entrapped in the nanoparticles.

Selection of a suitable trigger would depend on the type of nanoparticles used in the assay, which is within the knowledge of those skilled in the art. For example, if the nanoparticle contains a hollow core having air or liquid, ultrasound can be used to dissociate such nanoparticles. In another example, if the nanoparticle contains a dopant, a physical trigger (e.g., light or heat) and/or a chemical trigger (e.g., solvent or pH) can be used to dissociate the nanoparticles. Provided below is a table showing exemplary release designs and conditions that may be needed for dissociating the nanoparticles:

TABLE 2

Exemplary Triggers for Dissociation of Nanoparticles

| Release design | Energy required for release | Solution components required for release |
|---|---|---|
| Thermal | Heat - may be conductive, radiative, convective | Any solvent may be used |
| Chemical | Not required, though heat may be used to enhance degradation reaction | Presence of solvent, which may be pH-tuned, directly degrades NP, releasing cargo |
| Thermal + chemical | Heat - may be conductive, radiative, convective | Specific solubilizing solvent for NP must be present - for example organic component such as IPA, EtOH, DMSO must be added |
| Light + chemical | Light - likely in UV region degrades NP backbone or component in NP | Solvent required to solubilize degraded NP components, which may be pH-tuned aqueous-based |
| Light + thermal + chemical | | Essentially thermally-enhanced light + chemical to speed degradation |

After dissociation of the nanoparticles, the signaling agent entrapped therein can be released, preferably in a solution in which the signaling agent, as well as other components for a reaction involving the signaling agent as described herein, is soluble. The solution can be a homogenous solvent or a mixture of one or more solvent and/or one or more solutes. When a chemical trigger (e.g., an acid, base, catalyst, enzyme, solvent) is used to dissociate the nanoparticles, the chemical trigger can be placed in the solution.

Figure 4:
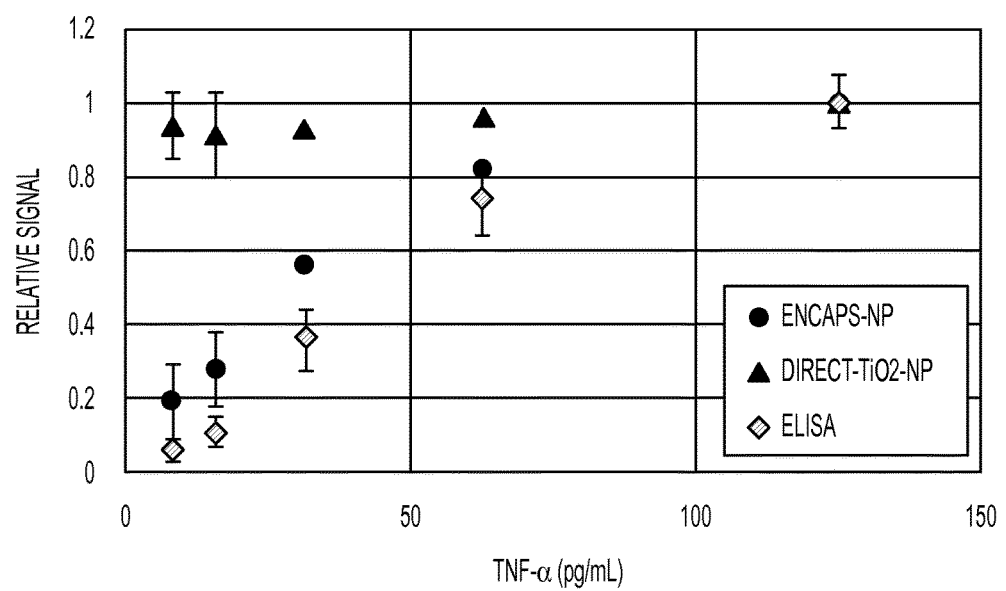
FIG. 4 compares a standard dilution series of a sandwich immunoassay for tumor necrosis factor-alpha (TNF-α) for 1) "Encaps-NP," nanoparticles encapsulating titania nanoparticles, 2) "Direct-TiO2-NP," titania nanoparticles directly functionalized to detection antibodies, and 3) "ELISA," a standard ELISA protocol (eBioscience). Note all data are normalized to a maximum detection signal of 1 and that the directly-functionalized titania detection limit cannot be determined due to the high errors and low dynamic range. This is in contrast to the nanoparticles encapsulating the titania, which offer enhanced sensitivity over the conventional ELISA: the nanoparticle limit of detection is 1.5 pg/mL in contrast to the 3.7 pg/mL level for the ELISA.
Figure 16A:
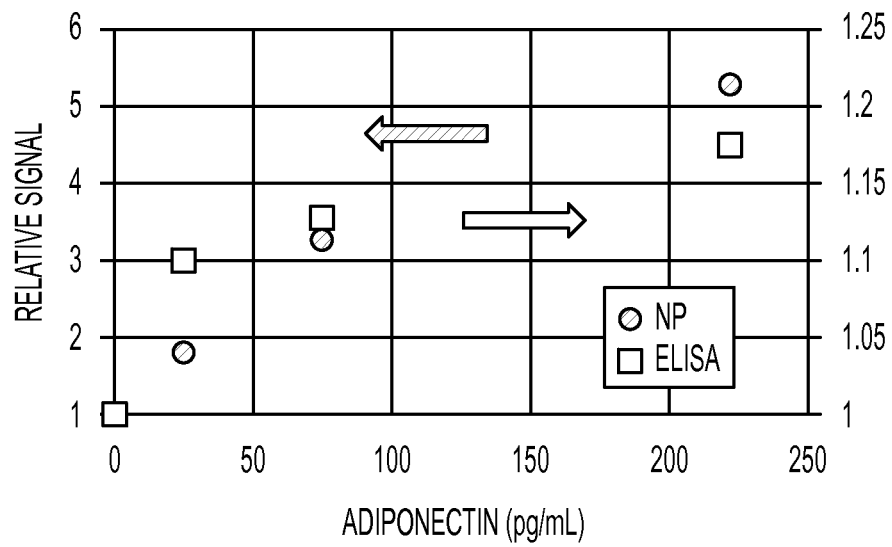
FIGS. 16A and 16B show a comparison of a nanoparticle-derived standard curve and a state-of-the-art ELISA (horseradish peroxidase, HRP)-derived curve for a sandwich adiponectin assay. The signaling agent is the pre-chemiluminophore fluorescein dilaurate. The significantly enhanced nanoparticle-derived signal lowers the limit of detection by ~3-fold compared with the ELISA standard, to ~8 pg/mL from ~25 pg/mL. Note that two vertical axes are required in FIG. 17A.
Figure 16B:
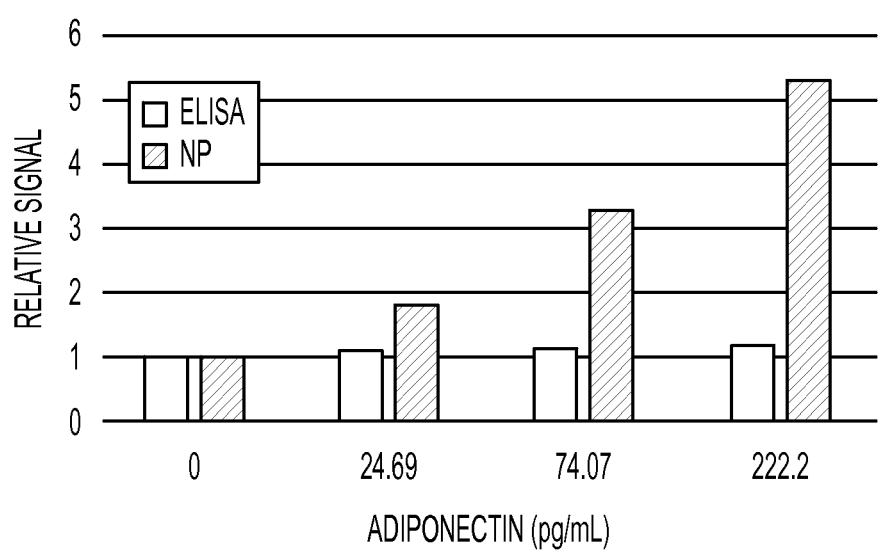

The signaling agent released into the solution may produce a detectable signal or mays then be subject to a reaction to produce a product that is capable of releasing a detectable signal. The reaction can be any event that changes the physical or chemical property of one molecule (which can be the signaling agent itself), resulting in a signal change as described herein. In some embodiments, components required for occurrence of the reaction, e.g., substrates of a catalyst, fluorophore precursors, oxidants, reductants, pH modulators, substances to enhance the reaction or signal detection, as described herein may be contained in the same solution. Thus, the step of releasing the signaling agent from the nanoparticles and, in certain cases, the step of subjecting the agent to a reaction to produce a detectable signal can take place simultaneously. The signal change can be determined by a conventional method, e.g., an optical method or an electrical method. Based on the signal change, the presence or quantify of the analyte of interest can be measured. Results of sandwich nanoparticle assays are shown in FIGS. 4 and 16A-16B.

Competition Assays

In some embodiments, the assay methods described herein are carried out through competitive binding, which is suitable for, e.g., detecting small analytes.

The competitive assay may be performed by incubating a sample suspected of containing an analyte of interest with a binding agent specific to the analyte to form a binding agent/analyte complex, the binding agent being conjugated to the nanoparticles as described herein. Typically, the binding agent-nanoparticle conjugate is in excess relative to the analyte in the sample. (The more analyte in the sample, the less unbound nanoparticle remains. Thus, the amount of the unbound nanoparticle is inversely proportional to the amount of the analyte in the sample.) The mixture is then incubated with a solid support on which the analyte is immobilized under conditions allowing for the binding of the unbound nanoparticle to the immobilized analyte. The solid support can be washed after the incubation to remove unbound substances. The nanoparticle that is bound to the solid support is then dissociated as described herein to release the signaling agent contained therein following the descriptions provided herein. The signaling agent can then be subject to a reaction as described herein to produce a signal change, based on which the presence and/or quantity of the analyte in the sample.

Alternatively, a competitive assay can be performed as follows. A sample suspected of containing an analyte of interest is incubated with a solid support under conditions allowing for immobilization of the analyte onto the solid support. The solid support is washed to remove unbound substances and is then incubated with both a free binding agent specific to the analyte and nanoparticles as described herein, on which a binding agent specific to the analyte is attached. The binding agent attached to the nanoparticles may be the same as or similar to the free binding agent. The free binding agent and the nanoparticle-bound binding agent compete against each other for binding to the analyte immobilized on the solid support. After being washed to remove any unbound substances, the nanoparticles bound to the solid support can be dissociated following methods described herein to release the signaling agent contained in the nanoparticles. The signaling agent may produce a signal change or may then be subject to a reaction as described herein to produce a signal change, based on which the presence and/or quantity of the analyte in the sample.

In other embodiments, a competitive assay may comprise nanoparticles on which an analyte of interest or a member of a receptor/ligand pair (e.g., biotin) is attached. To perform the assay, a solid support on which a binding agent such as an antibody that is specific to the analyte is immobilized is provided. The solid support is incubated with a sample suspected of containing an analyte of interest in the presence of the nanoparticle on which the analyte is attached. The incubation is carried out under suitable conditions allowing for binding of the binding agent on the solid support to the analyte in the sample and that on the nanoparticles. The analyte attached to the nanoparticle competes against the free analyte in the sample for binding to the binding agent on the solid support. After the incubation, the solid support can be washed to remove unbound substances. The nanoparticles bound to the solid support can be dissociated following methods described herein to release the signaling agent contained in the nanoparticles. The signaling agent can then be subject to a reaction as described herein to produce a signal change, based on which the presence and/or quantity of the analyte in the sample.

Figure 2:
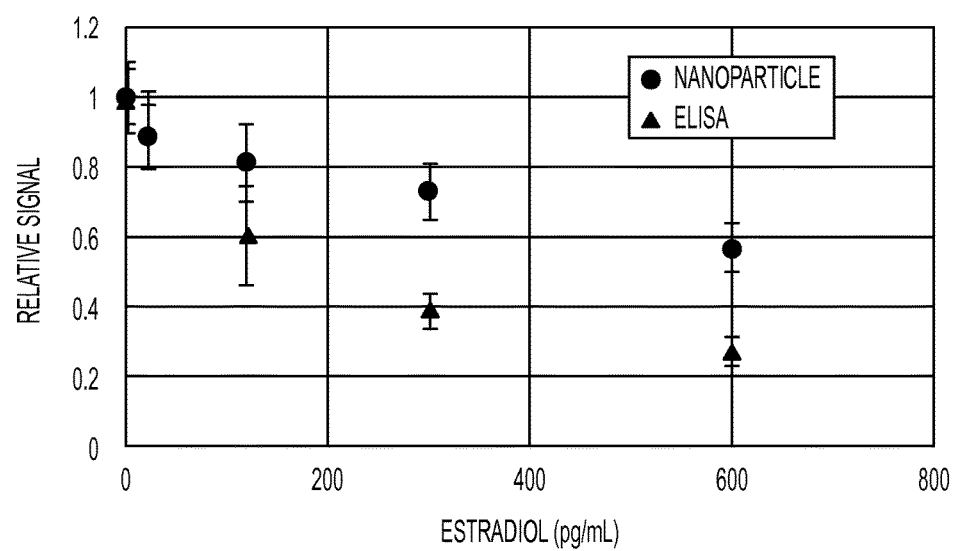
FIG. 2 shows a comparison of a nanoparticle-derived standard curve and a state-of-the-art ELISA (horseradish peroxidase, HRP)-derived standard curve for a competitive estradiol assay. The signaling agent in the nanoparticles is titania nanoparticles, which create the observed signal by catalyzing a light-induced redox reaction. The use of a light-driven reaction obviates the need to add a separate "stop" solution, which is required for standard ELISA assays. The error bars show standard deviation. The signals are normalized to 1 at the 0 free estradiol concentration (competitive assay).
Figure 21:
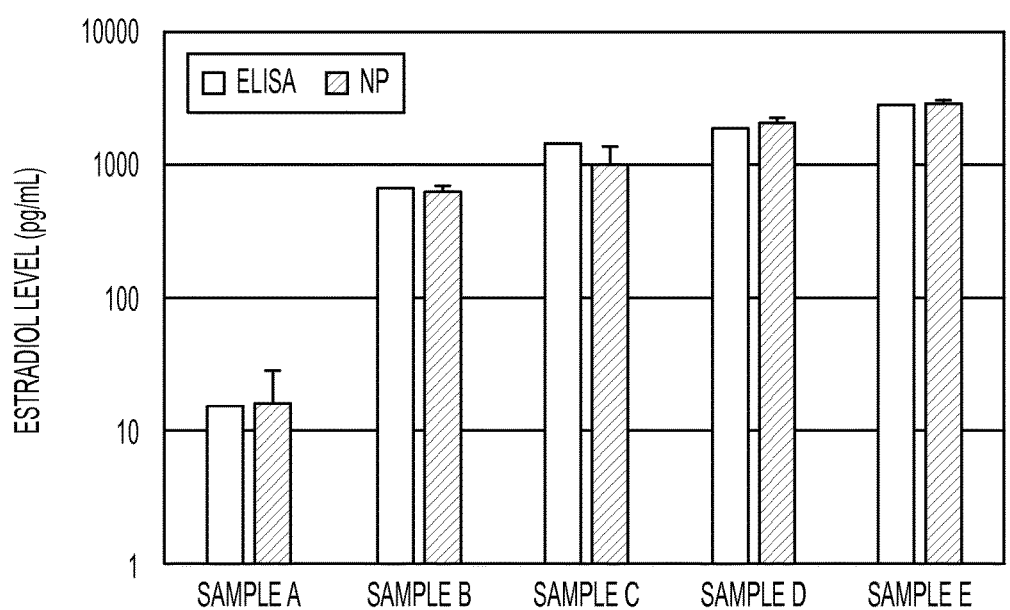
FIG. 21 demonstrates the ability of the nanoparticles from Example 3 used with five human blood samples to detect estradiol in a competitive assay format. The results are compared with clinical values from an automated chemiluminescent ELISA-based system, the Roche Cobas E411.

Alternatively, the solid support can be incubated with a sample suspected of containing the analyte of interest and a conjugate comprising the analyte and a member of a receptor/binding pair (e.g., biotin or streptavidin) under suitable conditions allowing for the formation of binding agent/analyte complex. The solid support can be washed to remove unbound substances and then be incubated with nanoparticles on which an agent that binds (directly or indirectly) the analyte conjugate is attached. For example, both the analyte conjugate and the nanoparticle may be biotinylated and the incubation is carried out in the presence of streptavidin, which bridges the binding of the analyte conjugate and the nanoparticle. After the incubation, the solid support is again washed for multiple times to remove unbound substances. The nanoparticles bound to the solid support can be dissociated following methods described herein to release the signaling agent contained in the nanoparticles. The signaling agent may produce a signal change or may then be subject to a reaction as described herein to produce a signal change, based on which the presence and/or quantity of the analyte in the sample. Results of sandwich nanoparticle assays are shown in FIGS. 2 and 21.

Assays in Other Formats

In addition to sandwich and competitive formats, the assay methods described herein can also be performed in other formats as known in the art or disclosed herein.

For example, the assay methods may be performed in a manner similar to a direct ELISA or ELISPOT as follows. A sample suspected of containing an analyte of interest can be incubated with a solid support under conditions allowing for the immobilization of the analyte onto the solid support. After being washed to remove unbound substances, the solid support is incubated with a nanoparticle as described herein on which a binding agent specific to the analyte is attached to allow for binding of the nanoparticle (via the binding agent) to the immobilized analyte. The solid support is then washed again to remove unbound substances. The nanoparticles bound to the solid support can be dissociated following methods described herein to release the signaling agent contained in the nanoparticles. The signaling agent can then be subject to a reaction as described herein to produce a signal change, based on which the presence and/or quantity of the analyte in the sample.

In another example, the assay method may be performed in a solid chromatographic (e.g. lateral flow) assay format. Such an assay may be carried out on a solid support (e.g., a membrane). The solid support may be made by a suitable material that allows for movement of biomolecules along the solid support. Examples include, but are not limited to, nitrocellulose, nylon, cellulose, polyvinylidine fluoride (PVDF), polycarbonate, polypropylene, polyethylene, Teflon, and Kevlar. To perform the assay, a sample suspected of containing an analyte of interest can be placed at one end of the solid support. Upon moving along the solid support, the analyte in the sample binds any of the nanoparticles as described herein to form a complex. The complex can then be captured by a capture agent which is immobilized at a specific zone of the solid support. Upon washing, the nanoparticles are dissociated as described herein to release the signaling agent contained therein. Reagents needed for signal generating mediated by the signaling agent can be entrapped in microparticles, which are immobilized either at the zone as the capture agent or at a nearby zone such that the signaling agent, upon release, can enter into the microparticles for signal production. The reagents contained in the microparticles depend on the signaling agent used in the nanoparticles. For example, if the signaling agent is a catalyst, a suitable substrate, as well as other relevant components as described herein, can be contained in the microparticles.

In another example, the assay method may be performed using e.g. immunoblot (Western blot) analysis. Such an assay may be carried out on one or more solid supports (e.g., a polyacrylamide gel and/or a membrane). The solid supports may be a first and a second solid support. The first solid support may be made by a suitable material (e.g. polyacrylamide gel) that allows for movement of biomolecules along and through the solid support, wherein the movement is caused by application of electrical current (i.e. gel electrophoresis). The second solid support may be made by a suitable material that allows for transfer of biomolecules from a first solid support onto a second solid support by applying current to cause the transfer of material from the first solid support onto the second solid support. Examples include, but are not limited to, nitrocellulose, nylon, cellulose, polyvinylidine fluoride (PVDF), polycarbonate, polypropylene, polyethylene, Teflon, and Kevlar. In the assay, the first solid support is used prior to the second solid support (i.e. the first and second solid supports are used sequentially, beginning with the first solid support. To perform the assay a sample suspected of containing an analyte of interest can be placed at one end of the first solid support. Upon moving along and through the solid support, the sample suspected of containing the analyte is separated along the solid support such that the separate portions of the sample are present on the first solid support in decreasing order of molecular weight. The separated portions are transferred from the first solid support onto the second solid support by applying electrical current. The second solid support containing the portions of the separated sample is then assayed. The assay consists of exposing the second solid support containing the portions of the separated sample to any of the nanoparticles as described herein, wherein the sample suspected of containing an analyte of interest can bind to form a complex with the nanoparticles. The complex can then be captured by a capture agent which is immobilized at locations wherein the nanoparticles are bound to the analyte of interest on the second solid support. Upon washing, the nanoparticles are dissociated as described herein to release the signaling agent contained therein. As described herein the released signaling agent may produce a detectable signal directly or through a reaction.

In some embodiments, nanoparticles containing two different signaling agents are used for detecting/quantifying an analyte of interest in samples in different concentrations so as to obtain accurate results. For example, nanoparticles containing a catalyst and a fluorophore as the signaling agents can be used. When a sample contains a low amount of the analyte, signal amplification may be needed. In that case, the catalyst is used to amplify the signal for detecting the analyte following the procedures described herein. On the other hand, if the sample contains a relative high amount of the analyte, the fluorophore can be used for detecting/quantifying the analyte in the sample.

In other embodiments, an assay method described herein involves the use of two or more nanoparticles for detecting/quantifying two or more analytes in a sample. The two or more nanoparticles are conjugated to binding agents targeting different analytes of interest. Further, the two or more nanoparticles contain signaling agents, which upon reactions, produce different signals (e.g., green fluorescence or red fluorescence; or two different nucleic acids), which can be relied on for detecting or quantifying different analytes. In some examples, the two or more nanoparticles can be made by the same or similar materials such that they can be dissociated by the same trigger (e.g., a physical trigger or chemical trigger). In some examples, the two or more nanoparticles can be made by materials such that they can be dissociated by different triggers (e.g., a physical trigger or chemical trigger).

Kits for Performing Assay Methods Described Herein

The present disclosure also provides kits for use in performing the assay methods described herein. The kit may further comprise components for performing a reaction in the presence of the signaling agent to produce a product, which results in a signal change. In some embodiments, the kit may comprise two or more nanoparticles comprising different signaling agents and binding agents specific to different analytes.

The kit disclosed herein may further comprise relevant components in connection with the different assay format as described herein. For example, a kit for performing the assay method in Sandwich format may further comprise a binding agent specific to the same analyte as the binding agent attached to the nanoparticles. The binding agent may be in free form or immobilized on a solid support. The binding agent and that attached to the nanoparticles may bind to different epitopes of the same analyte.

In other embodiments, kit for performing the assay method in competitive assay format may further comprise a binding agent specific to the analyte, wherein the binding agent is either in free form or immobilized on a solid support and a conjugate comprising the analyte and molecule that can bind the nanoparticles. Alternatively, the kit may further comprise the binding agent in free form and optionally a solid support for immobilizing the analyte in the sample. The free binding agent may be the same as the binding agent on the nanoparticle or may compete against the binding agent on the nanoparticle for binding to the analyte. In another example, the kit may further comprise the analyte either in free form or immobilized on a solid support.

In other embodiments, the kit may comprise a nanoparticle with a surface comprising one or more functional groups, to which a binding agent may be adhered.

In yet other embodiments, the kit comprises a membrane suitable for a lateral flow assay, on which necessary components (e.g., those described herein) are immobilized.

In some embodiments, the kit can further comprise instructions for use in accordance with any of the methods described herein. The included instructions can comprise a description of performing each step of the assay method. The kit may further comprise a description of selecting suitable samples to be analyzed by the assay method.

The kits provided herein are in suitable packaging. Suitable packaging includes, but is not limited to, vials, bottles, jars, flexible packaging (e.g., sealed Mylar or plastic bags), and the like. Also contemplated are packages for use in combination with a specific device, including any spectrometer, fluorescence spectrophotometer, and/or luminometer. These include 6-, 12-, 48-, 96-, 384-well benchtop microplate readers offered by multiple vendors (e.g. Perkin-Elmer, Molecular Devices), benchtop devices (e.g. Abbott, Alere, BioMerieur), automated devices (e.g. Siemens, Roche).

Kits may optionally provide additional components such as buffers and interpretive information. Normally, the kit comprises a container and a label or package insert(s) on or associated with the container. In some embodiments, the present disclosure provides articles of manufacture comprising contents of the kits described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1—Competitive ELISA

The PEG-palmitic acid (PEG-PA) conjugate was synthesized by dissolving 0.018 g of the N-hydroxysuccinimidyl ester of palmitic acid and 0.1 g of methoxypolyethylene glycol amine (2000 g/mol) in 2 mL tetrahydrofuran and stirring at room temperature for 4 hours. The PEG-PA conjugate was used without further purification.

The biotin-PEG-PA conjugate was synthesized by dissolving 0.017 g of the N-hydroxysuccinimidyl ester of palmitic acid and 0.1 g of poly(ethylene glycol) 2-aminoethyl ether biotin (2300 g/mol) in 2 mL tetrahydrofuran and stirring at room temperature for 2 hours. The biotin-PEG-PA conjugate was used without further purification.

The biotin-functionalized nanoparticles were synthesized as follows:
  Solution A was made by dissolving 2 g of Tween 80 in 100 mL of deionized water (DI). This solution was stirred at 70° C.
  Solution B was made by dissolving 0.125 g of Span 60 and 0.375 g of synthetic beeswax in 1 mL of mineral spirits at 70° C. After melting and dissolution, 0.1 mL of a 10 mg/mL dispersion of W-doped anatase $TiO_2$ nanoparticles (avg. diam. ~8 nm) in methanol were added. The solution was vigorously stirred with an open top to enable the methanol to evaporate. After 30 minutes, 0.001 mL of the biotin-PEG-PA conjugate and 0.004 mL of the PEG-PA conjugate were added.
  Solution B was then added to Solution A and the resulting emulsion was stirred at 10,000 rpm with a homogenizer. After 1 minute of stirring, the beaker containing the emulsion was put on ice and stirring continued for 3 hours.

The nanoparticles were characterized by dynamic light scattering (Malvern ZetaSizer), which showed a mean particle size of 153 nm with a polydispersity index of 0.18 (FIG. 1). In order to eliminate large particles, the nanoparticles were filtered through a 200 nm syringe filter, resulting in a pale blue dispersion. This dispersion was dialyzed for 48 hours at a 1:100 dilution with a 0.1 M phosphate buffered saline solution containing 0.05% Tween 20 in PBS (PBST) using a 300 kDa cutoff membrane.

The dialyzed nanoparticles were then functionalized with streptavidin. A 1 mL solution of nanoparticles was stirred for 1 hour at room temperature with 0.1 mL of a 10 mg/mL solution of streptavidin. The resulting nanoparticles were dialyzed for 48 hours at a 1:100 dilution with 0.1 M PBS using a 300 kDa cutoff membrane.

The nanoparticles were then used as the detection moieties in a standard competitive ELISA format (Eagle Biosystems). Anti-estradiol 96-well microtiter plates were incubated per the kit instructions with either the supplied estradiol-enzyme conjugate or an estradiol-6-CMO biotin conjugate to create a standard curve, with each run in triplicate. After a 2 hour incubation at 37° C. the wells were washed five times with the supplied wash buffer. The biotin conjugate wells were then incubated for 30 minutes at room temperature with 0.2 mL of a 1:180 dilution of the nanoparticle solution, followed by five washes with the supplied wash buffer. Control wells were incubated with the supplied reaction and stop buffers as indicated in the kit instructions. The nanoparticle wells were then filled with 0.2 mL of a "Signal Solution" containing 0.3 g glycerol and 0.004 g resazurin per mL of DI. The plate was heated to 55° C. for 2 minutes and was then irradiated with light from a 100 W high-pressure mercury arc lamp for 30 minutes. The fluorescence of each well was then read at $\lambda_{ex}$=572 nm/$\lambda_{em}$=584 nm. A comparison of the nanoparticle-derived standard curve and the ELISA (horseradish peroxidase)-derived curve is shown in FIG. 2. The same procedure was repeated with 5 clinical samples and the data are shown in FIG. 21.

Example 2—Competitive ELISA Durability

Figure 3:
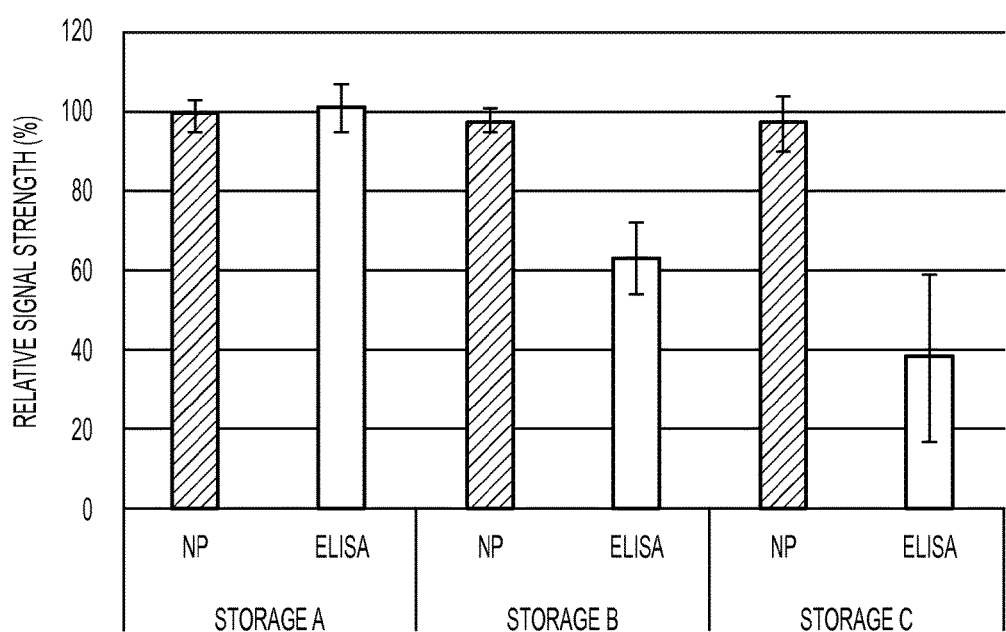
FIG. 3 shows a comparison of signal amplitudes for three different storage conditions: A, 4° C. for 1.5 months; B, 22-28° C. for 1.5 months; C, 40° C. for 2 weeks after 1 month at 4° C. The procedure for the lowest free estradiol concentration of the estradiol ELISA run in Example 1 was re-run with the solutions from the different storage conditions. The amplitude of the nanoparticle solutions exposed to all storage conditions remained within 96%. This stability represents a key nanoparticle feature: their stability lies in stark contrast to the sensitivity of the enzyme required for ELISAs, HRP. The HRP performance degrades to ~62% of its original performance after room temperature storage and <40% of its original performance after 2 weeks at 40° C. Furthermore, the HRP amplification variability increases with prolonged exposure to temperatures >4° C. The standard deviation of the enzyme stored for 2 weeks at 40° C. is 21% (absolute), in comparison with the 4° C. control, which is 5% (absolute).

The estradiol-conjugated nanoparticle solution from Example 1, as well as an estradiol-horseradish peroxidase (HRP) enzyme conjugate were exposed to three different storage criteria: Storage A was 4° C. for 1.5 months, Storage B was room temperature (22-28° C.) for 1.5 months, and Storage C was 40° C. for 2 weeks (after 1 month at 4° C.). The procedure for the lowest free estradiol concentration of the estradiol ELISA run in Example 1 was re-run with the solutions from the different storage conditions; FIG. 3 compares signal amplitudes. The amplitude of the nanoparticle solutions exposed to all storage conditions remained within 96%.

Example 3—Sandwich ELISA

Nanoparticles functionalized with streptavidin were prepared as described in Example 1.

W-doped $TiO_2$ nanoparticles were also directly functionalized with streptavidin according to the following procedure. A mixture of 1 g of W-doped $TiO_2$ nanoparticles (US-Nano) and 50 mL of a 1:1 (v/v) ratio of toluene to methyl isobutyl ketone was made. This was sonicated for 1 hour and then refluxed under nitrogen with 1 mL 3-aminopropyltriethoxysilane. The mixture was then cooled, washed with diethyl ether, and centrifuged to collect the amine-functionalized nanoparticles. After 5 washes the nanoparticles were reconstituted in 0.05% Tween 20 PBS (PBST) by sonication and dialyzed 24 hours (1:100 dilution) with PBST and a 300 kDa cutoff membrane.

The dialyzed W-doped $TiO_2$ nanoparticles were then functionalized with streptavidin. A 0.5 mL solution of nanoparticles was stirred for 1 hour at room temperature with 0.05 mL of a 10 mg/mL solution of streptavidin. The resulting nanoparticles were dialyzed for 48 hours at a 1:100 dilution with 0.5% Tween 20 PBS using a 300 kDa cutoff membrane.

These two types of streptavidin-functionalized nanoparticles were then used as the reporters in a standard sandwich ELISA protocol (eBioscience) for tumor necrosis factor-alpha (TNF-α), in which the detection antibodies were biotinylated (FIG. 4). Nanoparticles encapsulating W-doped TiO$_2$ are termed "encapsulated" nanoparticles and those directly functionalized are termed "direct-TiO$_2$" nanoparticles. A standard curve of TNF-α for the range of 8-1000 pg/mL was performed during the sample incubation step. After conjugate capture antibody binding and subsequent washing, either a 1:160 dilution of the encapsulated nanoparticle solution or a 1:75 dilution of the direct-TiO$_2$ nanoparticle solution, was introduced to each well. After washing, the Signal Solution was added and the procedure outlined in Example 1 was performed to develop the signal.

Example 4—Sandwich Assay with Pre-Chemiluminophore Signaling Agent

Biotinylated nanoparticles were prepared as in Example 3. However, the nanoparticles were loaded with fluorescein diacetate, instead of W-doped TiO$_2$. After 0.05 mL of a 10 mg/mL fluorescein diacetate solution in THF was added to Solution B, the biotin-PEG-PA and PEG-PA conjugates were added directly. The remainder of the procedure followed that in Example 3.

Figure 5:
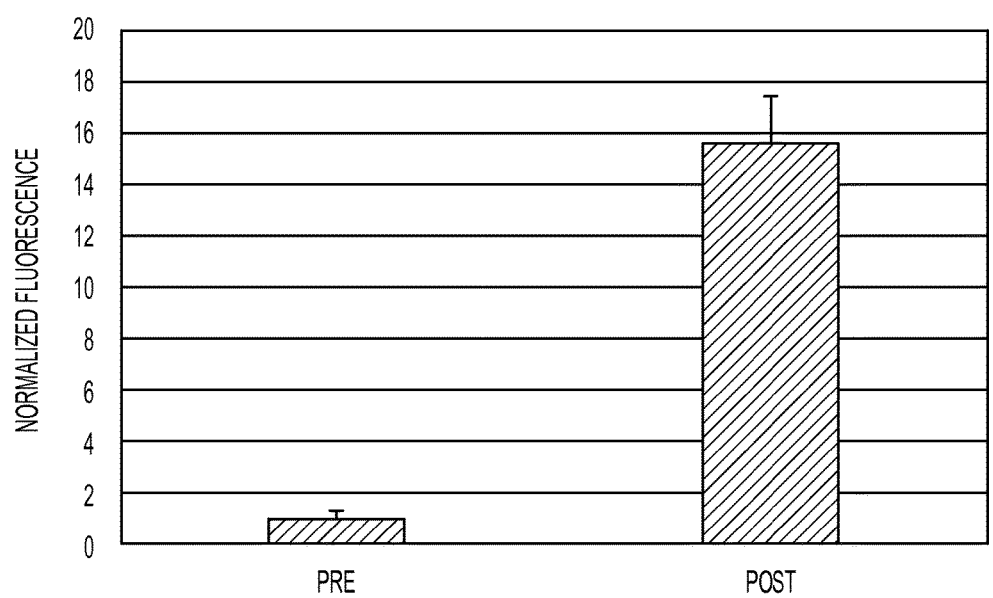
FIG. 5 demonstrates the ability of the nanoparticle-based assay to detect a binding event with a nanoparticle encapsulating a pre-chemiluminophore, fluorescein diacetate, as the signaling agent. The plot shows the normalized fluorescence ($\lambda_{ex}$=485 nm/$\lambda_{em}$=520 nm) of the detection solution before (pre) and after (post) a 2 minute treatment in base at 55° C. Normalization was performed relative to the pre-released fluorescent measurement. The basic pH of the detection solution produces the fluorescent molecule fluorescein.

The biotinylated nanoparticles were bound directly to wells in 96-well streptavidin-coated plates by incubating a 0.2 mL of a 1:100 dilution for 1 hour at room temperature in each well. After 5 washes with PBS the wells were filled with a 1:1 solution of dimethylsulfoxide (DMSO): sodium bicarbonate buffer, pH 12.5. The fluorescence ($\lambda_{ex}$=485 nm/$\lambda_{em}$=520 nm) of the solution before (pre) and after (post) a 2 minute treatment at 55° C. (FIG. 5).

Example 5—Nanoparticles with Fluorophore Signaling Agent

Biotinylated nanoparticles were prepared similarly to Example 3, with two differences. First, the nanoparticles were loaded with rhodamine 6G, instead of W-doped TiO$_2$. Second, the nanoparticles consisted of synthetic carnauba wax instead of synthetic beeswax. In order to accommodate the higher melting point of the synthetic carnauba wax, all mixing was performed at 85° C., instead of 70° C.

Solution B contained 0.05 mL of a 10 mg/mL rhodamine 6G solution in DMF, to which was added the biotin-PEG-PA and PEG-PA conjugates. The remainder of the procedure followed that in Example 3.

Figure 18:
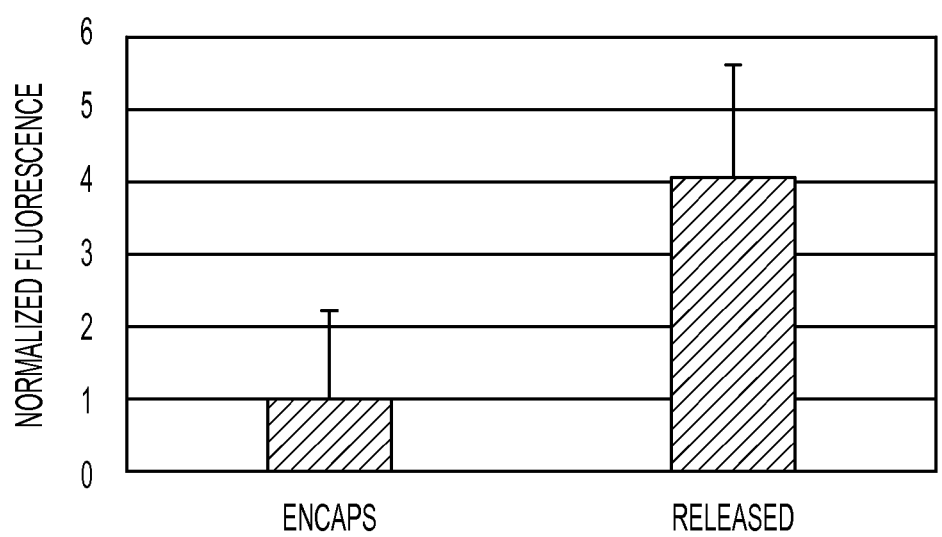
FIG. 18 demonstrates the ability of the nanoparticle-based assay to detect a binding event with a nanoparticle encapsulating a chemiluminophore signaling agent, rhodamine 6G. The plot shows the normalized fluorescence at $\lambda_{ex}$=540 nm/$\lambda_{em}$=565 nm of the detection solution before and after a 2 minute treatment at 55° C. The enhanced signal of the "released" rhodamine in comparison to the "encapsulated" rhodamine is due to its liberation from the nanoparticles and its dissolution in the detection solution. This represents a key importance of releasing chemiluminophores from the nanoparticles in order to maximize the signal. Normalization was performed relative to the signal of the bound nanoparticles before triggered release.

The biotinylated nanoparticles were bound directly to wells in 96-well streptavidin-coated plates by incubating a 0.2 mL of a 1:100 dilution for 1 hour at room temperature in each well. After 5 washes with PBS the wells were filled with a 1:3 solution of DMSO:PBS. The fluorescence ($\lambda_{ex}$=540 nm/$\lambda_{em}$=565 nm) of the solution was measured (encaps, FIG. 18). The presence of rhodamine 6G-containing nanoparticles show a slight increase in signal above background (~5-15%). Upon release from the nanoparticles, accomplished with a 2 minute treatment at 70° C. (released), the fluorescence intensity is significantly increased due to rhodamine 6G release from the nanoparticles. This is due to the solvation effects of the apolar/polar solvent mixture, in comparison to the hydrophobic nanoparticle, as well to the decreased quenching upon rhodamine 6G release from the nanoparticles (FIG. 18).

Example 6—Nanoparticles Encapsulating Multiple Signaling Agents

Nanoparticles were prepared as in Example 4. However, instead of fluorescein diacetate alone, the nanoparticles were loaded with both fluorescein diacetate and 8-hydroxyquinoline, (0.025 mL of a 10 mg/mL fluorescein solution in THF and 0.025 mL of a 10 mg/mL 8-hydroxyquinoline solution in THF were added to Solution B). The remainder of the procedure followed that in Example 4.

Figure 6:
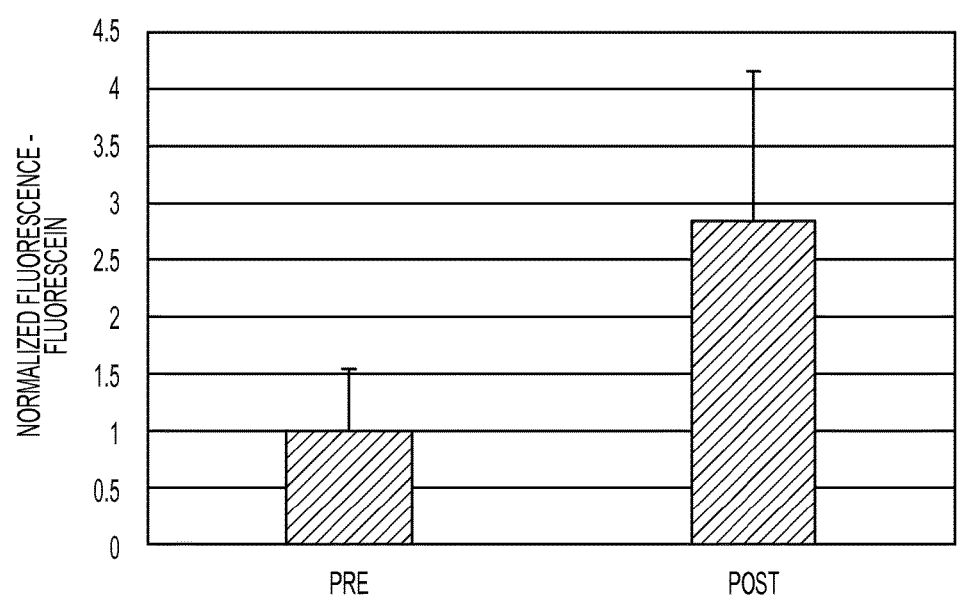
FIG. 6 demonstrates the ability of the nanoparticle-based assay to detect a binding event with a nanoparticle encapsulating two signaling agents. Both the pre-chemiluminophore fluorescein diacetate and the chelator 8-hydroxyquinoline (HQ) were encapsulated. The plot shows the normalized fluorescence at $\lambda_{ex}$=485 nm/$\lambda_{em}$=520 nm, which detects fluorescein, of the detection solution before and after a 2 minute treatment at 55° C. Normalization was performed relative to the pre-released fluorescent measurement. The basic pH of the detection solution produces the fluorescent molecule fluorescein. The multi-signal capability represents a significant enhancement over current state-of-the-art ELISAs, which only produce one signal. Such a duplicate signal may be used for additional calibration.
Figure 7:
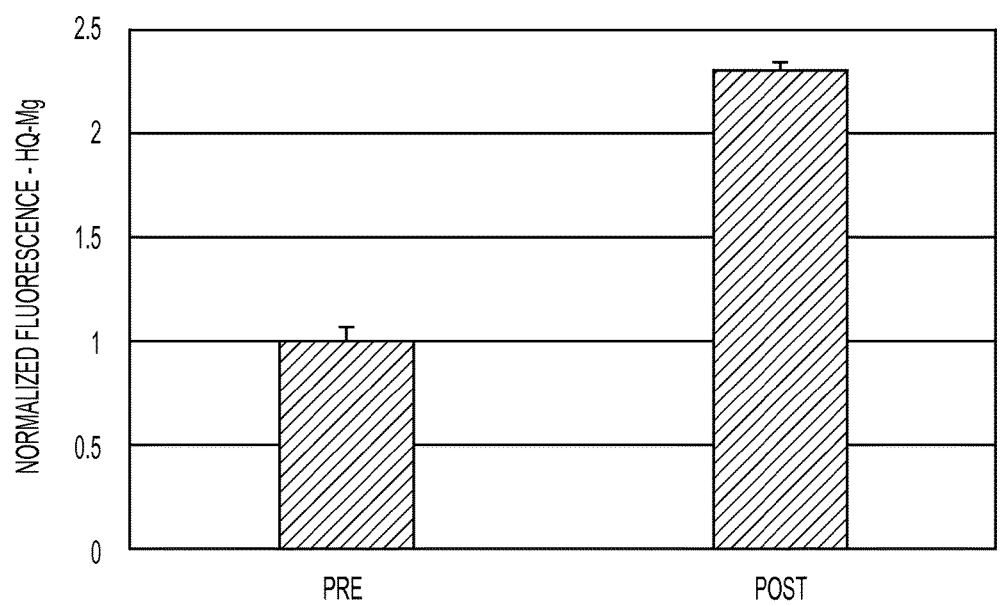
FIG. 7 demonstrates the ability of the nanoparticle-based assay to detect a binding event with a nanoparticle encapsulating two signaling agents. Both the pre-chemiluminophore fluorescein diacetate and the chelator 8-hydroxyquinoline (HQ) were encapsulated. The plot shows the normalized fluorescence at $\lambda_{ex}$=360 nm/$\lambda_{em}$=535 nm, which detects the 8-hydroxyquinoline-Mg complex, HQ-Mg, of the solution before and after a 2 minute treatment at 55° C. Normalization was performed relative to the pre-released fluorescent measurement. The multi-signal capability represents a significant enhancement over current state-of-the-art ELISAs, which only produce one signal. Such a duplicate signal may be used for additional calibration.

The biotinylated nanoparticles were bound directly to wells in 96-well streptavidin-coated plates by incubating a 0.2 mL of a 1:100 dilution for 1 hour at room temperature in each well. After 5 washes with PBS the wells were filled with a 1:1 solution of DMSO:sodium bicarbonate buffer, pH 12.5, containing 0.1 M MgCl$_2$. The fluorescence at both $\lambda_{ex}$=485 nm/$\lambda_{em}$=520 nm (fluorescein) and $\lambda_{ex}$=360 nm/$\lambda_{em}$=535 nm (8-hydroxyquinoline-Mg complex, HQ-Mg) of the solution before and after a 2 minute treatment at 55° C. are shown in FIG. 6 and FIG. 7 respectively.

Example 7—Nanoparticles with Metal Ion Catalyst Signaling Agent

Figure 8:
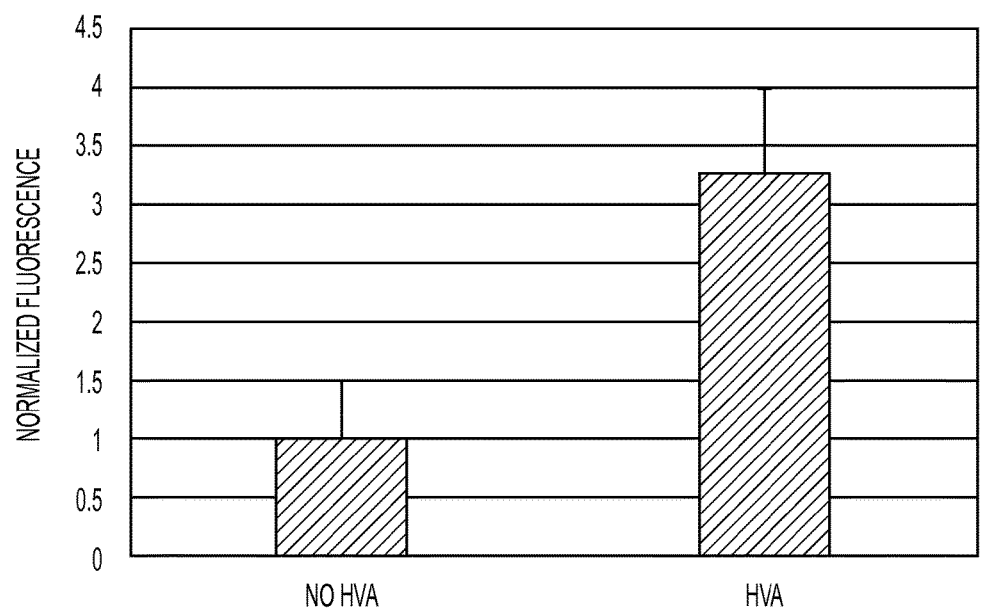
FIG. 8 demonstrates the ability of the nanoparticle-based assay to detect a binding event with an iron ion as the catalyst. The plot shows the normalized fluorescence ($\lambda_{ex}$=315 nm/$\lambda_{em}$=425 nm) difference between wells containing and without the oxygen radical-sensitive probe homovanillic acid (HVA). Normalization was performed relative to the wells without HVA.

Streptavidin-functionalized iron oxide nanoparticles of 27 nm average diameter (Nanocs) were used as the "reporters" in the sandwich ELISA described in Example 2. After nanoparticle incubation and washing, 0.2 mL of a Signal Solution consisting of 0.1 M sodium citrate titrated with HCl to pH 3.0 and containing 1 mM hydrogen peroxide, 5 mM homovanillic acid (HVA), and 1 mM Triton X-100 was added. The solution was irradiated with a 5 W diode at 400-420 nm for 30 minutes. The fluorescence ($\lambda_{ex}$=315 nm/$\lambda_{em}$=425 nm) difference between wells containing and without HVA is shown in FIG. 8.

Example 8—Liquid-Filled Nanoparticles with Chelator Signaling Agent

Liposomes were prepared using the extrusion technique. A mixture of phosphatidylcholine, cholesterol, and a biotinylated phosphatidyl ethanolamine (Avanti Polar Lipids) was prepared in dichloromethane in a 10:1:0.1 molar ratio. The solvent was evaporated in a glass vial and the lipids were then reconstituted by vortexing with a 10 mM MgCl$_2$ aqueous solution. The final liposomes were formed by 10 extrusions through a 200 nm membrane. The biotinylated liposomes were then dialyzed for 24 hours in a 1:100 dilution with 10 mM NaCl in DI using a 300 kDa cutoff membrane.

Figure 9:
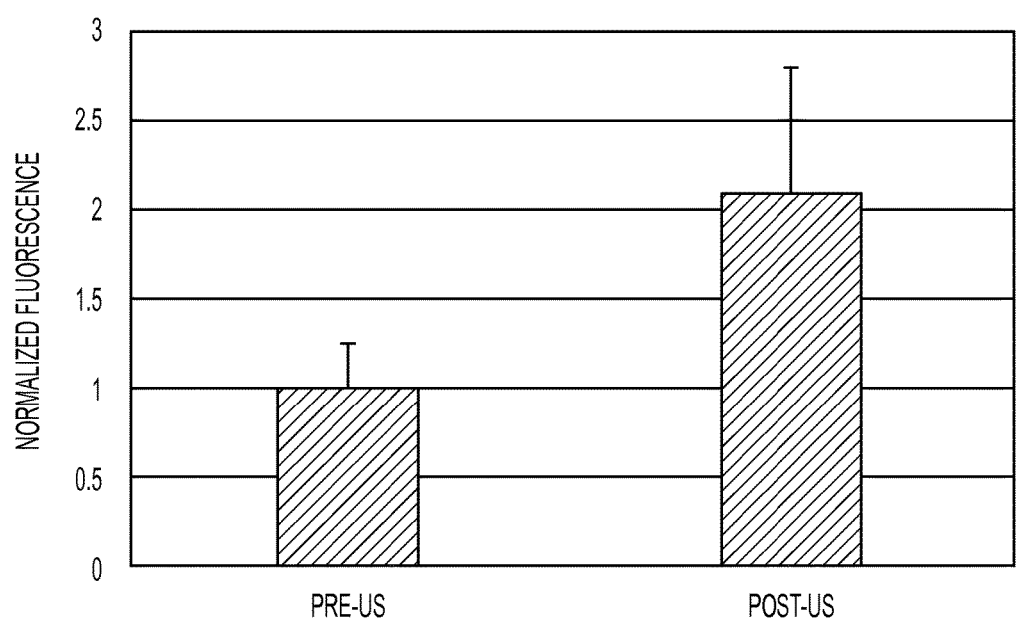
FIG. 9 demonstrates the ability of the nanoparticle-based assay to detect a binding event using a liquid phase in place of a solid matrix in the nanoparticle core with a magnesium ion as the signal generator. The plot shows the normalized fluorescence ($\lambda_{ex}$=360 nm/$\lambda_{em}$=535 nm) of the solution before and after a 2 minute treatment at 50% power of a 250 W probe-tip ultrasonicator (US), which demonstrates an alternate method for nanoparticle dissociation. Normalization was performed relative to the pre-US fluorescence measurement. This demonstrates the ability to trigger signaling agent release with sound energy.

The biotinylated nanoparticles were bound directly to wells in 96-well streptavidin-coated plates by incubating a 0.2 mL of a 1:1000 dilution for 1 hour at room temperature in each well. After 5 washes with PBS the wells were filled with a 1:4 solution of DMSO:PBS containing 0.1 M MgCl$_2$. The fluorescence ($\lambda_{ex}$=360 nm/$\lambda_{em}$=535 nm) of the solution before and after a 2 minute treatment at 50% power of a 250 W probe-tip ultrasonicator (US) is shown in FIG. 9.

Example 9—Nanoparticles with Signaling Agent Released by a Combination Trigger

Light-sensitive nanoparticles were synthesized as follows. A solution of commercial photoresist (S1813) in propylene glycol monomethyl ether acetate (PGMEA) was diluted 1:10 with further PGMEA and 0.05 mL of a 10 mg/mL fluorescein diacetate solution in THF was added. The resulting solution was then added to a 100 mL solution of 1% (w/v) Span 40 in mineral oil at 60° C. The emulsion was sonicated at the 50% power setting of a 250 W probe-tip sonicator for 30 seconds. The emulsion was then stirred at 400 rpm for 12 hours at 60° C. The resulting dispersion was diluted 1:10 with hexanes and centrifuged.

The nanoparticles were reconstituted in a 0.5% (w/v) Span 60 in hexanes solution and heated to 60° C. A 5:1 volume ratio of PEG-PA and biotin-PEG-PA was added to the hexane mixture before dispersing it in a 2% (w/v) solution of Tween 80 in DI. The emulsion was sonicated at the 50% power setting of a 250 W probe-tip sonicator for 30 seconds. The emulsion was then stirred at 400 rpm for 12 hours at room temperature.

Figure 10:
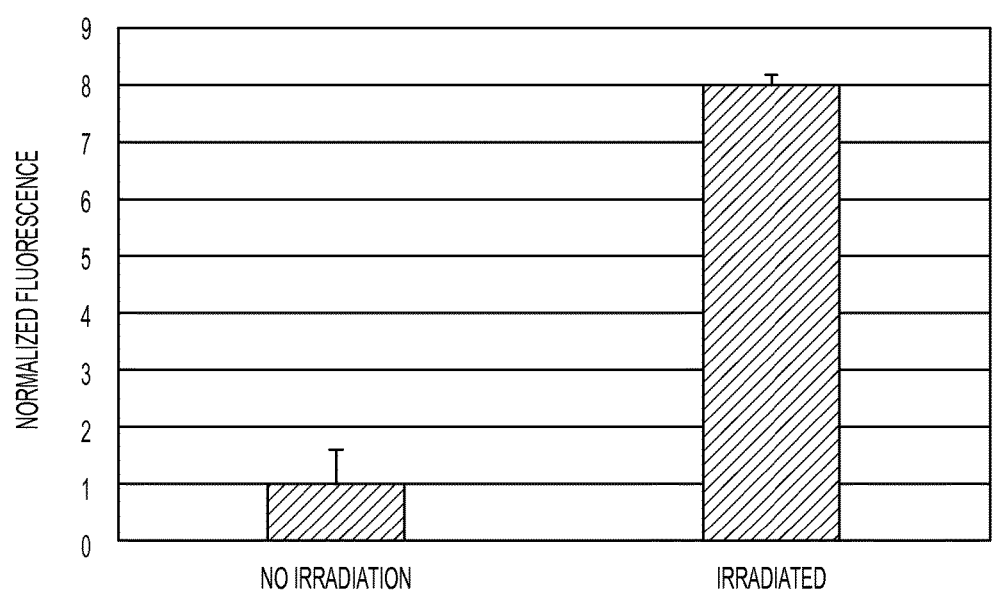
FIG. 10 demonstrates the ability of the nanoparticle-based assay to detect a binding event using a light-sensitive matrix with a pre-chemiluminophore signaling agent. The plot shows the normalized fluorescence at $\lambda_{ex}$=485 nm/$\lambda_{em}$=520 nm of the solution with and without a 30 second irradiation with light from a 100 W high-pressure mercury arc lamp, which chemically alters the photosensitive polymer matrix, enabling it to dissolve in a basic solution. This, in turn, releases fluorescein diacetate, which is converted to fluorescein by the basic pH. Normalization was performed relative to the non-irradiated control. This demonstrates the ability to trigger signaling agent release with electromagnetic energy.

The biotinylated nanoparticles were bound directly to wells in 96-well streptavidin-coated plates by incubating a 0.2 mL of a 1:100 dilution for 1 hour at room temperature in each well. After 5 washes with PBS the wells were filled with a 1% (w/v) aqueous solution of tetramethyl ammonium hydroxide. The fluorescence at $\lambda_{ex}$=485 nm/$\lambda_{em}$=520 nm of the solution with and without a 30 second irradiation with light from a 100 W high-pressure mercury arc lamp is shown in FIG. 10.

Example 10—Chelator Signaling Agent with Microparticle-Based Reagents

Biotinylated nanoparticles containing 8-hydroxyquinoline were prepared as described in Example 6. Magnesium chloride-containing microparticles were synthesized as follows:

Solution 10-A was made by dissolving 2 g of lecithin in 100 mL of deionized water (DI). This solution was stirred at 70° C.

Solution 10-B was made by dissolving 0.125 g of Span 60 and 0.375 g of microcrystalline wax (avg melting point 62-65° C.) in 2 mL of heptane at 70° C. After melting and dissolution, 0.2 mL of a 0.1 M solution of $MgCl_2$ in DI was added. The solution was sonicated for 20 seconds at the 60% power setting with a 250 W probe-tip sonicator.

Solution 10-B was then added to Solution 10-A and the resulting emulsion was stirred at 500 rpm with a stir bar. After 1 minute of stirring, the beaker containing the emulsion was put on ice and stirring continued for 12 hours.

The resulting microparticles were diluted 1:10 and dialyzed for 48 hours at a 1:100 dilution with 0.1 M PBS using a 300 kDa cutoff membrane.

Figure 11:
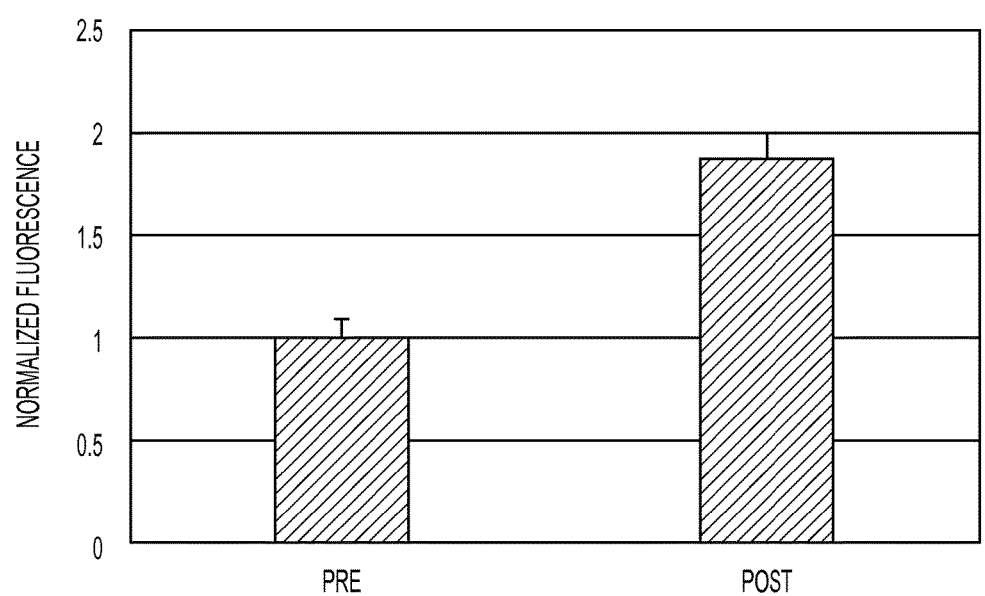
FIG. 11 demonstrates the ability of the nanoparticle-based assay to function with reagents contained in a microparticle. The plot shows the normalized fluorescence ($\lambda_{ex}$=360 nm/$\lambda_{em}$=535 nm) of the solution before and after a 2 minute treatment at 55° C. Normalization was performed relative to the pre-released signaling agent. This enables the signal to be produced without the need for solution exchange, an important benefit for many point-of-care assays, such as lateral flow assays.

The biotinylated nanoparticles were bound directly to wells in 96-well streptavidincoated plates as described in Example 6. After 5 washes with PBS the wells were filled with a 1:1 solution of dimethyl sulfoxide:PBS containing a 1:50 dilution of the $MgCl_2$ microparticles. The fluorescence ($\lambda_{ex}$=360 nm/$\lambda_{em}$=535 nm) of the solution before (pre) and after (post) a 2 minute treatment at 55° C. is shown in FIG. 11.

Example 11—DNA-Dye Complexation

Biotinylated nanoparticles were prepared as in Example 3. However, the nanoparticles were loaded with bisBenzimide H 33258 (Hoescht 33258), instead of W-doped $TiO_2$. After 0.05 mL of a 10 mg/mL Hoescht 33258 solution in dimethyl formamide (DMF) was added to Solution B, the biotin-PEG-PA and PEG-PA conjugates were added directly. The remainder of the procedure followed that in Example 3.

Figure 19:
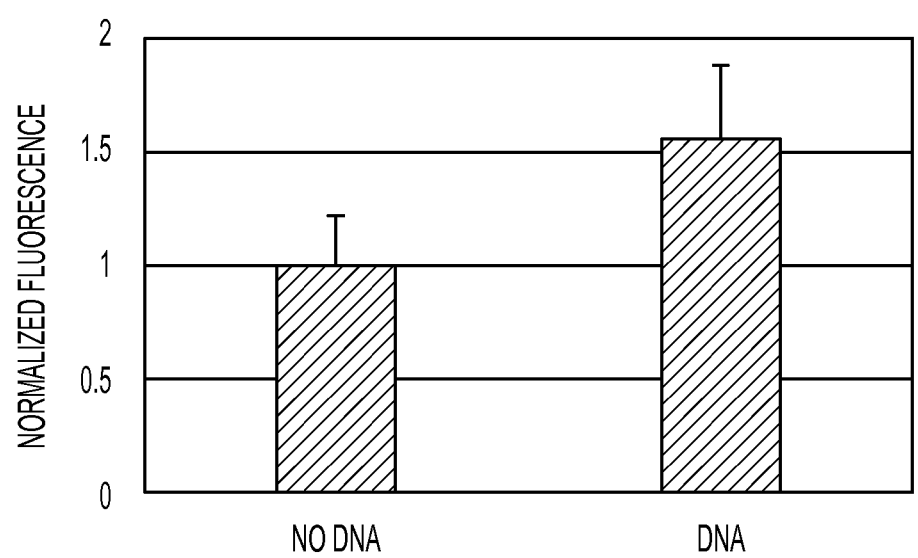
FIG. 19 demonstrates the ability of the nanoparticle-based assay to detect a binding event with a nanoparticle encapsulating a DNA intercalator, bisBenzimide H 33258 (Hoescht 33258). The plot shows the normalized fluorescence at $\lambda_{ex}$=360 nm/$\lambda_{em}$=460 nm of the detection solution before and after a 2 minute treatment at 55° C. and compares the results to a nanoparticle-free "blank" 1:3 solution of DMSO: phosphate buffered saline containing 10 mg/mL DNA (double-stranded) from salmon sperm. The presence of DNA significantly enhances the DNA intercalator signal. Normalization was performed relative to the signals from the samples without DNA.

The biotinylated nanoparticles were bound directly to wells in 96-well streptavidin-coated plates by incubating a 0.2 mL of a 1:100 dilution for 1 hour at room temperature in each well. After 5 washes with PBS the wells were filled with a 1:3 solution of DMSO:PBS alone (no DNA) or containing 10 mg/mL dsDNA from salmon sperm (DNA). The fluorescence ($\lambda_{ex}$=360 nm/$\lambda_{em}$=460 nm) of each solution was measured after a 2 minute treatment at 55° C. The presence of dsDNA significantly enhances the signal (FIG. 19).

Example 12—Dual-Fluorescence Multiplexed Detection

Biotinylated synthetic beeswax nanoparticles containing fluorescein diacetate were synthesized as described in Example 4. They were functionalized with an avidin-horseradish peroxidase (HRP) conjugate by stirring a 1 mL solution of nanoparticles for 1 hour at room temperature with 0.1 mL of a 10 mg/mL solution of avidin-HRP conjugate. The resulting nanoparticles were dialyzed for 48 hours at a 1:100 dilution with 0.1 M PBS using a 300 kDa cutoff membrane. These nanoparticles are termed NP-13-F.

Biotinylated synthetic carnauba wax nanoparticles containing rhodamine 6G were synthesized as described in Example 5. These nanoparticles, termed NP-13-R, were used without further modification.

Figure 20:
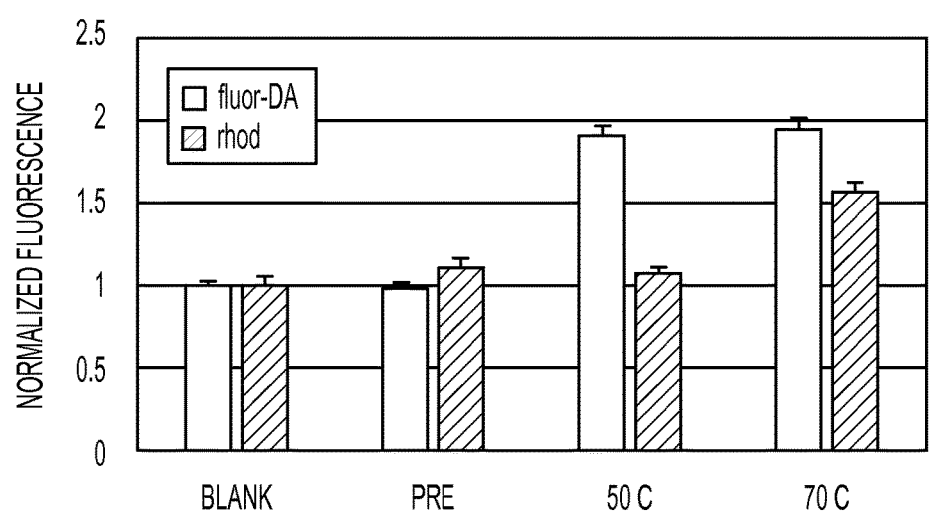
FIG. 20 demonstrates the ability of the nanoparticle-based assay to function in a multiplex format. Nanoparticles with different chemiluminophore and pre-chemiluminophore signaling agents and different wax matrix melting points were prepared as described in Example 21. The nanoparticles were functionalized with biotin and competitively bound to immobilized streptavidin. The data demonstrate the ability to control the output signal based on the temperature of the basic detection solution. Fluorescein was measured at $\lambda_{ex}$=485 nm/$\lambda_{em}$=520 nm and rhodamine at $\lambda_{ex}$=540 nm/$\lambda_{em}$=565 nm. Both signals were normalized to a baseline from samples incubated with nanoparticles containing no signaling agents (blank). The fluorescence signal upon addition of the detection solution but before the temperature was increased ("pre") is similar to the blank background. Note the rhodamine signal is increased slightly above background, owing to the presence of rhodamine in the nanoparticles. Upon increasing the temperature to 50° C., the fluorescein diacetate is released and converted into fluorescein due to the basic pH of the detection solution. Thus, fluorescein is observed. Rhodamine, in contrast, remains near baseline, due to its encapsulation in a more temperature-stable matrix. Upon increasing the temperature to 70° C., the rhodamine is released, producing an increased fluorescent signal.

The NP-13-R nanoparticles were diluted 1:15 and mixed with a 20 ng/mL solution of a biotinylated conjugate of anti-HRP IgG in PBS. This mixture was added to the wells (0.2 mL each) in 96-well streptavidin-coated plates and incubated 1 hour at room temperature. After 5 washes with PBS the wells were filled with a 1:20 dilution of the NP-13-F nanoparticles and were incubated at room temperature for 2 hours. The wells were again washed 5 times with PBS and filled with a 1:3 solution of DMSO:PBS, pH 10.5. The fluorescence was read at $\lambda_{ex}$=485 nm/$\lambda_{em}$=520 nm (fluorescein) and $\lambda_{ex}$=540 nm/$\lambda_{em}$=565 nm (rhodamine 6G) for all following measurements. First, a background was taken, before the fluorophores were released (pre). A slight increase in rhodamine 6G signal is again apparent, as in Example 6, which is not the case for the diacetate-quenched fluorescein diacetate nanoparticles (FIG. 20).

A 30 second heat treatment at 50° C. was sufficient to release the fluorescein diacetate from the NP-13-F nanoparticles into the solvent system, producing a significantly enhanced fluorescence signal (50° C.). As in Example 4, this is due to the basic environment-induced hydrolysis, which produces the fluorescent fluorescein species. The NP-13-R nanoparticles, however, did not receive sufficient thermal energy to release their contents, thus the rhodamine fluorescent signal is not increased.

A heat treatment for 2 minutes at 70° C. was then performed, which was sufficient to release the rhodamine into the solvent system, thereby increasing its fluorescence (70° C.). The fluorescein fluorescence intensity was not significantly impacted by this step.

Example 13—Nanoparticles with Fluorescein Dilaurate (FL-DL) Signaling Agent

Materials:
Fluorescein-Dilaurate (FL-DL) (Sigma Aldrich);
DSPE-PEG-2k-Biotin (Lysan Bio);
Ethanol (Sigma); and
De-Ionized (DI) Water.

Fluorescein dilaurate (FL-DL) nanoparticles (NPs) were prepared according to the following procedure and steps:
1. 20 mgs of FL-DL were weighed into a clear glass scintillation vial.
2. 1000 mgs of Ethanol were added, and the above FL-DL was dissolved by vortexing the vial.

3. 10 mgs of DSPE-PEG-2k-Biotin were added to the above mixture and dissolved by vortexing.
4. 40 gm of DI water were weighed out in a beaker, and a stir-bar was added. The beaker was placed on a magnetic stirrer and stirred at 200 RPM.
5. The Ethanol solution of Step 3 was added to the beaker in a drop wise fashion.
6. 200 gm of DI water was added to the mixture of Step 5.
7. Purify, and the volume of the mixture was concentrated to 20 mLs.
8. 100 gms of PBST (0.05% Tween 80) were added to the concentrate of Step 7.
9. Tangential Flow Filtration (TFF) was used for purification and concentration. Purified NPs were concentrated ~12-fold to 20 mL and collected in a glass scintillation vial.
10. The above collected nanoparticle formulation of Step 9 was filtered through a 0.2 μm Filter.

TABLE 3

| | Mol % DSPE-PEG-2k-Biotin | Mol % FL-DL |
|---|---|---|
| SL-113 | 10 | 90 |
| SL-118 | 8 | 92 |
| SL-119 | 6 | 94 |
| SL-120 | 4 | 96 |

| | Mol % DSPE-PEG-5k-Biotin | Mol % FL-DL |
|---|---|---|
| SL-123 | 6 | 94 |

Example 14—Nanoparticles with Multiple Signaling Agents Comprising a Catalyst and Pre-Chemiluminophore Materials:
Fe(III)-TAML® (sodium salt) metalorganic complex purchased from GreenOx (see, e.g., U.S. Pat. No. 6,100,394, which is incorporated herein by reference in its entirety) having the following structure,

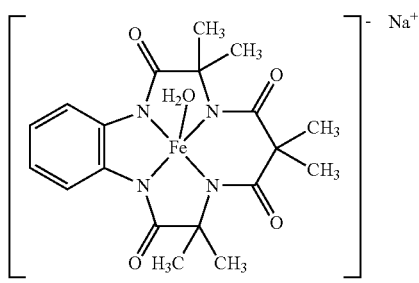

Adogen 464 (Sigma Aldrich)
Fluorescein-Dilaurate (FL-DL) (Sigma Aldrich)
DSPE-PEG-2k-Biotin (Lysan Bio)
Benzyl Alcohol (BA) (Sigma)
Ethyl Acetate (EA) (Sigma)
De-Ionized (DI) Water Nanoparticles comprising a Fe(III)-TAML metalorganic complex were prepared according to the following procedure and steps:
1. 40 gm of DI Water were weighed in a beaker. 1.6 gm of BA were added to the beaker and stirred on a magnetic stirrer until the BA has dissolved in the DI water.
2. 2 g of BA were weighed into a 20 mLs scintillation glass vial. 5 mgs of TAML and 20 mgs of Adogen 464 were added to the BA solution, which were dissolved by vortexing.
3. 20 mg of FL-DL and 1.0 mg of DSPE-PEG-2k-Biotin were added to the above mixture and also dissolved by vortexing.
4. 3 g of EA were added and mixed.
5. The contents of the organic mixture in step 4 were added to the aqueous solution (with BA) of Step 1.
6. A coarse emulsion was obtained by emulsifying with a hand held homogenizer.
7. The coarse emulsion of Step 6 was passed through a Microfluidizer (Microfluidics) at a pressure of 7000 psi to make a fine emulsion.
8. The fine emulsion was quenched by adding it to a beaker with 200 g of DI water with stirring to obtain the nanoparticles.
9. Tangential flow filtration (TFF) was used on the above nanoparticle solution of Step 8 and then concentrated to 20 mLs.
10. 200 mLS of PBST was added, and the mixture was concentrated by TFF to 20 mLs.
The nanoparticles were collected in a 20 mLs glass scintillation vial.
The nanoparticles were filtered through a 0.2 μm filter to give the final product.

TABLE 4

| SL-135 Composition | |
|---|---|
| Component | Mol % |
| TAML | 14 |
| Adogen 464 | 28 |
| FL-DL | 57 |
| DSPE-PEG-Biotin-2k | 1 |

Example 15—Non-Specific Binding (NSB) of Nanoparticles

Figure 14:
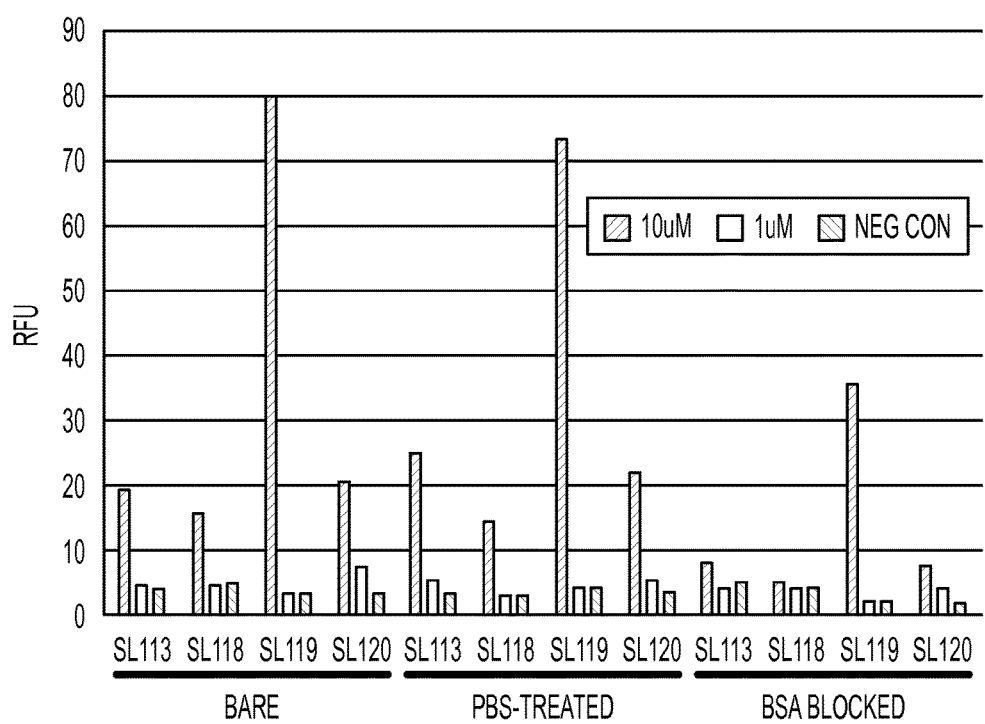
FIG. 14 provides data regarding non-specific binding (NSB) of nanoparticles (NPs) to a plastic surface pretreated with PBS containing 1% bovine serum albumin (BSA). The nonspecific binding of the nanoparticles is observed to be within 5% of the negative control for the 1 μM concentration of nanoparticles containing >5% DSPE-PEG-biotin, an indication of low nonspecific binding. In all cases the signaling agent was fluorescein dilaurate.

Four lots of nanoparticles (SL113, SL118, SL119 and SL120) were tested in this experiment for their non-specific binding activity to three surfaces, and these data are presented in FIG. 14. A Nunc MaxiSorp 96-well plate was used to generate three surfaces including: non-treated base plastic surface, plastic surface pretreated with PBS, and plastic surface pretreated with PBS containing 1% bovine serum albumin (BSA).

Each lot of nanoparticles was diluted in PBSTB1 (phosphate buffered saline containing 0.05% Tween-20 and 1% BSA, pH 7.2) to prepare a nanoparticle solution containing 10 μM equivalent fluorescein dye and a nanoparticle solution containing 1 μM equivalent fluorescein dye. Note this defines the "10 μM" or "1 μM" concentrations. A total of 200 μL of 10 μM or 1 μM solution was added to each well in triplicate and the plate was incubated at room temperate for 60 minutes. For the no particle negative control, 200 μL per well of PBSTB1 was used in duplicate. At the end of incubation, the ynbound nanoparticles were removed by a total of 4 washes with 350 μL PBST using an automatic plate washer. The residual liquid of each well was removed by gently tapping the plate (top down) onto clean tissue paper 3-5 times.

Then, 150 μL of pure ethanol was added to each well to disrupt the nanoparticle and 50 μL of 1M NaOH was added to each well to breakdown the ester bond between fluorescein dilaurate generating free fluorescein dye molecules.

The fluorescence was read using a SpectraMax M2 plate reader with excitation/emission/cutoff setting at 490/545/530.

Overall, these nanoparticles showed very low non-specific binding activity to bare plastic surface and PBS-pretreated surface. Pretreatment of the plastic surface with 1% BSA, common before the antigen-binding step(s) of immunoassays as known to those skilled in the art, further reduced this non-specific binding.

Example 16—NSB of Nanoparticles in Complex Media

Figure 15:
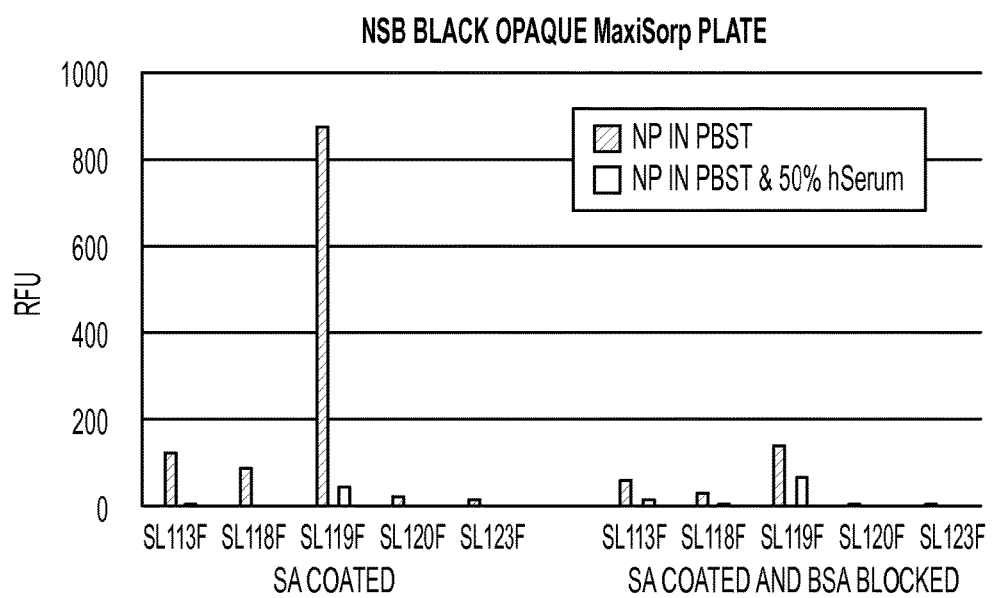
FIG. 15 provides data regarding non-specific binding by nanoparticles to two surfaces. The decreased nonspecific binding of the nanoparticles in the serum-containing media versus buffer alone, PBS with 0.05% Tween-20 (PBST), represents a key feature of the nanoparticles. For all DSPE-PEG-biotin concentrations, the NSB in complex media was <50% the level in PBST alone. Such background reduction in complex media lies in stark contrast to conventional enzyme labels from ELISAs. In all cases the signaling agent was fluorescein dilaurate.

Five lots of nanoparticles (SL113, SL118, SL119, SL120 and SL123) were tested in this experiment for their non-specific binding activity to two surfaces, and these data are presented in FIG. 15.

A MaxiSorp 96-well plate was pretreated with 100 μL per well of 10 ug/mL streptavidin (SA) in PBS for 60 minutes at room temperature. The plate was washed with PBST for a total of four times. Then, half of the plate was treated with 100 μL per well of PBSB1 (PBS containing 1% BSA) for additional 60 minutes. After another 4× washing, the plate was used for the binding assay.

Two binding buffer matrices were used in this experiment: PBST (PBS containing 0.05% Tween-20) and PBST containing 50% human serum (PBST-50% hSerum). The nanoparticles were diluted in PBST or PBST-50% hSerum to 10 μM equivalent fluorescein dye concentration. A total of 200 μL per well of each diluted nanoparticle solution was added to the well coated with streptavidin or well coated with streptavidin and blocked with PBSB1. The plate was incubated at room temperate for 60 minutes. At the end of incubation, the non-bound nanoparticles were washed off by a total of 4 washes each with 350 μL PBST using an automatic plate washer. The residual liquid of each well was removed by gently tapping the plate (top down) onto clean tissue paper 3-5 times. The fluorescence signal was collected as described previously.

The nanoparticles (lots—SL119, SL120 and SL123) showed very low non-specific binding activity to SA coated surface and SA-BSA coated surface in both PBST and PBST containing 33% human serum. In PBST, SL119 showed much higher non-specific binding than other lots of nanoparticles tested in PBST matrix, addition of human serum into PBST significantly reduced this elevated non-specific signal. The presence of human serum in binding buffer overall reduced the non-specific binding.

Example 17—Adiponectin Sandwich Immunoassay with Nanoparticles Containing Pre-Chemiluminophore Signaling Agent Nanoparticles were prepared and purified according to the procedure of SL-113, with a carboxylic acid-functionalized DSPE-PEG derivative, DSPE-PEG-2k-COOH, replacing the DSPE-PEG-2k-Biotin used for SL-113. After purification, the carboxylic acid was activated in MES buffer at pH 5, through the addition of 2 mM 1-Ethyl-3-(3-dimethylaminopropyl)-carbodiimide (hydrochloride salt) and 5 mM N-hydroxysulfosuccinimide. The activation reaction proceeded for 15 min at room temperature, after which unreacted EDC was deactivated with 2 mM 2-mercaptoethanol. A commercial anti-biotin antibody (Abcam) at ~1 mg/mL in 1× PBS was then added to the activated particles, and the pH was titrated to ~7.2. The coupling reaction proceeded for 2 hours at room temperature with stirring. The reaction volume was then loaded into a 300 kD cutoff dialysis tubing (Spectrum Labs) and dialyzed into a 1:1000 dilution of 1×PBS overnight. The antibody-functionalized nanoparticles were collected and stored at 4° C. until use.

A sandwich immunoassay was performed according to the kit instructions. A RayBiotech human adiponectin ELISA kit was purchased (ELH-ADIPONECTIN-001), and two sets of standards, each in triplicate, were prepared according to the kit instructions. In brief, to a kit-supplied capture antibody-coated 96-well microplate, varying concentrations of the provided standard were added and binding proceeded for 2 hours. The wells were washed 4 times followed by the addition of the kit-provided biotinylated detection antibody, and then diluted according to instructions. Binding proceeded for 1 hour followed by washing. The kit-provided streptavidin-HRP conjugate was then added to the first set of standards and the anti-biotin-functionalized nanoparticles were added to the second set. Binding proceeded for 30 minutes and was followed by washing. The kit-supplied, TMB-based detection solution was added to the HRP-containing wells and the reaction was allowed to proceed for 20 min, at which point the stop solution was added and the signal was measured by absorbance. In parallel, the 1:1 ethanol:1M NaOH nanoparticle signal-generating solution was added to nanoparticle-containing wells and the signal was read fluorescently.

All measurements were taken with a Molecular Devices SpectraMax M2 microplate reader and the data shown were normalized to the zero-adiponectin point (FIG. 16).

Example 18—Assay Using Nanoparticles with Multiple Signaling Agents Comprising a Catalyst and Pre-Chemiluminophore One lot of nanoparticles (SL131) was prepared with encapsulated fluorescein dilaurate and TAML catalyst, along with biotinylated surface. A 1:3 seral dilutions of this particle are prepared and 100 μL per well of each diluted solution was added to a commercial streptavidin coated 96-well microtiter plate and incubated at room temperature for 60 min, to allow the biotinylated particles to bind to the streptavidin on the well bottom. The plate was then washed with 350 μL PBST per well for a total of 4 times to remove non-bound nanoparticle from the well. Upon binding, a SA-biotin-nanoparticle complex is formed.

The presence of the specifically bound nanoparticles was visualized by addition of 150 μL ethanol and 50 μL of 1M NaOH per well. Ethanol disrupts the nanoparticle to release the fluorescen dilaurate molecules and NaOH frees the fluorescein from the non-fluorescent fluorescein dilaurate by breaking down the ester bond between the fluorescein and the dilaureats moieties. The fluorescent signal was collected by reading the plate at excitation/emission/cutoff of 490 nm/545 nm/530 nm, which is specific for the fluorescein.

The activity of the encapsulated TAML catalyst was tested using the on fluorescent Amplex Red as enzyme substrate. In the presence of $H_2O_2$, TAML catalyzes the oxidation of non-fluorescent Amplex Red to the strongly fluorescent resorufin with an Excitation/emission of 530/590 nm. To each well with SA-biotin captured nanoparticle, the following reagents were added—50 μL of 200 μM Amplex Red, 150 μL of carbonate-bicarbonate buffer, (pH 10.01), 50 μL of 1 mM $H_2O_2$. After a brief mixing by gently tapping the plate and a 15 minute incubation at room temperature, the fluorescent signal was collected by reading the plate at Ex530/Em590/Cutoff590.

Figure 17:
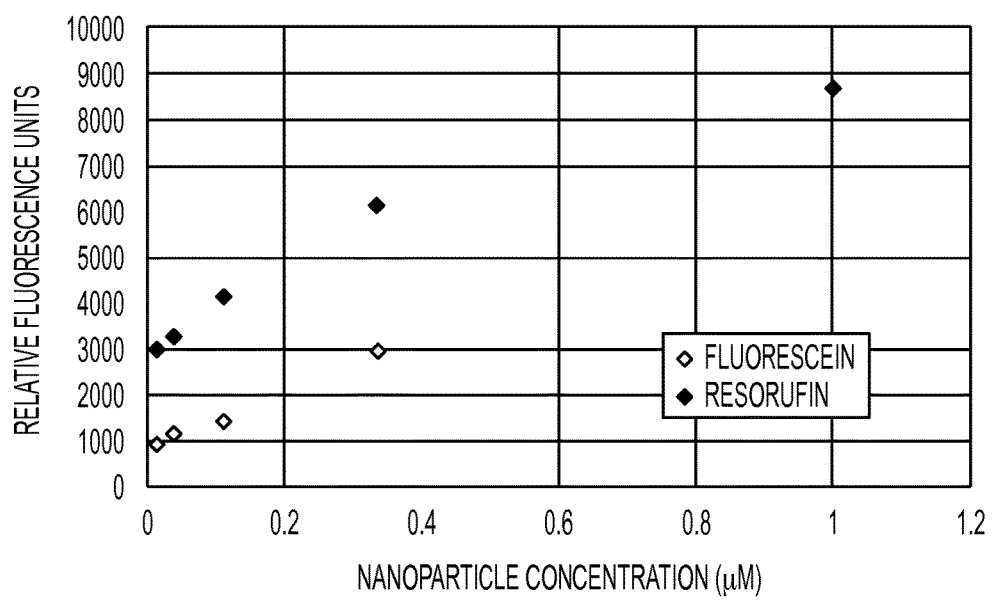
FIG. 17 demonstrates the ability of a nanoparticle to be loaded with two signaling agents of different types: a pre-chemiluminophore, fluorescein dilaurate, and a metalorganic catalyst, comprising a tetraamido macrocyclic ligand (TAML). The data show the signal resulting from the detection solution upon biotinylated "SL131" nanoparticle binding to immobilized streptavidin. The TAML catalyzes a reaction that oxidizes the non-fluorescent 10-acetyl-3,7-dihydroxyphenoxazine to the fluorescent resorufin, in the presence of hydrogen peroxide. The reaction solution pH is adjusted to ~10 using sodium hydroxide, which simultaneously hydrolyzes the fluorescein dilaurate and produces fluorescein. The fluorescent signals of both fluorescein dilaurate-derived fluorescein and TAML-dependent resorufin are correlated with the concentration of SL131 nanoparticles.

As shown in FIG. 17, the fluorescent signals of both fluorescein dilaurate dependent fluorescein and TAML-dependent resorufin are correlated with the concentration of Sl131 nanoparticle.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of examples only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

We claim:

1. A method of detecting an analyte, comprising:
   (i) incubating a sample suspected of having an analyte of interest with a binding agent specific to the analyte under conditions that permit binding between the analyte and the binding agent; wherein the binding agent is associated with a nanoparticle comprising a first signaling agent and a second signaling agent; wherein the first signaling agent is a metalorganic species catalyst comprising a metal-tetraamidomacrocyclic ligand complex, and the second signaling agent is a pre-chemiluminophore;

(ii) dissociating the nanoparticle bound to the analyte, if any, to release the signaling agents such that it results in a signal change; and (iii) determining presence or quantity of the analyte in the sample based on the signal change.

2. The method of claim 1, wherein the nanoparticle further comprises one or more matrix-forming agents providing a matrix, wherein the signaling agents are embedded in the matrix.

3. The method of claim 1, wherein the binding agent is selected from the group consisting of antibodies or antigen-binding fragments thereof, enzymes, oligonucleotides, DNA, RNA, PNA, or LNA, proteins, peptides, polypeptides, receptors, ligands, small molecules, aptamers, polysaccharides, plastibodies, affibodies, camelids, fibronectins, and a combination thereof.

4. The method of claim 1, wherein the nanoparticle comprises one or more functional groups for conjugating the nanoparticle to the binding agent.

5. The method of claim 4, wherein the functional group is linked to the outer surface via polyethylene glycol (PEG).

6. The method of claim 1, wherein step (ii) and step (iii) are performed simultaneously in a solution.

\* \* \* \* \*